United States Patent
Cottone et al.

(10) Patent No.: US 10,617,847 B2
(45) Date of Patent: Apr. 14, 2020

(54) VARIABLE FLEXIBILITY CATHETER SUPPORT FRAME

(71) Applicant: OrbusNeich Medical PTE. LTD., Singapore (SG)

(72) Inventors: Robert J. Cottone, Davie, FL (US); Mohamad Ike Juman, Davie, FL (US)

(73) Assignee: ORBUSNEICH MEDICAL PTE. LTD., Singapore (SG)

( * ) Notice: Subject to any disclaimer, the term of this patent is extended or adjusted under 35 U.S.C. 154(b) by 0 days.

(21) Appl. No.: 16/255,141

(22) Filed: Jan. 23, 2019

(65) Prior Publication Data

US 2019/0160259 A1 May 30, 2019

Related U.S. Application Data

(63) Continuation-in-part of application No. 15/726,024, filed on Oct. 5, 2017, and a continuation-in-part of application No. 15/522,216, filed as application No. PCT/US2015/058969 on Nov. 4, 2015.

(60) Provisional application No. 62/404,552, filed on Oct. 5, 2016, provisional application No. 62/729,282, filed on Sep. 10, 2018, provisional application No.
(Continued)

(51) Int. Cl.
*A61M 25/01* (2006.01)
*A61M 25/00* (2006.01)
*A61M 25/06* (2006.01)

(52) U.S. Cl.
CPC .... *A61M 25/0113* (2013.01); *A61M 25/0054* (2013.01); *A61M 25/0009* (2013.01); *A61M 25/0013* (2013.01); *A61M 25/0108* (2013.01); *A61M 2025/0188* (2013.01); *A61M 2025/0681* (2013.01); *A61M 2205/0216* (2013.01);
(Continued)

(58) Field of Classification Search
CPC .......... A61M 25/0113; A61M 25/0102; A61M 25/0138
See application file for complete search history.

(56) References Cited

U.S. PATENT DOCUMENTS

| | | | |
|---|---|---|---|
| 4,000,739 A | 1/1977 | Stevens | |
| 4,353,358 A * | 10/1982 | Emerson | ............ A61B 1/0056 600/139 |

(Continued)

FOREIGN PATENT DOCUMENTS

| | | |
|---|---|---|
| CN | 103252014 | 8/2013 |
| EP | 0 881 921 B1 | 3/2005 |

(Continued)

OTHER PUBLICATIONS

International Search Report and Written Opinion corresponding to International Patent Application No. PCT/US17/55351 dated Mar. 7, 2018; 19 pages.
(Continued)

*Primary Examiner* — Manuel A Mendez
*Assistant Examiner* — Courtney B Fredrickson
(74) *Attorney, Agent, or Firm* — Leason Ellis LLP

(57) ABSTRACT

A guide catheter extension, including a push member having a lumen, a proximal end and a distal end; a tube frame defining a lumen therein, a longitudinal axis, and a proximal segment and a distal segment, wherein the tube frame comprises a plurality of cut patterns therein; and a tongue element extending from the proximal segment of the tube frame, wherein the tongue element is coupled to the push member.

36 Claims, 32 Drawing Sheets

Related U.S. Application Data

62/238,428, filed on Oct. 7, 2015, provisional application No. 62/075,177, filed on Nov. 4, 2014.

(52) U.S. Cl.
CPC ............... *A61M 2205/0222* (2013.01); *A61M 2205/0266* (2013.01); *A61M 2205/32* (2013.01)

(56) References Cited

U.S. PATENT DOCUMENTS

| | | | |
|---|---|---|---|
| 4,552,554 A | 11/1985 | Gould et al. |
| 5,047,045 A | 9/1991 | Arney et al. |
| 5,061,273 A | 10/1991 | Yock |
| 5,102,403 A | 4/1992 | Alt |
| 5,120,323 A | 6/1992 | Shockey et al. |
| 5,152,744 A * | 10/1992 | Krause ............. A61B 17/32002 |
| | | | 604/22 |
| 5,156,594 A | 10/1992 | Keith |
| 5,267,958 A | 12/1993 | Buchbinder et al. |
| 5,328,472 A | 1/1994 | Steinke et al. |
| 5,352,236 A | 10/1994 | Jung et al. |
| 5,358,493 A | 10/1994 | Schweich, Jr. et al. |
| 5,385,562 A * | 1/1995 | Adams ................... A61M 25/01 |
| | | | 604/159 |
| 5,413,560 A | 5/1995 | Solar |
| 5,439,445 A | 8/1995 | Kontos |
| 5,445,625 A | 8/1995 | Voda |
| 5,451,209 A | 9/1995 | Ainsworth et al. |
| 5,489,278 A | 2/1996 | Abrahamson |
| 5,507,731 A | 4/1996 | Hernandez et al. |
| 5,507,751 A | 4/1996 | Goode et al. |
| 5,527,292 A | 6/1996 | Adams et al. |
| 5,545,149 A | 8/1996 | Brin et al. |
| 5,545,151 A | 8/1996 | O'Connor et al. |
| 5,685,878 A | 11/1997 | Falwell et al. |
| 5,690,613 A | 11/1997 | Verbeek |
| 5,704,926 A | 1/1998 | Sutton |
| 5,720,300 A | 2/1998 | Fagan et al. |
| 5,730,734 A | 3/1998 | Adams et al. |
| 5,733,248 A | 3/1998 | Adams et al. |
| 5,769,829 A | 6/1998 | Mous |
| 5,776,141 A | 7/1998 | Klein et al. |
| 5,843,051 A | 12/1998 | Adams et al. |
| 5,860,963 A | 1/1999 | Azam et al. |
| 5,865,815 A | 2/1999 | Tihon |
| 5,876,344 A | 3/1999 | Baker et al. |
| 5,879,305 A | 3/1999 | Yock et al. |
| 5,891,056 A | 4/1999 | Ramzipoor |
| 5,902,290 A | 5/1999 | Peacock, III et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,143,002 A | 11/2000 | Metmeier |
| 6,199,262 B1 | 3/2001 | Martin |
| 6,217,566 B1 * | 4/2001 | Ju ............................ A61M 25/005 |
| | | | 604/526 |
| 6,338,725 B1 | 1/2002 | Hermann et al. |
| 6,398,773 B1 | 6/2002 | Bagaoisan et al. |
| 6,520,951 B1 | 2/2003 | Carrillo et al. |
| 6,595,952 B2 | 7/2003 | Forsberg |
| 6,635,022 B2 | 10/2003 | Berg et al. |
| 6,635,047 B2 | 10/2003 | Forsberg |
| 6,638,268 B2 | 10/2003 | Niazi |
| 6,860,876 B2 | 3/2005 | Chen |
| 6,997,908 B2 | 2/2006 | Carillo, Jr. et al. |
| 7,025,751 B2 | 4/2006 | Silva et al. |
| 7,232,452 B2 | 6/2007 | Adams et al. |
| 7,367,967 B2 | 5/2008 | Eidenschink |
| 7,604,612 B2 | 10/2009 | Ressemann et al. |
| D611,601 S | 3/2010 | Tamai et al. |
| 7,691,138 B2 | 4/2010 | Stenzel et al. |
| 7,736,355 B2 | 6/2010 | Itou et al. |
| 7,744,585 B2 | 6/2010 | Carrillo, Jr. et al. |
| 7,762,984 B2 | 7/2010 | Kumoyama et al. |
| 7,854,743 B2 | 12/2010 | Palasis et al. |
| 7,867,219 B2 | 1/2011 | Chambers |
| 7,981,091 B2 | 1/2011 | Root et al. |
| 7,887,529 B2 | 2/2011 | Eder |
| 7,972,294 B2 | 7/2011 | Nash et al. |
| 7,981,148 B2 | 7/2011 | Aguilar et al. |
| 8,048,032 B2 | 11/2011 | Root et al. |
| 8,057,430 B2 | 11/2011 | Grovender et al. |
| 8,142,413 B2 | 3/2012 | Root et al. |
| 8,206,370 B2 | 6/2012 | Von Oepen et al. |
| 8,292,850 B2 | 10/2012 | Root et al. |
| 8,323,241 B2 * | 12/2012 | Salahieh ............. A61M 25/0136 |
| | | | 604/95.04 |
| 8,372,056 B2 | 2/2013 | Eder |
| 8,512,282 B2 | 8/2013 | Grovender et al. |
| 8,613,706 B2 | 12/2013 | Langston |
| RE45,380 E | 2/2015 | Root et al. |
| 8,996,095 B2 | 3/2015 | Anderson et al. |
| 9,089,675 B2 | 7/2015 | Schulting |
| 9,144,662 B2 * | 9/2015 | Di Caprio ......... A61M 25/0068 |
| RE45,760 E | 10/2015 | Root et al. |
| RE45,776 E | 10/2015 | Root et al. |
| 9,332,914 B2 | 5/2016 | Langston |
| 9,333,335 B2 * | 5/2016 | Ollivier ............. A61M 25/0054 |
| 9,352,123 B2 | 5/2016 | Zhou et al. |
| RE46,116 E | 8/2016 | Root et al. |
| 9,433,427 B2 * | 9/2016 | Look ....................... A61B 17/22 |
| 9,486,611 B2 * | 11/2016 | Petersen ................ A61M 25/01 |
| 9,593,506 B2 | 3/2017 | Lockwood et al. |
| 9,687,634 B2 | 6/2017 | Grovender et al. |
| 9,764,118 B2 | 9/2017 | Anderson et al. |
| 9,993,613 B2 | 6/2018 | Wang et al. |
| 10,124,147 B2 | 11/2018 | Anderson et al. |
| 10,183,147 B2 | 1/2019 | Yang et al. |
| 2002/0165598 A1 | 11/2002 | Wahr et al. |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0092962 A1 | 5/2004 | Thornton et al. |
| 2004/0127927 A1 | 7/2004 | Adams |
| 2004/0236215 A1 | 11/2004 | Mihara et al. |
| 2005/0004523 A1 | 1/2005 | Osborne et al. |
| 2005/0015073 A1 | 1/2005 | Kataishi et al. |
| 2005/0096724 A1 | 5/2005 | Stenzel et al. |
| 2006/0069381 A1 | 3/2006 | Itou et al. |
| 2006/0089618 A1 * | 4/2006 | McFerran ......... A61M 25/0041 |
| | | | 604/525 |
| 2006/0100687 A1 * | 5/2006 | Fahey ....................... A61F 2/95 |
| | | | 623/1.11 |
| 2006/0155367 A1 | 7/2006 | Hines |
| 2007/0038292 A1 | 2/2007 | Danielpour |
| 2007/0260219 A1 | 11/2007 | Root et al. |
| 2008/0172008 A1 | 7/2008 | Root et al. |
| 2008/0188928 A1 * | 8/2008 | Salahieh ............ A61M 25/0054 |
| | | | 623/2.11 |
| 2009/0318881 A1 | 12/2009 | Shennib |
| 2010/0010475 A1 | 1/2010 | Teirstein |
| 2010/0160862 A1 * | 6/2010 | Howat ............... A61M 25/0012 |
| | | | 604/164.01 |
| 2010/0274158 A1 | 10/2010 | Teirstein |
| 2010/0331776 A1 | 12/2010 | Salahieh |
| 2012/0078232 A1 | 3/2012 | Schulting |
| 2013/0006167 A1 | 1/2013 | Alvarez et al. |
| 2013/0116701 A1 | 5/2013 | Wang et al. |
| 2013/0123912 A1 | 5/2013 | Tung et al. |
| 2013/0158653 A1 | 6/2013 | Gamarra et al. |
| 2013/0197483 A1 | 8/2013 | Anderson et al. |
| 2013/0239959 A1 | 9/2013 | Brain |
| 2013/0331782 A1 | 12/2013 | Grovender et al. |
| 2014/0012281 A1 | 1/2014 | Wang et al. |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0052097 A1 | 2/2014 | Petersen et al. |
| 2014/0058324 A1 | 2/2014 | Salahieh et al. |
| 2014/0081243 A1 | 3/2014 | Zhou |
| 2014/0171913 A1 | 6/2014 | Watanabe |

(56) References Cited

U.S. PATENT DOCUMENTS

| | | |
|---|---|---|
| 2014/0180122 A1 | 6/2014 | Stigall et al. |
| 2014/0276618 A1 | 9/2014 | Di Caprio |
| 2015/0051584 A1 | 2/2015 | Korkuch |
| 2015/0051633 A1 | 2/2015 | Sina |
| 2015/0133864 A1 | 5/2015 | Zachar et al. |
| 2015/0190617 A1 | 7/2015 | Anderson et al. |
| 2015/0297863 A1 | 10/2015 | Hannon et al. |
| 2015/0352329 A1 | 12/2015 | Watanabe |
| 2016/0051799 A1 | 2/2016 | Daniels et al. |
| 2016/0066933 A1 | 3/2016 | Root et al. |
| 2016/0074627 A1 | 3/2016 | Cottone |
| 2016/0101261 A1 | 4/2016 | Kugler |
| 2016/0101262 A1 | 4/2016 | Root et al. |
| 2016/0121080 A1 | 5/2016 | Cottone |
| 2016/0346502 A1 | 12/2016 | Fuller et al. |
| 2016/0346509 A1 | 12/2016 | Anderson et al. |
| 2016/0346515 A1 | 12/2016 | Buller et al. |
| 2016/0346946 A1 | 12/2016 | Kasen |
| 2017/0014598 A1 | 1/2017 | Stursa et al. |
| 2017/0080178 A1 | 3/2017 | O'Connell et al. |
| 2017/0106160 A1 | 4/2017 | Zachar |
| 2017/0143355 A1 | 5/2017 | Nicholson et al. |
| 2017/0156750 A1 | 6/2017 | Root et al. |
| 2017/0246423 A2 | 8/2017 | Cottone |
| 2017/0252043 A1 | 9/2017 | Fuller et al. |
| 2017/0354800 A1 | 12/2017 | O'Donovan |
| 2018/0092650 A1 | 4/2018 | Kugler |
| 2018/0093070 A1 | 4/2018 | Cottone |
| 2018/0104445 A1 | 4/2018 | Fuller et al. |
| 2018/0161547 A1 | 6/2018 | Brenizer et al. |

FOREIGN PATENT DOCUMENTS

| | | |
|---|---|---|
| EP | 2124816 | 9/2009 |
| EP | 2016969 | 4/2010 |
| EP | 2801385 | 11/2014 |
| EP | 3295983 | 3/2018 |
| JP | 2008-264118 | 5/2004 |
| JP | 2004275435 | 10/2004 |
| WO | 1996038193 | 12/1996 |
| WO | 97/37713 A1 | 10/1997 |
| WO | 2008064280 | 5/2008 |
| WO | 20140077881 | 5/2014 |
| WO | 2014141197 | 9/2014 |
| WO | 2016064753 | 4/2016 |

OTHER PUBLICATIONS

International Search Report and Written Opinion dated Feb. 4, 2016 corresponding to International Patent Application No. PCT/US2015/058969.
Boston Scientific Corporation and Boston Scientific Scimed, Inc. v. Vascular Solutions, Inc., IPR2014-00761, Petition (May 16, 2014).
European Search Report dated Aug. 23, 2018 corresponding to European Patent Application No. EP15858019; 12 pages.
Takahashi et al, "New Method to Increase a Backup Support of a 6 French Guiding Coronary Catheter", Catheterization and Cardiovascular Interventions 63:452-456 (2004).
Garcia-Blas et al, Usefulness and Safety of a Guide Catheter Extension System for the Percutaneous Treatment of Complex Coronary Lesions by a Transradial Approach, Med Prine Pract 2015; 24:171-177.
Vascular Solutions, Inc., v. Boston Scientific Corporation, 0:13-cv-01172-JRT-SER, Document 6 (D. Minn.) (May 28, 2013).
Boston Scientific Corporation and Boston Scientific Scimed, Inc. v. Vascular Solutions, Inc., IPR2014-00760, Petition (May 16, 2014).
Theodore R. Kucklick, "The Medical Device R&D Handbook," 2006; pp. 1-339.
Boston Scientific Corporation and Boston Scientific Scimed, Inc. v. Vascular Solutions, Inc., IPR2014-00762, Petition (May 16, 2014).
Boston Scientific Corporation and Boston Scientific Scimed, Inc. v. Vascular Solutions, Inc., IPR2014-00759, Petition (May 15, 2014).
QXMedical, LLC, v. Vascular Solutions, Inc., 0:17-cv-01969-PJS-TNL, Complaint (Jun. 8, 2017).
Boston Scientific Corporation and Boston Scientific Scimed, Inc. v. Vascular Solutions, Inc., IPR2014-00763, Corrected Petition (May 16, 2014).
U.S. Appl. No. 14/984,273, filed Dec. 30, 2015, a reissue of U.S. Pat. No. 8,292,850.
Introducing the Schneider Monorail-GEX Guidewire Exchange Catheter, Model No. K53-002, Monorail Piccolino Publication, Schneider (USA) Inc. 10/90 480112-1090.
International Search Report and Written Opinion dated Mar. 25, 2019 corresponding to International Patent Application PCT/US2019/013219, 21 pages.
QXMÉDICAL, LLC v. Vascular Solutions, LLC; Teleflex Innovations S.À.R.L.; and Arrow International, Inc., United States District Court District of Minnesota, Case No. 17-CV-1969 (PJS/TNL), dated Oct. 30, 2018.
Meads, et al., Coronary artery stents in the treatment of ischaemic heart disease: a rapid and systematic review, Health Technology Assessment 2000, 4 (23).
Excerpt from Grossman's Cardiac Catheterization, Angiography, and Intervention (6th edition), 2000, chapters 1, 4, 11 and 23-25.
Mehan, Coronary Angioplasty through 4 French Diagnostic Catheters, Catheterization and Cardiovascular Interventions, 1993, 30: 22-26.
Boston Scientific, Summary of Safety and Effectiveness Data, TAXUSTM Express2 Drug-Eluting Coronary Stent System (Mar. 4, 2004).
Schobel, Percutaneous Coronary interventions Using a New 5 French Guiding Catheter: Results of a Prospective Study, Catheterization & Cardiovascular Interventions, 2001, 53:308-312.
Cordis, Instructions for Use, CYPHER (Apr. 2003).
Medtronic, Summary of Safety and Effectiveness Data, DriverTM Coronary Stent System (Oct. 1, 2003).
Baim, Randomized Trial of a Distal Embolic Protection Device During Percutaneous Intervention of Saphenous Vein Aorto-Coronary Bypass Grafts, Circulation, 2002, 105: 1285-1290.
Bonzel, The sliding rail system (monorail): description of a new technique for intravascular instrumentation and its application to coronary angioplasty, Z. Kardio. 1987, 76: Supp. 6, 119-122.
Williams et al., Percutaneous Coronary Intervention in the Current Era Compared with 1985-1986, Circulation, 2000, 102:2945-2951.
Dorros et al., Coronary Angioplasty in Patients with Prior Coronary Artery Bypass Surgery, Cardiology Clinics 1989, 7(4): 791-803.
Excerpt from Kern's The Interventional Cardiac Catheterization Handbook (2nd edition) 2004, chapter 1.
Ozaki et al, New Stent Technologies, Progress in Cardiovascular Disease, 1996, 2:129-140.
Urban et al., Coronary stenting through 6 French Guiding Catheters, Catheterization and Cardiovascular Diagnosis (1993) 28:26-266.
Sakurada, Improved Performance of a New Thrombus Aspiration Catheter: Outcomes From In Vitro Experiments and a Case Presentation, Catheterization and Cardiovascular Interventions, 2004, 63: 299-306.
Nordenstrom, New Instruments for Catheterization and Angiocardiography, 1965.
Iserson, J.-F.-B. Charriere: The Man Behind the "French" Gauge, The Journal of Emergency Medicine. 1987, vol. 5, pp. 545-548.
Yokoyama, Feasibility and safety of thrombectomy with TVAC aspiration catheter system for patients with acute myocardial infarction, Heart Vessels (2006) 21: 1-7.
Terumo Heartrail II product literature (retrieved from Inter partes review of U.S. Pat. No. 8,048,032, Case No. IPR2020-00126 (Medtronic, Inc., and Medtronic Vascular, Inc. Petitioner, v. Teleflex Innovations S.À.R.L., Patent Owner, Nov. 12, 2019).
Medtronic Launcher product literature, 2003, 2002.
Metz, Comparison of 6f with 7f and 8f guiding catheters for elective coronary angioplasty: Results of a prospective, multicenter, randomized trial, American Heart Journal, 1997, vol. 134, No. 1, pp. 132-137.
Feldman, Coronary Angioplasty Using New 6 French Guiding Catheters, Catheterization and Cardiovascular Diagnosis, 1991, 23:93-99.

(56) References Cited

OTHER PUBLICATIONS

Limbruno, Mechanical Prevention of Distal Embolization During Primary Angioplasty, Circulation, 2003, 108: 171-176.

Petition for inter partes review of U.S. Pat. No. 8,048,032, Case No. IPR2020-00126 (*Medtronic, Inc., and Medtronic Vascular, Inc.* Petitioner, v. *Teleflex Innovations S.À.R.L.*, Patent Owner), Nov. 12, 2019.

Petition for inter partes review of U.S. Pat. No. 8,048,032, Case No. IPR2020-00127 (*Medtronic, Inc., and Medtronic Vascular, Inc.* Petitioner, v. *Teleflex Innovations S.À.R.L.*, Patent Owner), Nov. 12, 2019.

\* cited by examiner

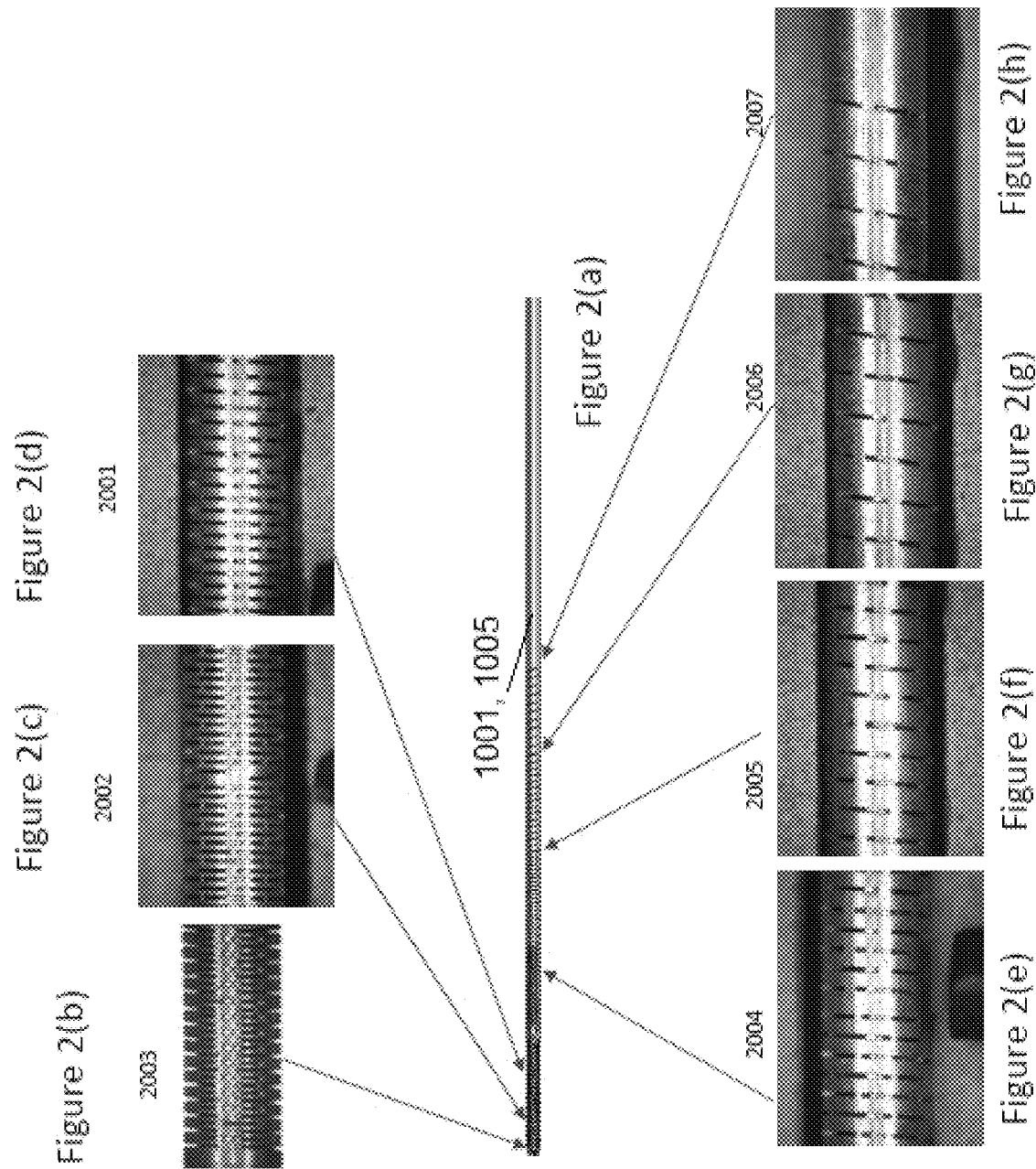

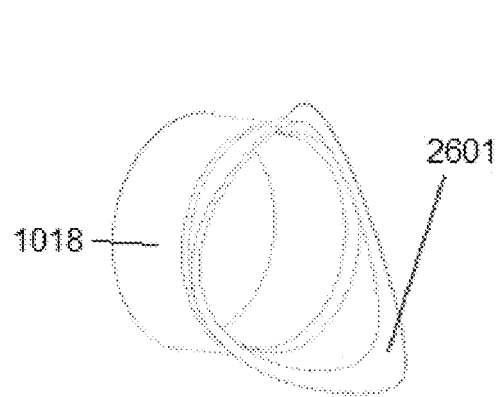
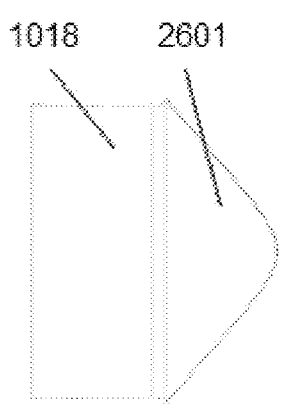
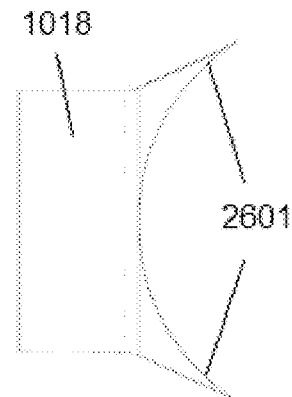
FIG. 25a     FIG. 25b     FIG. 25c
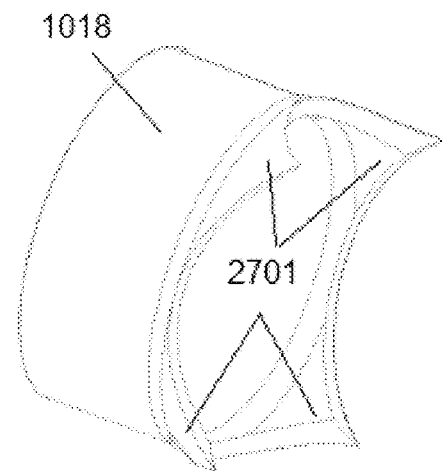
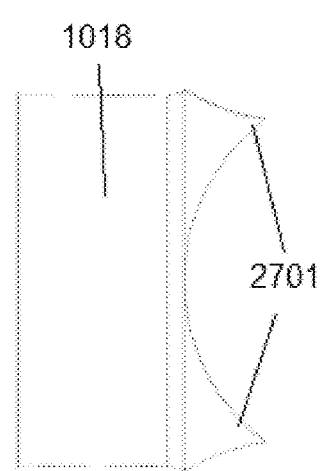
FIG. 26a     FIG. 26b
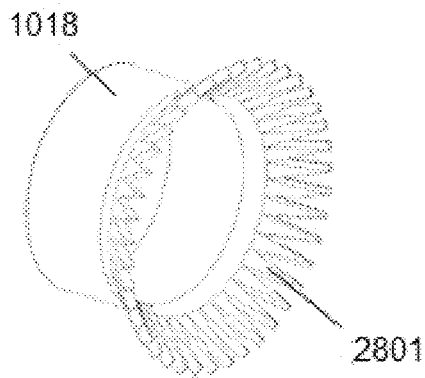
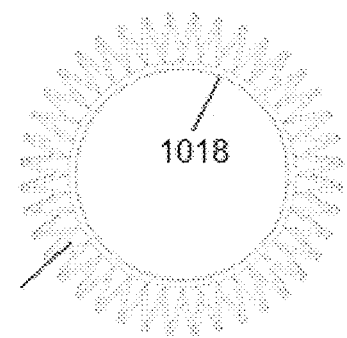
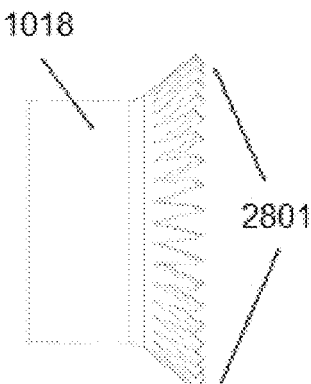
FIG. 27a     FIG. 27b     FIG. 27c

VARIABLE FLEXIBILITY CATHETER SUPPORT FRAME

CROSS-REFERENCE TO RELATED APPLICATIONS

This application is a continuation-in-part of U.S. patent application Ser. No. 15/726,024, filed Oct. 5, 2017, which application claims priority to U.S. Provisional Application No. 62/404,552, filed Oct. 5, 2016, the disclosures of which are incorporated by reference herein in their entirety. This application is also a continuation-in-part of U.S. patent application Ser. No. 15/522,216, filed Apr. 26, 2017, which application claims priority to PCT Application, PCT/US15/58969, filed Nov. 4, 2015, the disclosures of which are incorporated by reference herein in their entirety. The application claims priority to U.S. Patent Application Ser. No. 62/729,282 filed Sep. 10, 2018.

BACKGROUND

In coronary artery disease, the coronary arteries may be narrowed or occluded by atherosclerotic plaques or other lesions. These lesions may totally obstruct the lumen of the artery or may dramatically narrow the lumen of the artery. In order to diagnose and treat obstructive coronary artery disease, it is commonly necessary to pass a guidewire or other interventional instruments through and beyond the occlusion or stenosis of the coronary artery.

Percutaneous coronary intervention (PCI), also known as coronary angioplasty, is a therapeutic procedure used to treat the narrowed or stenotic section of the coronary artery of the heart due to coronary lesions or obstructions. A guide catheter may be used in PCI to support easier passage for another catheter or interventional device, such as, a microcatheter, stents or balloons, to access the target site. For example, the guide catheter can be inserted through the aorta and into the ostium of the coronary artery. Once seated in the opening or ostium of the coronary artery a guidewire or other instrument can be passed through the lumen of the guide catheter and then inserted into the artery distal to the occlusion or stenosis. Another example for the use of a guide catheter is found in femoro-popliteal intervention where femoral artery intervention can be effectively performed using radial or pedal access with guide catheters. Ruza et al. JAAC 11:1062 (2018).

However, guide catheters may encounter certain difficulties. The anatomy in the area for placement, e.g., the coronary vasculature, may be tortuous and the lesions themselves may be comparatively non-compliant. Moreover, when crossing comparatively non-compliant lesions, a backward force sufficient to dislodge the guide catheter from the ostium of the artery being treated can be generated. In order to improve backup support, U.S. RE 45,830 discloses a coaxial guide catheter which is adapted to be passable within a guide catheter. The distal portion of the coaxial guide catheter can be extended distally from the distal end of the guide catheter. The coaxial guide catheter includes a flexible tip portion defining a tubular structure having a lumen through which interventional cardiology devices such as stents and balloons can be inserted.

The guide catheter extension devices disclosed or available require construction of different tube portions of different characteristics and joining these tube portions together. For example, as disclosed in U.S. RE 45,830, the catheter extension includes a catheter tube portion which may include a soft tip, an inner liner component, a reinforced portion of the catheter body that is braided or coiled over the inner liner (flat or round wire braid composition or flat or round metal coil) and a polymeric cover section (e.g., Pebax, Nylon or other polymer material) which is melted or recovered over the reinforced catheter section, and a substantially rigid portion which may be made of stainless steel or nitinol tube. RE 46,116, RE45,760.

Another example of guide catheter design shows a guide catheter having a collar transition is made of a different material from the tubular portion. Here, the tubular portion is formed from multi-filament braided wire in order to reinforce the polymeric section. See, e.g., U.S. Pat. Nos. 8,048,032, 8,996,095, 9,352,123, 9,687,634, 9,764,118 and 9,993,613. However, these multicomponent designs and fabrication requirements can limit the mechanical properties and make fabrication complicated.

Thus, there remains a need for improved design for catheter bodies and catheter segments such as guide catheter extensions, and more generally, alternative designs for catheter tubes, that allow not only ease of fabrication, but also control of various characteristics of the tube, e.g., axial torque transmission, steerability, variable bending flexibility along the working length, pushability, collapse or kink resistance, etc., at any point along the tube. Controlling torqueability and flexibility at key points along the length of a catheter are important in order to enable the physician to negotiate access through various complex and often tortuous, anatomical vasculature which is often found in the coronary, peripheral or neurovascular systems.

SUMMARY OF THE INVENTION

The present disclosure provides a guide catheter extension, including: a push member having a lumen, a proximal end and a distal end; a tube frame defining a lumen therein, a longitudinal axis, and a proximal segment and a distal segment, wherein the tube frame comprises a plurality of cut patterns therein; and a tongue element extending from the proximal segment of the tube frame, wherein the tongue element is coupled to the push member. The push member may include a plurality of cut patterns therein. The push member may include a plurality of interrupted spiral cut patterns.

The cut patterns of the tube frame may include a plurality of interrupted spiral-cut patterns. The plurality of interrupted spiral-cut patterns may extend along a length of the tube frame having an average stiffness between 0.002-0.004 N/mm. The plurality of interrupted spiral-cut patterns may extend along a length of the tube frame having an average stiffness of 0.003 N/mm.

The cut patterns of the tube frame may include a continuous spiral-cut pattern. The continuous spiral-cut pattern may extend along a length of the tube frame having an average stiffness between 0.001-0.003 N/mm. The continuous spiral-cut pattern may extend along a length of the tube frame having an average stiffness of 0.002 N/mm.

The cut patterns of the tube frame may include a plurality of rings coupled together by a plurality of struts, wherein the rings are spaced apart from each other by a cut width, each ring having a width and each strut having a width and a length. The plurality of rings may extend along a length of the tube frame having an average stiffness between 0.005-0.016 N/mm N/mm. The rings may be oriented perpendicular to the longitudinal axis of the tube frame. The rings may be positioned at the distal segment of the tube frame. The plurality of struts can form at least one helical pattern in the distal segment of the tube frame. The plurality of struts may be aligned in at least one line that runs substantially parallel to the longitudinal axis of the tube frame. The struts may be positioned on every other pair of rings. The struts in adjacent rings may be angularly offset from one another at a radial angle ranging from about 5 degrees and about 180 degrees. A hypothetical plane formed by bisecting the tube frame at the proximal end of the tube frame may be perpendicular to the longitudinal axis of the tube frame.

The tube frame may include a plurality of protrusions which extend from the proximal end of the tube frame. The protrusions may terminate at a plurality of points that lie on a hypothetical plane that is perpendicular to the longitudinal axis of the tube frame. The protrusions can be coupled to a flare.

The cut patterns of the tube frame may include at least one zone along a portion of the length of the tube, the zone comprising a plurality of units, wherein the units of the zone are distributed circumferentially around the tube in at least one first band, each unit of the zone comprises at least one cutout segment that is oriented around a center of symmetry, wherein the center of symmetry of each unit in the band is positioned equally from the center of symmetry of an adjacent unit in the same band and the center of symmetry of each unit is positioned at the same point on the circumference of the tube as the center of symmetry of a second unit in a third band which is separated by one band from the first band; a skived collar transition section disposed adjacent the tube, the transition section having a tapered edge, a short end and a long end; and a push member attached at the long end of the transition section. The at least one zone can extend along a length of the tube frame having an average stiffness between 0.002-0.004 N/mm. The at least one zone may extend along a length of the tube frame having an average stiffness of 0.003 N/mm. Each unit comprises three cutout segments extending radially from a center of symmetry of the unit, wherein each cutout segment of the unit is positioned 120° degrees from the other cutout segments in the unit in the band.

The guide catheter extension may further include seven zones—a first zone, a second zone, a third zone, a fourth zone, a fifth zone, a sixth zone and a seventh zone, each zone having is formed from a plurality of units, wherein rank order of cutout surface area and cut-pattern perimeter length is: unit of the first zone<unit of the second zone<unit of the third zone<unit of the fourth zone<unit of the fifth zone<unit of the sixth zone<unit of the seventh zone. The zones may be arranged in sequence as first zone, second zone, third zone, fourth zone, fifth zone, sixth zone and seventh zone.

The cut patterns of the tube frame may include a single cut pattern. The cut patterns of the tube frame may include at least two cut patterns selected from the group consisting of continuous spirals, interrupted spirals, interconnected rings and zones or combinations thereof. At least one uncut segment of the tube frame can be disposed between two cut patterns. At least one uncut segment can be disposed along the tube frame.

At least a portion of the lumen of the tube frame may include a polymer liner bonded to the inner wall of the tube frame by at least one area of contact between the polymer liner and the inner wall along the length of the tube. The polymer liner can form a tube, and the tube may be positioned co-axially within the lumen of the tube frame. The polymer liner may include at least two polymer layers, wherein each polymer layer has a different glass transition temperature. The polymer layer adjacent to the inner wall of the tube frame may have a lower glass transition temperature (melt temperature) than the polymer layer adjacent to the lumen of the tube frame. The polymer liner can be bonded to the inner wall of the tube at a plurality of areas of contact between the polymer liner and the inner wall along the length of the tube. The polymer liner may be bonded continuously to the inner wall of the tube frame along the length of the tube. The areas of contact may be spaced apart from one another along the longitudinal axis of the tube by a distance ranging from about 1 mm to about 2.5 cm. The polymer liner may be bonded to the inner wall of the tube frame in a continuous helical pattern running along at least a portion of the length of tube frame. The polymer liner may be bonded to the inner wall of the tube frame by melting the polymer to the tube at selected areas of contact. The polymer liner may be bonded to the inner wall of the tube frame by an adhesive. The polymer layer adjacent to the inner wall of the tube can be a polyether block amide, and the polymer layer adjacent to the lumen of the tube frame can be polytetrafluoroethylene (PTFE). The polymer layer adjacent to the lumen of the tube frame may be coated with a lubricous material.

The tube frame can be covered by an outer jacket, and the outer jacket may be coated with a lubricious material.

The proximal segment of the tube frame may have a less axial flexibility than the distal segment of the tube frame.

The push member can have a cross-sectional width ranging from about 0.25 mm to about 2.5 mm. The push member may have a cross-sectional width ranging from about 0.25 mm to about 0.76 mm. The push member can be constructed from a hypotube having an inner lumen. The push member can define a substantially rectangular cross section along a length. The length of the tube frame can range from about 5 cm to about 150 cm, or alternatively, from about 50 cm to 100 cm.

The tube frame may include a plurality of protrusions which extend from the proximal end of the tube frame and/or a plurality of protrusions which extend from the distal end of the tube frame. The guide catheter extension may include a flare coupled to the protrusions on the proximal end of the tube frame, wherein the flare is constructed from a polymer. A catheter tip can be coupled to the protrusions on the distal end of the tube frame, wherein the catheter tip is constructed from a polymer. The polymer can be impregnated with a radiopaque material.

The tube frame can be constructed from nitinol or spring steel.

Two cuts may be positioned within the tube frame, on either side of the tongue element, each cut running substantially parallel with the longitudinal axis of the tube. Each of the cuts may terminate in the proximal segment of the tube frame at a keyhole.

The present disclosure provides a guide catheter extension, comprising: a push member having a proximal end and a distal end; and a tube frame coupled to the distal end of the push member, the tube frame defining a lumen, having a diameter sufficient to receive an interventional vascular device therethrough, an inner wall, wherein the tube frame includes a distal segment having a plurality of rings, wherein each of the rings are coupled to one another by a plurality of connection and a tongue extending from the proximal segment of the tube, wherein the tongue is coupled to the push member.

Connections between adjacent rings of the plurality of connections may be axially aligned. Connections between adjacent of the plurality of connections may be angularly offset from one another at an angle ranging from about 5 degrees and to about 180 degrees. The plurality of connections may form a helical pattern along the distal segment of the tube frame.

A polymer liner may be disposed within the lumen and extending through the plurality of interconnected rings. The polymer liner can include at least two polymer layers, wherein each polymer layer has a different glass transition temperature and wherein the polymer layer adjacent to the inner wall of the tube frame has a lower glass transition temperature (melt temperature) than the polymer layer adjacent to the lumen.

The guide catheter extension can include an outer polymer jacket covering at least a portion of the plurality of rings, wherein the outer polymer jacket is not fused to any portion of the plurality of rings.

The present disclosure provides a guide catheter extension, comprising: a push member having a proximal region and a distal region; and a tube frame coupled to the distal end of the push member, wherein the tube frame comprises: a tube frame defining a lumen therethrough having a diameter sufficient to receive an interventional cardiology device therethrough, wherein the tube frame has an average stiffness between approximately 0.03 N/mm and approximately 0.10 N/mm along a substantial length thereof. The tube frame is pushable through a curve having a radius of approximately 2.5 mm without kinking. The tube frame may have a wall thickness between approximately 0.0254 mm and approximately 0.254 mm. The tube frame may have a wall thickness between approximately 0.0635 mm and approximately 0.1143 mm.

The guide catheter extension may include a polymer liner at least partially disposed within the lumen of the tube frame, wherein the polymer liner is partially bonded to the tube frame. The polymer liner may have a wall thickness between approximately 0.00635 mm and approximately 0.127 mm. The polymer liner can be bonded to the tube frame at a plurality of discrete locations along the length of the tube, and wherein a width of each bond at each discrete location is between approximately 1 mm and approximately 2 mm.

The guide catheter extension can include a plurality of rings positioned in a distal region of the tube frame, wherein the width of each ring is between approximately 50 microns and approximately 200 microns. Each ring may be spaced from an adjacent ring between by approximately 10 microns and approximately 300 microns.

The guide catheter extension may include an outer polymer jacket covering at least a portion of the plurality of interconnected rings, wherein the outer polymer jacket is not fused to any portion of the plurality of interconnected rings, and wherein the outer polymer jacket has a wall thickness between approximately 5 microns and approximately 10 microns.

The guide catheter extension may include a tongue element extending from the proximal segment of the tube frame, wherein the tongue is coupled to the push member.

BRIEF DESCRIPTION OF THE DRAWINGS

FIG. 1b is a side view of the catheter of FIG. 1a.

FIG. 1c is a closer side view of a tube frame of the catheter of FIG. 1a.

FIGS. 2a-2h are examples of various cut patterns of a catheter constructed in accordance with the principles of the present disclosure.

FIG. 10b is an alternative perspective view of the distal tube of FIG. 10a.

FIG. 19b is an underside perspective view of the push member coupling of FIG. 19a.

FIG. 19c is a side view of the push member coupling of FIG. 19a.

FIG. 20b is an underside perspective view of the push member coupling of FIG. 20a.

FIG. 21b is an assembled view of the push member coupling of FIG. 21a.

FIGS. 25a-25c depict another example of a flare for a catheter constructed in accordance with the principles of the present disclosure.

FIGS. 26a-26b depict another example of a flare for a catheter constructed in accordance with the principles of the present disclosure.

FIGS. 27a-27c depict yet another example of a flare for a catheter constructed in accordance with the principles of the present disclosure.

DETAILED DESCRIPTION

Figure 1A:
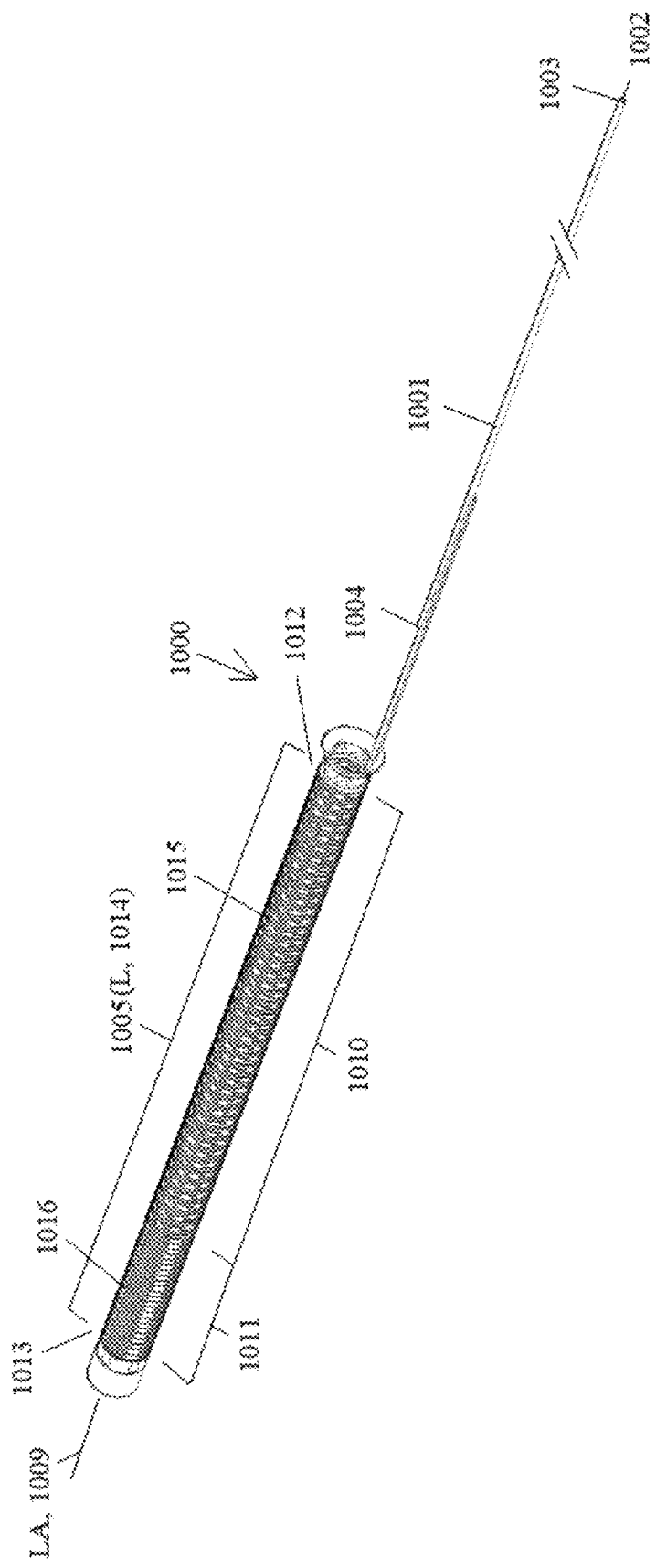
FIG. 1a is a perspective view of an example of a catheter constructed in accordance with the principles of the present disclosure.
Figure 1B:
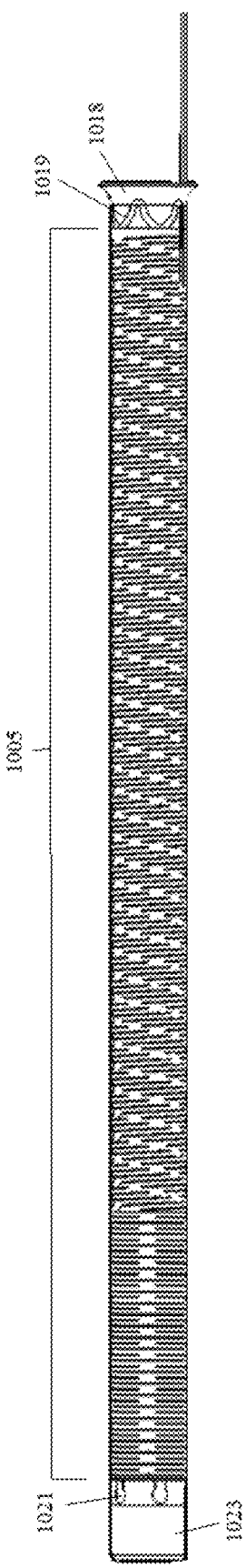
Figure 1C:
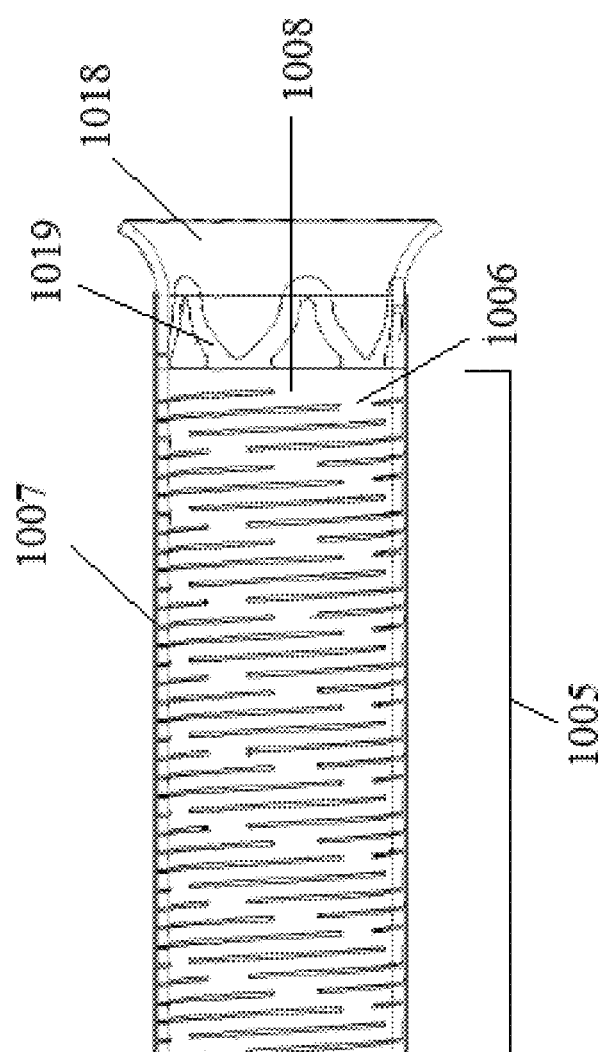

The present disclosure provides examples of guide catheter extension devices. Referring now to FIGS. 1a-c, an example of a guide catheter extension 1000 is shown. The guide catheter extension 1000 is sized and configured to pass through and extend distally from a guide catheter as described herein. The guide catheter extension 1000 generally includes a push member 1001 coupled to a distal tube frame 1005, and may have sufficient length such that, in use, a proximal region of the guide catheter extension 1000 is accessible or positioned exterior to a patient (such as at a proximal end or hub of a separate guide catheter), while a distal region of the guide catheter extension 1000 extends distally outward from an end of the guide catheter positioned within the anatomy of the patient.

The overall length of the guide catheter extension 1000 may vary depending upon the particular procedure or application being performed and/or a vasculature access point being utilized (e.g., whether introduced via a radial artery, femoral artery, contralateral access, or the like). For example, if the guide catheter extension 1000 is being used to access a coronary vessel, such as the right and left coronary arteries, the overall length of the guide catheter extension 1000 may be between approximately 110 cm (43.30 inches) and approximately 175 cm (68.89 inches). In a procedure involving access to a peripheral blood vessel, the overall length of the guide catheter extension 1000 may be between approximately 45 cm (17.72 inches) and approximately 300 cm (118.11 inches), with extended lengths being useful for procedures involving brachial or radial artery access points.

The push member 1001 can be made from one or more metallic materials (such as stainless steel), polymers, ceramics, and/or composites thereof providing sufficient axial loading or pushability to allow a user to move the guide catheter extension 1000 through an interior of a guide catheter without having the push member 1001 significantly bend, kink, or otherwise deform and potentially obstruct or damage the guide catheter, while also providing sufficient flexibility to allow the guide catheter extension 1000 to navigate various curves and bends of the vasculature while disposed within the guide catheter.

The push member 1001 may include, for example, one or more segments of hypotube, spiral-cut hypotube, multi-thread cable, interrupted-spiral cut tube, other cut geometries/configurations, or other elongated member(s), and may include one or more lumens 1002 therein and/or therethrough for the passage of one or more wires, devices, fluid delivery and/or aspiration features, or the like. Alternatively, the push member 1001 may be constructed without any lumens therein or therethrough.

The push member 1001 may include a small diameter or cross-sectional profile relative to an inner diameter or clearance of the guide catheter to reduce the amount of space within the guide catheter that the push member 1001 occupies, thereby allowing one or more other devices, instruments, or otherwise to pass through the guide catheter with minimal interference or obstruction. For example, the push member 1001 may have a diameter or cross-sectional width between approximately 0.254 mm (0.010 inches) and approximately 2.54 mm (0.100 inches) for use in a guide catheter having an inner diameter of 1.1016-30.48 mm (0.04-1.20 inches). In a preferred example, the push member 1001 may have a diameter or cross-sectional width between approximately 0.254 mm (0.010 inches) and approximately 0.762 mm (0.030 inches). The push member 1001 may have one or more cross-sectional shapes or profiles along its length, including but not limited to circular, hemi- or semi-circular, square, rectangular, triangular, and/or oval shapes or profiles. In addition and/or alternatively, the push member 1001 can comprise a plurality of cut patterns in one or more sections thereof.

The push member 1001 may define a proximal end 1003 and a distal end 1004, and may have an overall length constituting the majority of the length of the guide catheter extension 1000. The length of the push member 1001 may be sufficient to enter an incision or patient access point (which may include, for example, a hub, hemostatic valve, and the like), traverse the vasculature of the patient, and position the tube frame 1005 in proximity to a desired treatment site while a portion of the push member 1001 remains outside the patient and accessible/operable by a physician. The length may vary depending upon the particular procedure or application being performed and/or a vasculature access point being utilized (e.g., whether introduced via a radial artery, femoral artery, contralateral access, or the like). The push member and/or other proximal portion of the guide catheter extension 1000 may include a stop feature that prevents a physician from inserting the extension 1000 too far into the guide catheter. For example, the guide catheter extension 1000 may include a raised protrusion, weld, or other mass that exceeds a diameter or size of a guide catheter, hemostatic valve, and/or proximal device hub to mechanically prevent the over-insertion of the guide catheter extension 1000.

The tube frame 1005 includes or otherwise defines an outer wall 1007 and an inner wall 1006 enclosing a lumen 1008, a longitudinal axis LA 1009, a proximal segment 1010 and a distal segment 1011. The tube frame 1005 has a proximal end 1012 and a distal end 1013 and a length, L, 1014. The tube frame 1005 has a plurality of cut patterns 1015, 1016 (note, 1015 and 1016 represent only two possible embodiments of the various cut patterns that can be present in the tube frame). The tube frame 1005 has a tongue element 1017 extending from the proximal segment 1010 of the tube frame 1005, wherein the tongue element 1017 is coupled to the push member 1001. In certain embodiments, the tongue element 1017 extends from the proximal end 1012 of the proximal segment 1010.

Both the proximal end 1012 and the distal end 1013 of the tube frame 1005 can have protrusions 1019 and 1021, respectively. Flares or caps may be attached to the protrusions. This embodiment is shown in FIGS. 1*a-c* with the protrusions 1019 for the proximal end 1012, and the flare 1018 on the proximal end and the protrusions 1021 for the distal end 1013 with the tip 1023 attached to the protrusions 1021.

Figure 30:
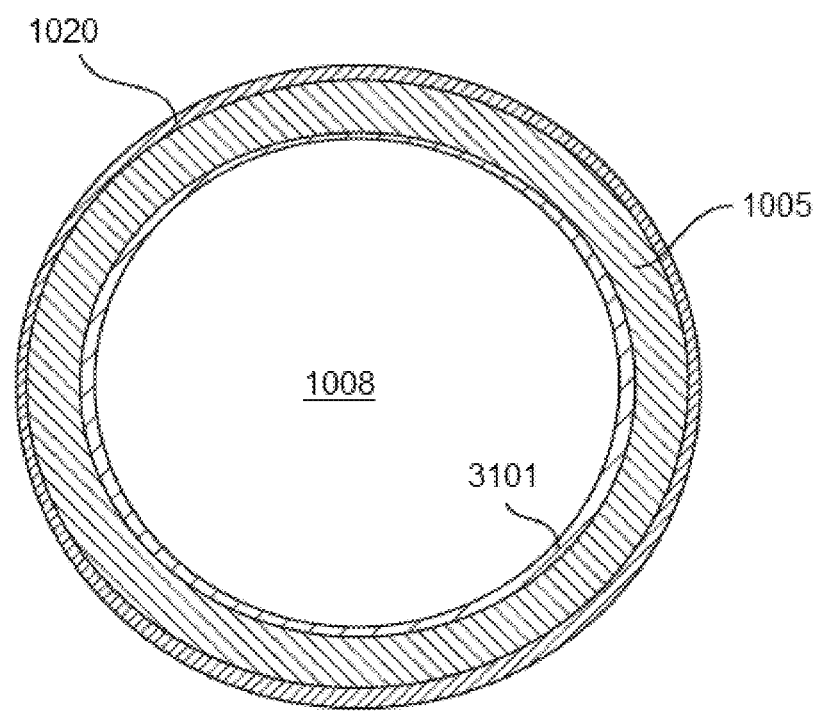
FIG. 30 is an example of a transverse cross-sectional view of the catheter of FIGS. 1a-c.

A portion of the tube frame 1005 can have a polymer liner 1022 and/or the outer wall 1007 of the tube frame 1005 can be covered (completely, partially, and/or intermittently) with an outer jacket 1020 (see, e.g., FIG. 30). The proximal end 1012 of the tube frame 1005, the ends of the protrusions 1019 at the proximal end 1012 of the tube frame 1005, and the flare 1018 are each oriented perpendicular to the longitudinal axis LA 1009 of a hypothetical plane bisecting the tube frame 1005.

The tube frame 1005 may be constructed from nitinol or stainless steel. For example, the tube frame can be made from metals, polymers, or a combination of polymers and metals. Examples of materials that may be used include stainless steel (SST), nickel titanium (Nitinol), or polymers. Preferred examples of other metals which may be used include, super elastic nickel titanium, shape memory nickel titanium, Ti—Ni, nickel titanium, approximately, 55-60 wt. % Ni, Ni—Ti—Hf, Ni—Ti—Pd, Ni—Mn—Ga, Stainless Steel (SST) of SAE grade in the 300 to 400 series e.g., 304, 316, 402, 440, MP35N, and 17-7 precipitation hardened (PH) stainless steel, other spring steel or other high tensile strength material or other biocompatible metal material. In one preferred embodiment, the material is superelastic or shape memory (e.g., nickel titanium), while in another preferred embodiment, the material is stainless steel.

The tube frame 1005 can include a superelastic alloy (generally referred to as "a shape-memory alloy") in its entirety, or in only in selected sections thereof. Examples of such superelastic alloys include: Elgiloy® and Phynox® spring alloys (Elgiloy® alloy is available from Carpenter Technology Corporation of Reading Pa.; Phynox® alloy is available from Metal Imphy of Imphy, France), SAE grade 316 stainless steel and MP35N (Nickel Cobalt) alloys which are available from Carpenter Technology corporation and Latrobe Steel Company of Latrobe, Pa., and superelastic Nitinol which is available from Shape Memory Applications of Santa Clara, Calif. U.S. Pat. No. 5,891,191.

Alternatively, the tube frame may be formed from polymers, e.g., include polyimide, PEEK, nylon, polyurethane, polyethylene terephthalate (PET), latex, HDHMWPE (high density, high molecular weight polyethylene) and thermoplastic elastomers or other polymers with similar mechanical properties.

The tube frame 1005 may be made by forming a pipe of a super elastic metal and then removing the parts of the pipe where the notches or holes are to be formed. The notches, holes or cuts can be formed in the pipe by laser (solid-state, femtosecond laser, or YAG laser, for example), electrical discharge (electrical discharge machining (EDM)), chemical etching, photo-etching mechanical cutting, or a combined use of any of these techniques. U.S. Pat. No. 5,879,381.

The overall length of the tube frame 1005 may vary depending upon the particular procedure or application being performed and/or a vasculature access point being utilized (e.g., whether introduced via a radial artery, femoral artery, contralateral access, or the like). For example, if the guide catheter extension 1000 is being used to access a coronary vessel, such as the radial or femoral arteries, the overall length of the tube frame 1005 may be between approximately 10.16 cm (4 inches) and approximately 33.02 cm (13 inches). In a procedure involving access to a peripheral blood vessel, the overall length of the tube frame 1005 may be between approximately 20.23 cm (8 inches) and approximately 91.44 cm (36 inches).

The tube frame 1005 may be sufficiently sized to receive interventional cardiology devices and/or instrumentation (such as, for example, treatment catheters, stent delivery and/or recovery devices, aspiration or occlusion treatment devices, etc.) therethrough, while also enabling the tube frame 1005 to pass through an inner diameter of the guide catheter.

The tube frame 1005 provides a combination of features contributing to the function, operability, and performance of the guide extension catheter. For example, the tube frame 1005 should provide a desired degree of structural integrity to prevent the lumen 1008 of the tube frame 1005 from collapsing during use. The tube frame 1005 also contributes to both the pushability and resistance to axial extension or compression under axial load, while also providing sufficient flexibility to navigate the contours of the anatomy both within and exterior to the guide catheter. To provide such features, the tube frame 1005 may be constructed from one or more metals, polymers, and/or composites thereof. In one embodiment, the tube frame 1005 may be constructed from nitinol or spring steel and may have a wall thickness ranging between approximately 0.0254 mm (0.001 inches) and approximately 0.254 mm (0.010 inches). In a preferred example, the tube frame 1005 may have a wall thickness ranging between approximately 0.0635 mm (0.0025 inches) and approximately 0.1143 mm (0.0045 inches).

Figure 3:
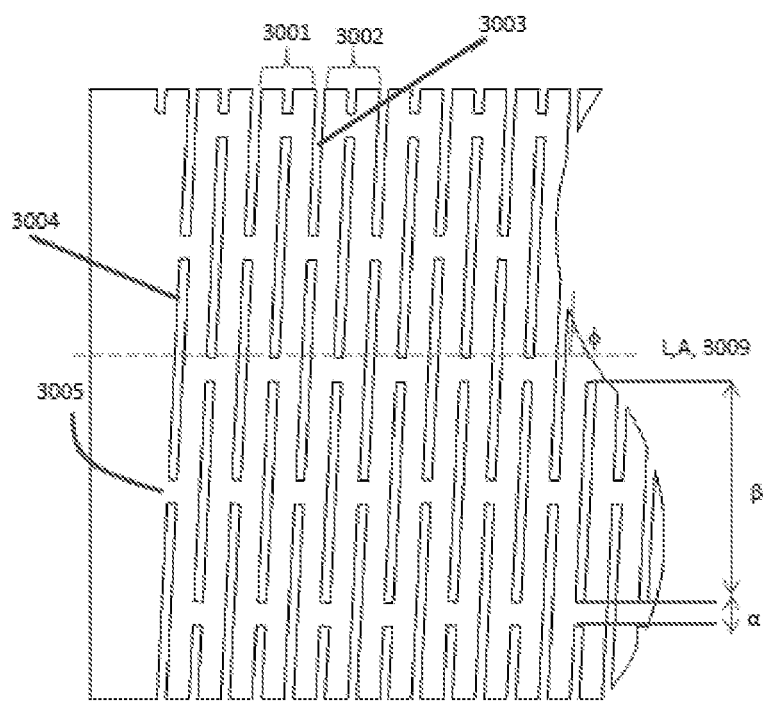
FIG. 3 is another example of a cut pattern of a catheter constructed in accordance with the principles of the present disclosure.

In one embodiment, the cut patterns of the tube frame 1005 can form a series or plurality of interrupted spiral cut patterns 15-18. FIGS. 2*a-h*. The various cut patterns can be distributed at any point along the length of the tube frame 1005. In another embodiment, the spiral cut path width includes alternating open or cut portions and uncut portions 2005-2007. The spiral pathway width is composed of alternating cut and uncut sections and is angled with respect to a circumference of the tubular portion (in other words, a pitch angle φ as shown in FIG. 3 of less than 90°). Such cut patterns may also be implemented into the push member 1001 to provide varying degrees of pushability, flexibility, and overall operability of the guide catheter extension 1000.

As illustrated in FIG. 3, each helically-oriented uncut portion has an arcuate extent "α" and each helically-oriented cut portion has an arcuate extent "β". Angles α and β can be expressed in degrees (where each complete helical turn is 360°). The uncut portions can be distributed such that adjacent uncut portions are not in axial alignment (or "staggered") with each other along a direction parallel to the longitudinal axis LA 3009. The uncut portions 3005 on every other turn of the interrupted spiral cut width can be axially aligned. The cut portions are shown as 3003 and 3004, while the spiral pattern is labeled 3001 and 3002. FIG. 3. The pitch angle φ and the distribution of continuous or interrupted spiral cut patterns can vary across the length, L 1014 of the tube frame 1005. The spiral-cut patterns of the tube frame 1005 can be formed from continuous spiral-cut sections, interrupted spiral-cut sections, or a hybrid of both types of spiral-cut patterns, where the various patterns can be arranged in any order on the tube frame 1005.

The spiral-cut sections provide for a graduated transition in bending flexibility, as measured by pushability, kink resistance, axial torque transmission for rotational response, and/or torque to failure. For example, the spiral-cut pattern may have a pitch that changes to increase flexibility in one or more areas of the tube frame 1005. The pitch of the spiral-cuts can be measured by the distance between points at the same radial position in two adjacent threads. In one embodiment, the pitch may increase as the spiral-cut progresses from a proximal position to the distal end of the catheter. In another embodiment, the pitch may decrease as the spiral-cut progresses from a proximal position on the catheter to the distal end of the catheter. In his case, the distal end of the catheter may be more flexible. By adjusting the pitch and the cut as well as the uncut path of the spiral-cuts, the pushability, kink resistance, torque, flexibility and compression resistance of the tube frame, may be controlled to meet user needs.

The spiral-cut patterns of the tube frame 1005 can be formed from continuous spiral-cut sections, interrupted spiral-cut sections, or a hybrid of both types of spiral-cut patterns, where the various patterns can be arranged in any order on the tube frame 1005. The interrupted cut spiral modules have the ability to maintain a concentric lumen area while in a bent configuration, even in sharp bends of small radii. The ability to maintain a concentric lumen of the tube frame 1005 enables smooth wire movement, in either direction within the tubular lumen, without resulting in a deformation of the lumen. Additionally, using superelastic materials such as Nitinol for the spiral cut segments, allows a segment to bend in tight curves through various vascular passageways without permanent lumen deformation.

The modulation of flexibility/rigidity across the length of the tube frame 1005 can be accomplished in a number of ways. For example, by varying the spiral-cut pattern variables (pitch, interruptions) and transitioning between spiral-cut patterns the flexibility/rigidity of a tube may be controlled. In addition, the spiral-cut pattern allows the cross-sectional diameter of the lumen to be maintained when the tube frame 1005 is bent or curved. Spiral-cut sections having different cut patterns may be distributed along the length of the tube. The spiral-cut patterns may be continuous or discontinuous along the length of the module. For example, there may be 1, 2, 3, 4, 5, 6, 7, . . . n spiral-cut sections along the length of the tube frame. The spiral-cut sections may be continuous or interrupted. Within each section a constant cut pattern may be present, but across different sections within a tube frame, the cut patterns may vary, e.g., in terms of pitch. Each section may also contain a variable pitch pattern within the particular section. Each spiral-cut section may have a constant pitch, e.g., in the range of from about 0.05 mm to about 10 mm, e.g., 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, 2.5 mm, 3.0 mm, 3.5 mm, 4.0 mm, etc. The pitch may also vary within each section. The pitches for different spiral-cut sections may be same or different. The orientation or handedness of spiral-cut sections may also vary within the spiral-cut sections. The width of the spiral cuts can vary, e.g., from about 1 micron to about 100 microns.

For an interrupted spiral-cut section, the interrupted spiral pattern can be designed such that each turn or rotation of the spiral includes a specific number of cuts, Nc (e.g., 1.5, 2.5, 3.5, 4.5, 5.5, etc.). Nc can also be whole numbers, such as 2, 3, 4, 5, . . . n, as well as other real numbers, such as 2.2, 2.4, 2.7, 3.1, 3.3, etc. At a given Nc, the uncut extent α and the cut extent β can be chosen as α=(360−(β*Nc))/Nc such that each rotation has Nc number of repeat patterns each comprising a cut portion of extent β adjacent an uncut portion of extent α. For example, at Nc=1.5, 2.5, and 3.5, the following table shows example choices of various embodiments for α and β.

TABLE I

| Nc α and β values | | | | | |
|---|---|---|---|---|---|
| Nc = 1.5 | | Nc = 2.5 | | Nc = 3.5 | |
| β (°) | α (°) | β (°) | α (°) | β (°) | α (°) |
| 230 | 10 | 140 | 4 | 90 | 12.13 |
| 229 | 11 | 139 | 5 | 89 | 13.13 |
| 228 | 12 | 138 | 6 | 88 | 14.13 |
| 227 | 13 | 137 | 7 | 87 | 15.13 |
| 226 | 14 | 136 | 8 | 86 | 16.13 |
| 225 | 15 | 135 | 9 | 85 | 17.13 |
| 224 | 16 | 134 | 10 | 84 | 18.13 |
| 223 | 17 | 133 | 11 | 83 | 19.13 |
| 222 | 18 | 132 | 12 | 82 | 20.13 |
| 221 | 19 | 131 | 13 | 81 | 21.13 |
| 220 | 20 | 140 | 14 | 80 | 22.13 |
| 219 | 21 | 129 | 15 | 79 | 23.13 |
| 218 | 22 | 128 | 16 | 78 | 24.13 |
| 217 | 23 | 127 | 17 | 77 | 25.13 |
| 216 | 24 | 126 | 18 | 76 | 26.13 |
| 215 | 25 | 125 | 19 | 75 | 27.13 |
| 214 | 26 | 124 | 20 | 74 | 28.13 |
| 213 | 27 | 123 | 21 | 73 | 29.13 |
| 212 | 28 | 122 | 22 | 72 | 30.13 |
| 211 | 29 | 121 | 23 | 71 | 31.13 |
| 210 | 30 | 120 | 24 | 70 | 32.13 |
| 209 | 31 | 119 | 25 | 69 | 33.13 |
| 208 | 32 | 118 | 26 | 68 | 34.13 |
| 207 | 33 | 117 | 27 | 67 | 35.13 |
| 206 | 34 | 116 | 28 | 66 | 36.13 |
| 205 | 35 | 115 | 29 | 65 | 37.13 |

Figure 4A:
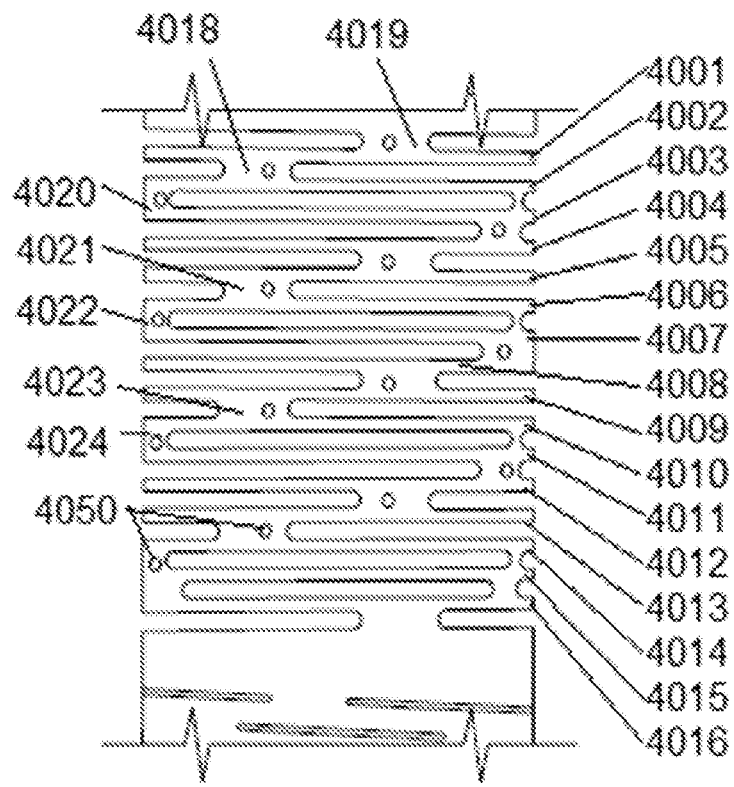
FIGS. 4a-4b depict examples of interconnected ring segments constructed in accordance with the principles of the present disclosure.

In another embodiment, the cut patterns of the tube frame 1005 comprise a plurality of rings 4001-4016 coupled together by a plurality of connections 4018-4024, where the rings 4001-4017 are spaced apart from each other by a cut width 4025-4030 (labeled only for illustration purposes). FIG. 4a. The rings are also referred to as "interconnected rings". The interconnected rings may include one or more radiopaque markers 4050 or other visualization feature that can be viewed through one or more medical imaging modality during a procedure (e.g., fluoroscopy, radiography, etc.). Such radiopaque points along the length of the plurality of rings and/or tube frame 1005 could be applied by inserting insert one or more radiopaque marker dots or rivets; through mask coating such as plating or vapor deposition of gold or platinum at designated locations; placement of one or more marker rings or bands of material around the tube frame 1005, which may be coaxially fixed as described herein. In addition and/or alternatively, one or more polymer layers may be applied to portions of the plurality of rings and/or tube frame 1005 with radiopaque materials and/or segments embedded therein.

Figure 4B:
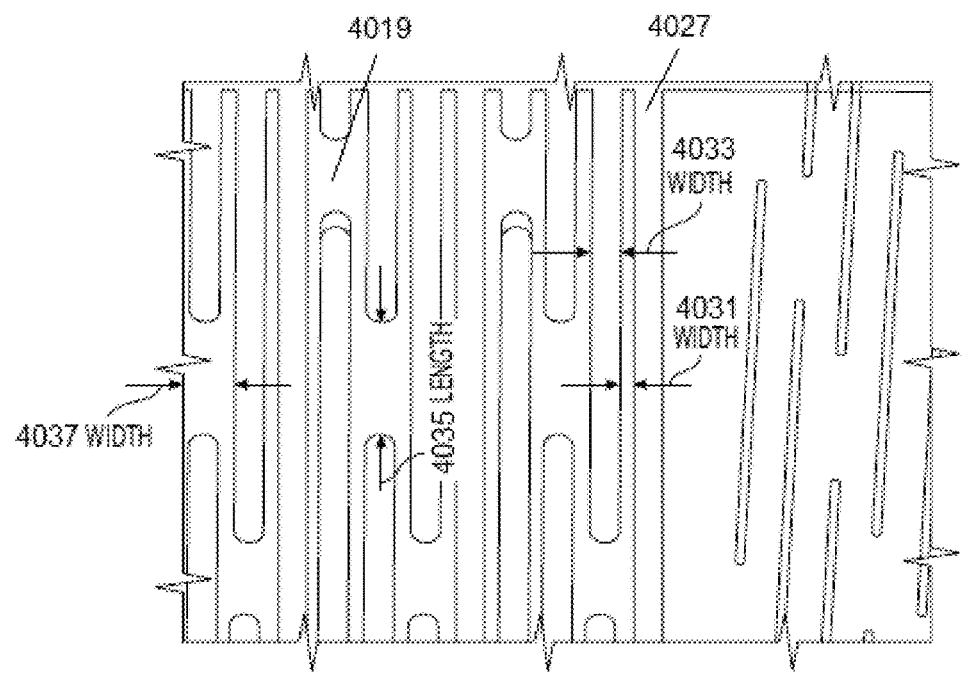

The dimensions of the rings are illustrated as follows. Each ring has a width 4031. Each ring is spaced from an adjacent ring by a cut width 4033. Each connection 4018-4024 or strut has a length 4035 and width 4037. FIG. 4b. Each of these parameters can vary across a plurality of rings. The pathway around the tube frame 1005 between any two pair of rings, e.g., 4001/4002, 4002/4003, 4003/4004, 4004/4005, etc., is formed from alternating cut section 4027 and uncut sections 4019 (also referred to herein as the connection or strut), each having a set arc length. FIG. 4b. The dimensions of the cut width, height of the rings, width and length of the struts can be adjusted to achieve any desired flexibility or stiffness of the tube frame 1005.

Figure 5:
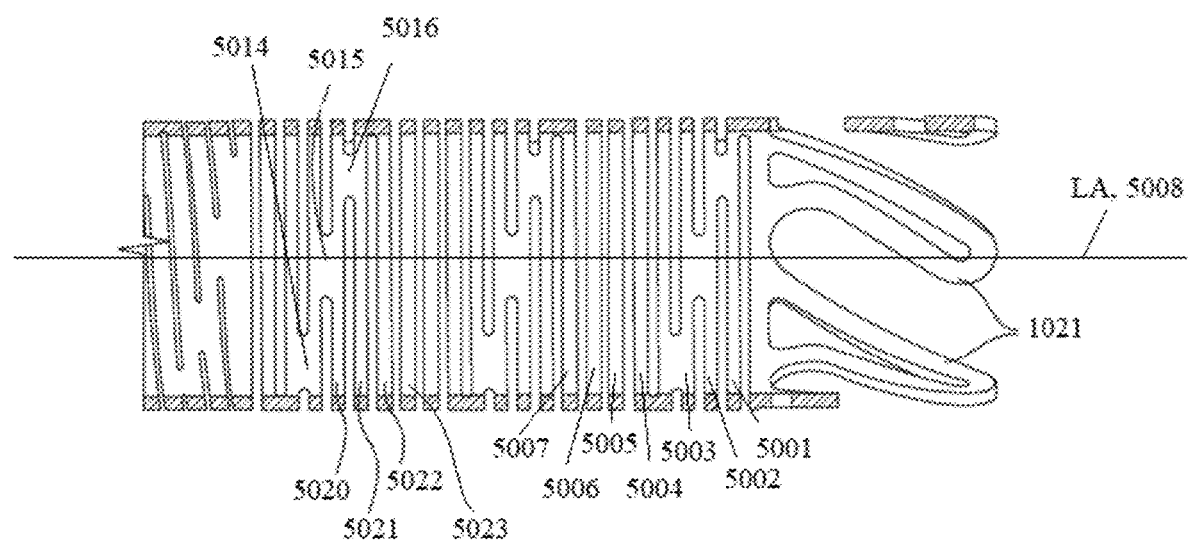
FIG. 5 depicts an example of a distal region of a catheter constructed in accordance with the principles of the present disclosure.

The rings 5001-5007 (selected rings labeled herein only for illustration purposes) can be oriented perpendicular (or substantially perpendicular) to the longitudinal axis LA 5008 of the tube frame 5009 and, in a preferred embodiment, the plurality of rings 5001-5007 can be positioned at the distal segment 1011 of the tube frame 1005. FIG. 5. However, the rings can be positioned anywhere along the length L (1014) of the tube frame 1005.

In certain embodiments, the struts 5014-5016 can form a helical pattern over the length of the section of the tube frame having the rings. FIG. 5. In this embodiment, the struts 5014-5016 are distributed on every adjacent ring, e.g., 5020/5021, 5021/5022 and 5022/5023. The struts on adjacent rings, e.g., 5020/5021, 5021/5022 and 5022/5023, can be angularly offset from each other at an angle ranging from about 5 degrees to about 180 degrees (5, 10, 15, 30, 45, 60, 90 and 180 degrees).

Figure 6A:
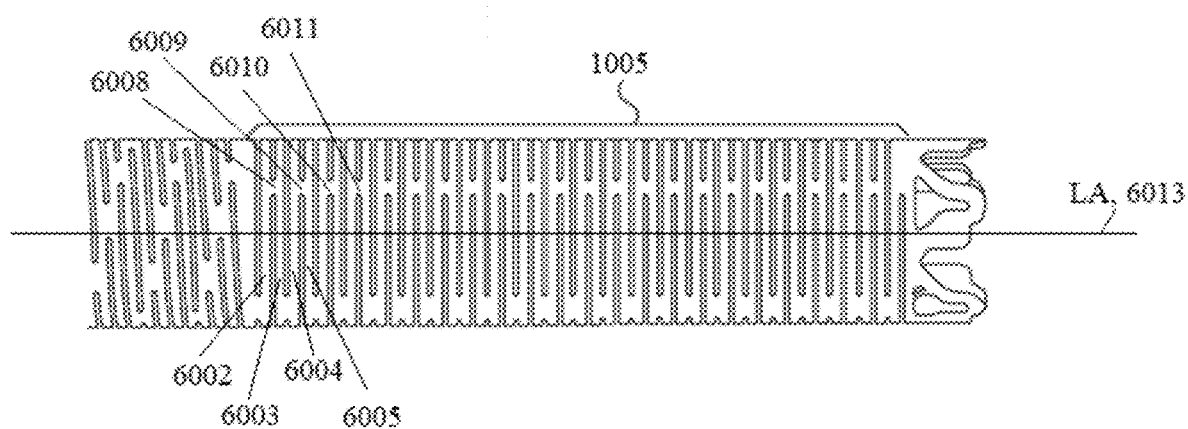
FIG. 6a depicts an example of a distal region of a catheter constructed in accordance with the principles of the present disclosure.
Figure 6B:
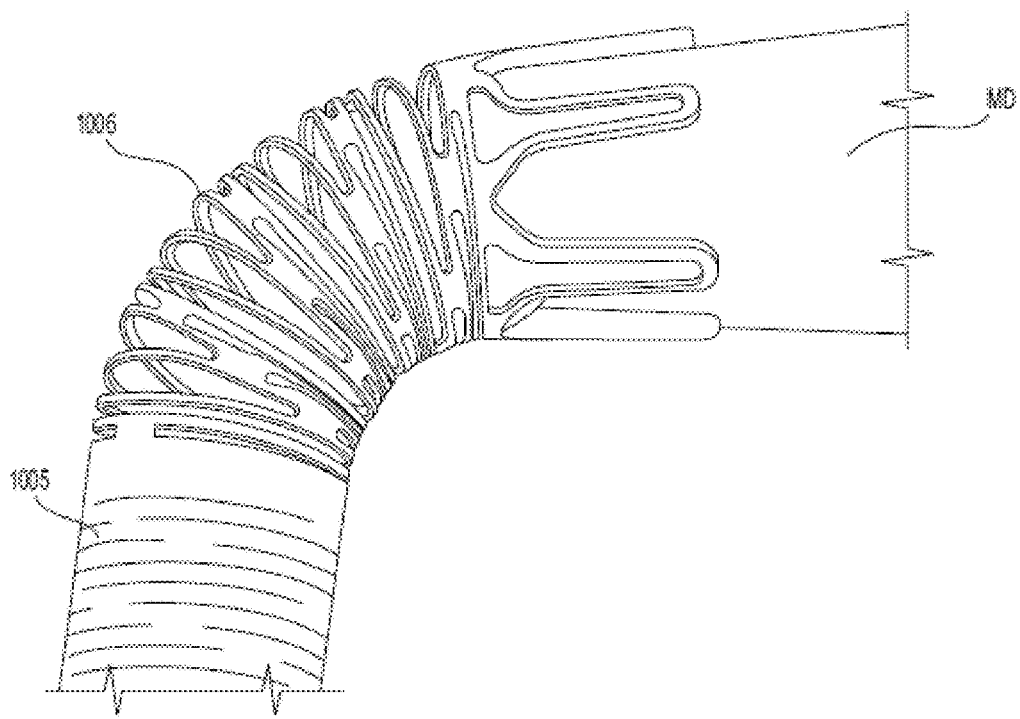
FIGS. 6b-6c illustrate examples of the flexibility characteristics of a catheter constructed in accordance with the principles of the present disclosure.

Alternatively, the struts 6008-6011 (FIG. 6a) can be linearly aligned parallel to the longitudinal axis LA 6013 of the tube frame 1005. In the embodiment shown in FIG. 6, the struts 6008-6011 are spaced on every other pair of rings. For example, rings 6002 and 6003 are connected by struts 6008 and rings 6004 and 6005 are connected by strut 6009, but there is no strut at the same radial position between rings 6003 and 6004.

Figure 6C:
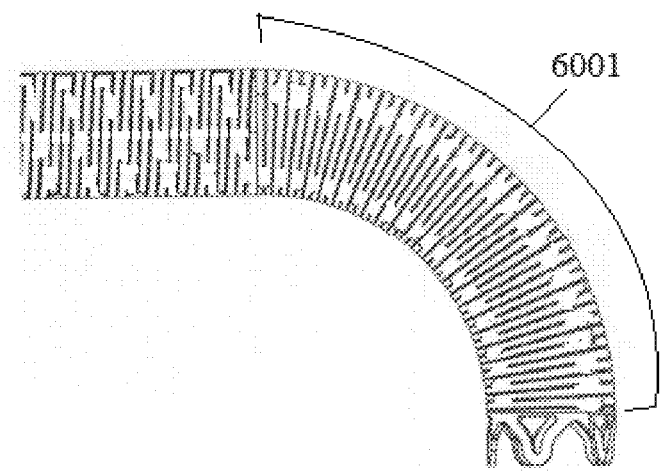

The plurality of rings 6001 (FIG. 6b) provide increased flexibility allowing the distal segment 1011 of the tube frame 1005 containing the rings 6001 to navigate curves having radii as small as approximately 2.54 mm (0.1 inches). For example, the distal segment containing the rings 6001 can bend at a 90-degree angle without compromising or collapsing the lumen 1008 of the rings 6001 or of the tube frame 1005, consequently avoiding kinking the guide catheter extension during use in increasingly smaller anatomy or vessels. FIG. 6c. Although as illustrated here, the rings are distributed only over a portion of the of the tube frame 1005, in other embodiments, the rings can be distributed over a substantial majority or entire length of the tube frame 1005.

The number of struts between any two rings can vary from 1-10 with 1 or 2 being the preferred number of connections. In other examples, the numbers of struts may exceed two, but the dimension of the struts may be modified to maintain the desired degree of flexibility of the guide catheter extension. The angular offset of the struts, the spacing of the rings, and/or the height of each ring may be varied in conjunction with the overall length of the plurality of the rings to provide the desired degree of flexibility and pushability of the guide catheter extension through smaller vessels.

Figure 7:
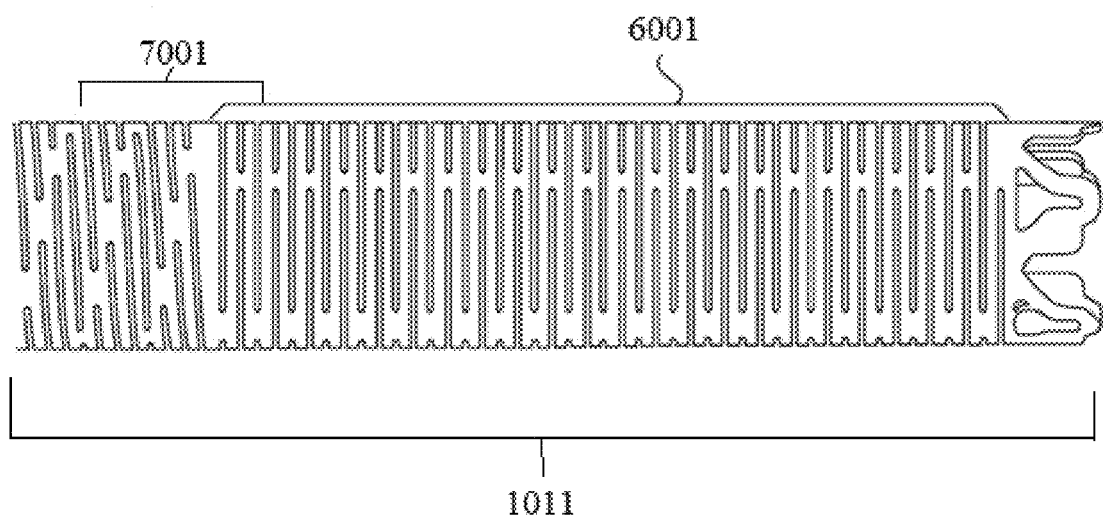
FIG. 7 depicts an example of a distal region of a catheter constructed in accordance with the principles of the present disclosure.

Because of the increased flexibility of the rings as compared to the flexibility of either the proximal segments 1010 of the tube frame 1005 or other portions of the distal segment 1011, the distal segment 1011 may define or otherwise include a transition zone of intermediate flexibility 7001 leading to the plurality of rings 6001 (FIG. 7). For example, the transition zone 7001 may include cut pattern variations (such as, for example, cut widths, angular orientations, pitch angles, etc.) as compared to that of more proximal sections of the distal segment 1011 in order to provide a flexibility or average stiffness that lies between an average stiffness of a proximal region of the distal segment and an average stiffness of the rings. The transitional flexibility improves the ability of the guide catheter extension to navigate tortuous anatomy without compromising or kinking the internal lumen, which could otherwise occur with abrupt significant changes in stiffness across distal sections of the guide catheter extension.

Figure 8A:
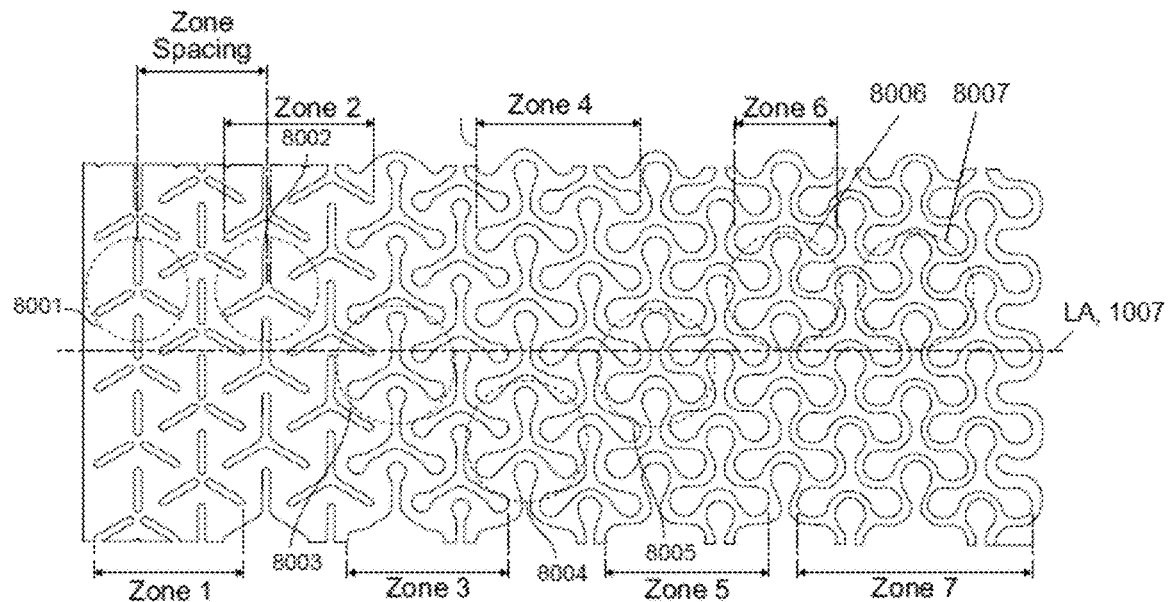
FIGS. 8a-8c illustrate examples of cut patterns for a catheter constructed in accordance with the principles of the present disclosure.
Figure 8B:
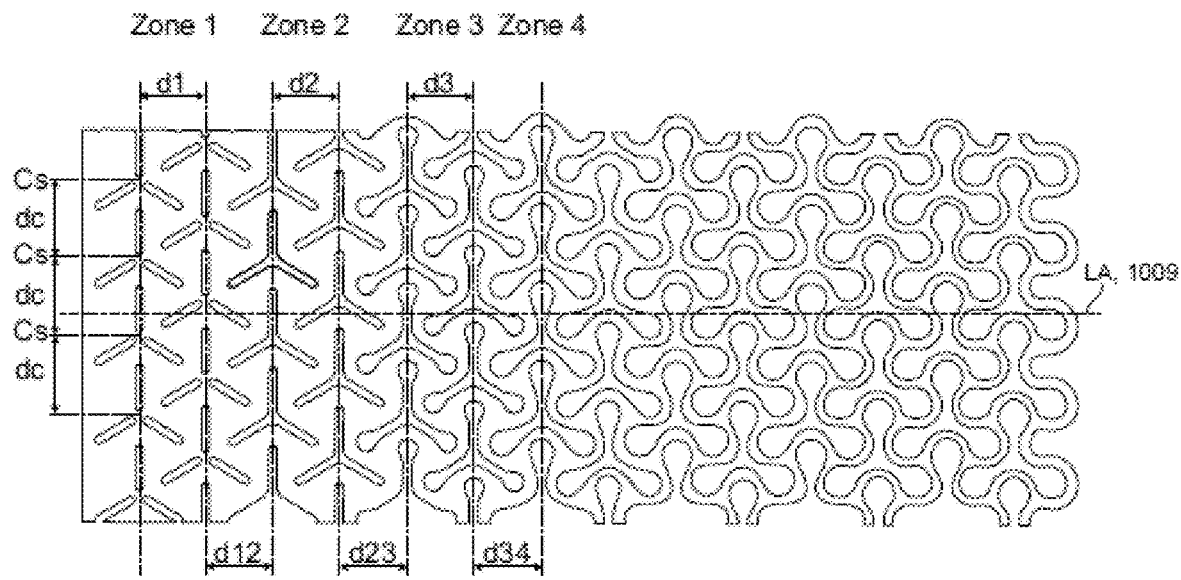
Figure 8C:
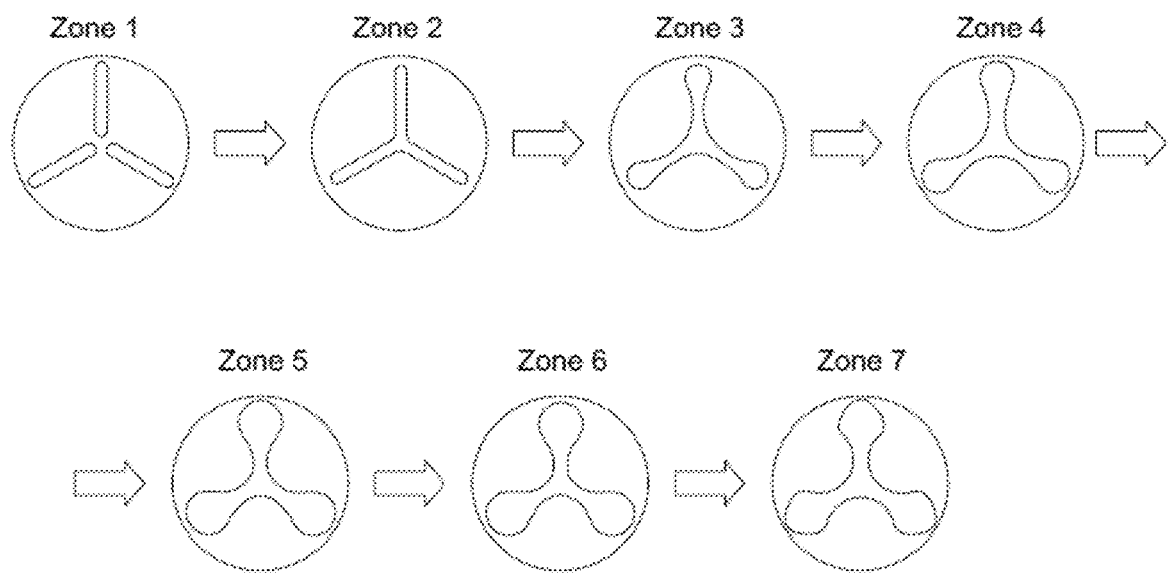

Another embodiment of the tube frame 1005 cut patterns of the disclosure is shown in FIGS. 8a-c. The zones can be along any portion of the tube frame, e.g., in the proximal 1010 or distal 1011 segments, in a single or multiple segment and may comprise the cut pattern of the entire tube frame 1005. Each zone includes a plurality of units (or groups) of radially symmetric, cutout segments that are distributed around the circumference of the tube in a band or row. A band or row can have 2, 3, 4, 5, 6, 7, 8, 9, 10, 20, 30, 40, 50, 60, 70, 80, 90, 100, 200, 300, 400, 500, 1000 to n units. In FIG. 8a, seven zones, Zones 1-7 are shown. Units from each of the 7 zones are identified as follows: (i) Zone 1, 8001; (ii) Zone 2, 8002; (iii) Zone 3, 8003; (iv) Zone 4, 8004; (v) Zone 5, 8005; (vi) Zone 6, 8006; and (vii) Zone 7, 8007. Each unit of the cutout portions can include three cutout segments each segment extending radially from a center point or center of symmetry. The cutout segments have a three-fold rotational symmetry, where each cutout segment is rotated 120 degrees from an adjacent cutout segment about a center of symmetry. Within each zone, all of the units of cutout segments may have an equal open surface area (i.e., the open surface area is the area enclosed by the contour of the segments in a contiguous manner) as well as an equal cut-pattern perimeter length, the length of a continuous line traced along the shape of the cutout segment. Across different zones, the units of cutout segments may have larger surface areas and increased cut-pattern perimeter length in zones when labeled in the figure with higher zone numbers, e.g., the open surface area ranking unit of zone 1<unit of zone 2<unit of zone 3<unit of zone 4<unit of zone 5<unit of zone 6<unit of zone 7 and the cut-pattern perimeter length ranking is unit of zone 1<unit of zone 2<unit of zone 3<unit of zone 4<unit of zone 5<unit of zone 6<unit of zone 7. The patterns of the cutout portions having the three-fold rotational symmetry about a central point of symmetry (center of symmetry) as shown can also generally referred to as the "triplex" pattern or "triplex" cut herein.

The configuration shown provides for a gradually decreasing uncut surface area coverage along the length of the tube from the Zone 1 to Zone 7, enabling the segment of the tube shown in this embodiment to have a gradually increasing bending flexibility. The 7 zones in FIG. 8 are shown arranged in sequence, i.e., 1 to 7, only for illustrative purpose. In other embodiments, the zones containing the units can be arranged in any order along the longitudinal axis to provide any desired change of bending flexibility at any point or section along the longitudinal axis. The tube can be provided with fewer, 1, 2, 3, 4, 5 or 6, or more zones, 7, 8, 9, 10, 11, 12, 13, 14 or 15 (higher numbers are also possible, e.g. 20, 30, 40, 50, 60, 70, 80, 90, 100, 200, 300, 400, 500, 600, 700, 800, 900, 1000 to n different zones). The zones, which have different cutout surface areas as well as different cut-pattern perimeter lengths, can also be arranged in any order, e.g., zone 1, zone 6, zone 7, zone 4, zone 5, zone 3, zone 2, in order to control flexibility of the tube at any point along the length of the tube.

The spacing between units in a band is shown in FIG. 8*b* and is represented as dc, where dc is the distance between the center of symmetry, Cs, of two adjacent units in the same band. The spacing, dc, is equal within a single band and may be constant across the length of the tube in different zones. The spacing between bands within a zone, e.g., zone 1, zone 2 and zone 3, is shown as d1, d2 and d3; d1=d2=d3, where the spacing is measured between the lines, which run through the center of symmetry, Cs, of the bands within each zone. The spacing between zones, e.g., zone 1-zone 2, d12, zone 2-zone 3, d23 and zone 3-zone 4, d34; d12=d23=d34, where the spacing is measured between the lines, 81-86. In one embodiment, the spacing between bands within a zone may be equal to the spacing of two bands between two different zones, e.g., d1=d2=d3=d12=d23=d34. In other embodiments, the spacing between bands within a zone may be greater than or less than the spacing between the bands in two different zones, e.g., d1=d2=d3>d12=d23=d34 or d1=d2=d3<d12=d23=d34.

All cutout segments of the units within a zone can have the same orientation or are in-phase with respect to the line through the center of symmetry for each row. The cutout segments in adjacent bands or rows within a zone can also have the same orientation or are in-phase with respect to the line through the center of symmetry for each row. In other words, the corresponding cutout segments in one unit within a zone are parallel with the cutout segments in an adjacent unit. The center of symmetry, Cs, of units within the same zone, but in adjacent bands is shifted by one unit as shown in An overview of the transition of the units across zone 1 to zone 7 is shown in FIG. 8*c*. The following characteristics apply to the dimensions across the zones. The open surface area of the cutout areas across the different zones rank orders as: Zone 1<Zone 2<Zone 3<Zone 4<Zone 5<Zone 6<Zone 7. The change in either open surface area or cut-pattern perimeter length across multiple zones can be linear, exponential, assume a step-wise or square wave function and be increasing, decreasing, constant, continuous or discontinuous.

Within any one zone, the cutout segments forming a unit may assume any symmetrical shape about a center of symmetry, Cs. There may be 1, 2, 3, 4, 5, 6, 7, 8, 9, 10 or n cutout segments in a unit. The cutout segments may be continuous or separate. For example, the cutout segment may form a circle or a symmetrical, n-sided polygon, such as a hexagon or octagon. Different zones may have the same or different symmetrical shapes. The geometric rules, both within a zone as well as across a zone remain the same in these embodiments as they are for the triplex cutout segments described above. Specifically, the units are arranged in a band. A band or row can have 2, 3, 4, 5, 6, 7, 8, 9, 10, 20, 30, 40, 50, 60, 70, 80, 90, 100, 200, 300, 400, 500, 1000 to n units. The spacing between units in a band represented as dc, where dc is the distance between the center of symmetry, Cs, of two adjacent units in a band, dc, is equal within a single band and may be constant across the length of the tube in different zones. The spacing between bands within a zone and across zones may be equal as well. All cutout segments of the units within a zone can have the same orientation or are in-phase with respect to the line through the center of symmetry for each row or band. The cutout segments in adjacent bands or rows within a zone can also have the same orientation or are in-phase with respect to the line through the center of symmetry for each row. The center of symmetry, Cs, of units within the same zone, but in adjacent bands is shifted. Between two adjacent zones, the units are shifted around the circumference of the band such that a straight line can be drawn between the center of symmetry for units in adjacent zones. The center of symmetry, Cs, in different bands falls along the same line in every other band. In other words, the center of symmetry of each unit is positioned at the same point on the circumference of the tube frame as the center of symmetry of a second unit in a third, third, fifth, etc. band which is separated by one band from the first band.

One tube frame 1005 may contain multiple, different zones. For example, the tube can be provided with 1, 2, 3, 4, 5, 6, 7, 8, 9, 10, 11, 12, 13, 14 or 15 (higher numbers are also possible, e.g. 20, 30, 40, 50, 60, 70, 80, 90, 100, 200, 300, 400, 500, 600, 700, 800, 900, 1000 to n different zones). If a tube frame 5 contains multiple zones, then across different zones there may be a change in open surface area and cut-pattern perimeter length. For example, if the cutout segment is formed in the shape of a hexagon and there are seven zones, a first zone, a second zone, a third zone, a fourth zone, a fifth zone, a sixth zone and a seventh zone, then the rank order for the open surface area and cut-pattern perimeter length is: unit of first zone<unit of second zone<unit of third zone<unit of fourth zone<unit of fifth zone<unit sixth zone. If there are equal number of units per zone, then the rank order applies to zones as well. The change in either open surface area or cut-pattern perimeter length across multiple different zones can be linear, exponential or assume a step-wise or square wave function and be increasing, decreasing, constant, continuous or discontinuous.

In embodiments formed from other cutout segments, e.g., circles or n-sided polygons, the width across any uncut portion, may be varied, i.e., the width may be reduced. This reduction in width will result in an increase in the open surface area 1004. By increasing the open surface area, the uncut surface area within unit in any one zone, the flexibility of that portion composed of such units with increased open surface area of the cutout segments will increase.

The flexibility of the tube frame 1005 may be controlled at any position along the tube frame 1005 by combining one or more zones at various positions along the length of the tube. Flexibility of the tube frame 1005 is positively correlated with the open surface area. In other words, as the open surface area of a cutout segment increases the flexibility of a zone composed of units having the larger cutout segments increases. Conversely, flexibility is inversely correlated with the uncut area; as the uncut surface area increases, flexibility decreases.

The total uncut area at any one point on the tube frame 1005 will depend on a number of factors, including the number of bands in each zone and the dimensions of the cutout segments (the open surface area of a particular unit). If the number of bands in each zone are constant, then the rank order is for the uncut surface area, unit of zone 1>unit of zone 2>unit of zone 3>unit of zone 4>unit of zone 5>unit of zone 6>unit of zone 7 (in other words, there is a fading of uncut area across zones) and the rank order of flexibility of the tube is zone 1<zone 2<zone 3<zone 4<zone 5<zone 6<zone 7 (flexibility is positively correlated with the open surface area and inversely correlated with the uncut area). The change in flexibility across multiple different zones can be linear, exponential or assume a step-wise or square wave function, increasing, decreasing, constant, discontinuous or continuous.

By using different zone patterns along the shaft length, flexibility can be increased or decreased along the shaft length, as well as other characteristics of the tube, such as torque, flexibility, pushability, resistance to axial compression and stretch, maintaining lumen diameter and kink resistance.

Figure 9A:
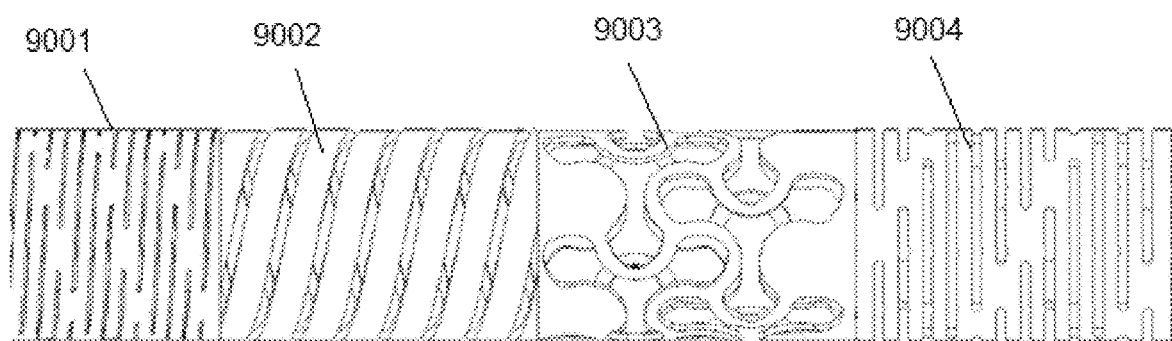
FIGS. 9a-9b illustrate examples of cut patterns for a catheter constructed in accordance with the principles of the present disclosure.

According to embodiments of the present disclosure, a tube frame 1005 can include a plurality of different cut patterns along lengths thereof that provide varying degrees of stiffness. For example, as shown in FIG. 9*a*, the tube frame 1005 includes a first section 9001 having interrupted or discontinuous spiral cuts interspersed with uncut sections, which provides an average stiffness for that section between 0.002-0.004 N/mm, with a preferred embodiment having a stiffness of 0.003 N/mm; a second section 9002 that contains a continuous spiral pattern described above, which provides an average stiffness for that section between 0.001-0.003 N/mm, with a preferred embodiment having a stiffness of 0.002 N/mm; and a third section 9003 that includes one or more zones and patterns described above and illustrated in FIGS. 8*a*-8*c*, which provides an average stiffness for that section between 0.002-0.004 N/mm, with a preferred embodiment having a stiffness of 0.003 N/mm. The tube frame 1005 may further include section 9004, which may include a plurality of interconnected rings as described herein which may provide an average stiffness for that section between 0.005-0.016 N/mm. The spiral cut section may include several sub-sections that may have different spiral parameters, such as cut widths, gaps, pitches, etc., such that the bending flexibility along the spiral cut section can vary longitudinally as desired. Any combination of the cut patterns described herein may be used in the tube frame 1005.

Figure 9B:
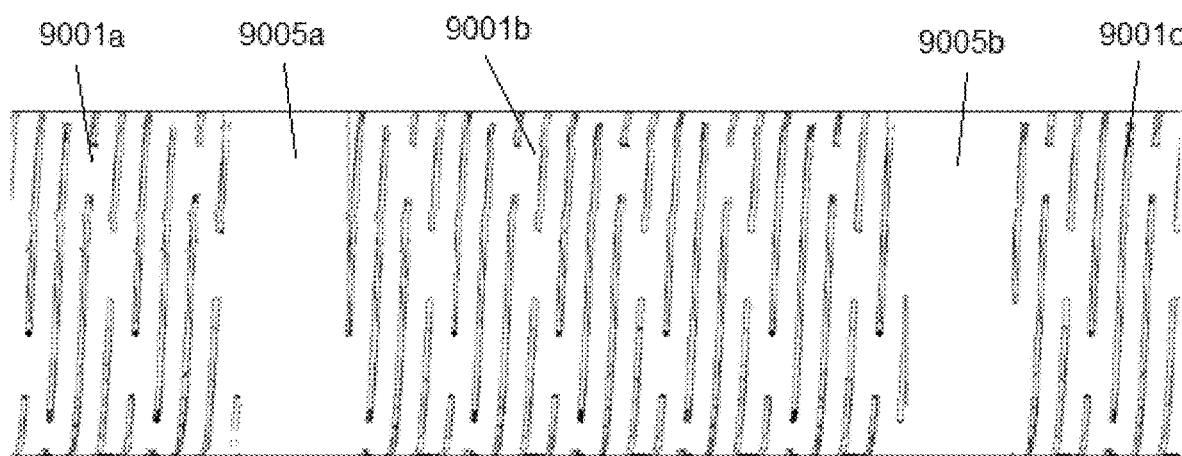

Now referring to the example shown in FIG. 9*b*, the tube frame 1005 may also include one or more solid, uncut sections 9005*a*, 9005*b* spanning the length of the tube frame 1005. The uncut sections 9005*a*, 9005*b* may be situated between two different (or the same) cut patterns, including the interrupted spiral cut sections 9001*a*-*c*, and/or interspersed between one or more segments having spiral cuts, interconnected rings, or other patterns, such as those shown in FIG. 9*a* or as otherwise described herein.

Figure 10A:
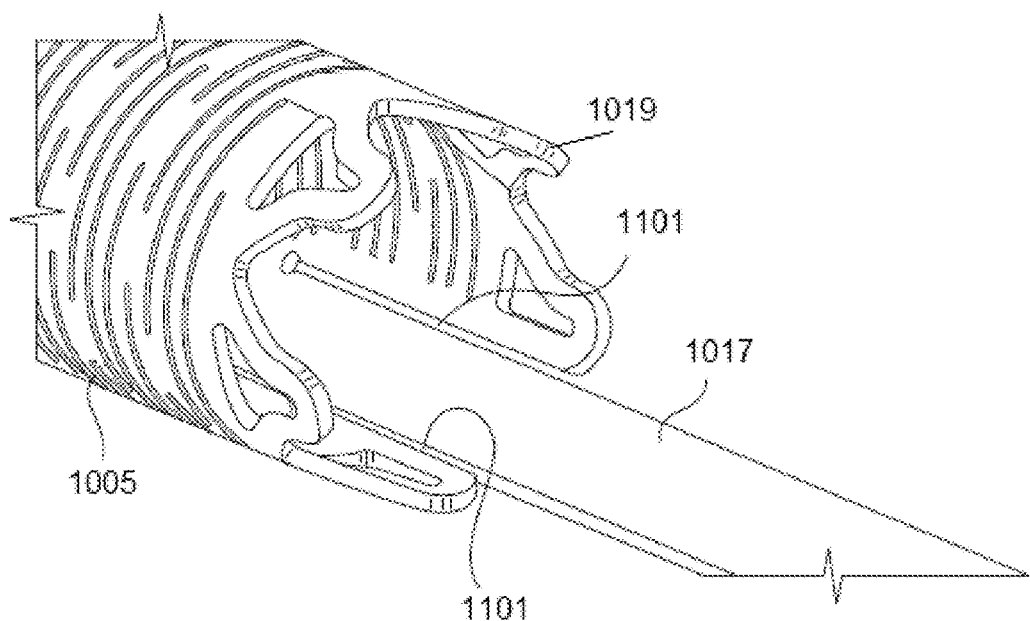
FIG. 10a is a perspective view of an example of a tube frame of a catheter constructed in accordance with the principles of the present disclosure.
Figure 10B:
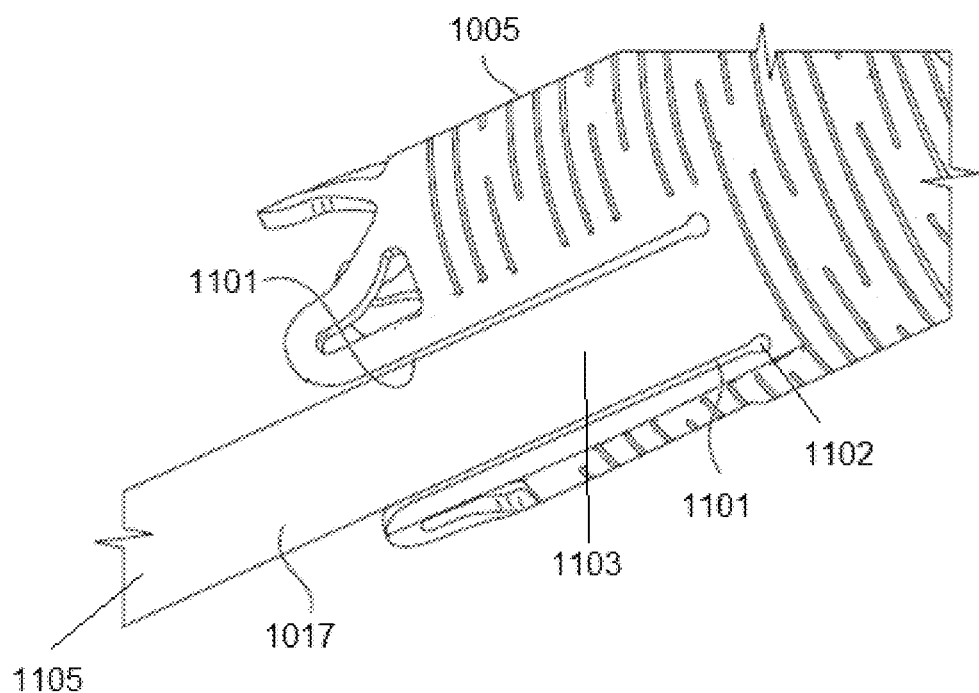

The tube frame 1005 may be coupled to the push member 1001 in a variety of different ways. For example, as shown in FIGS. 10*a*-*b*, the tube frame 1005 may define or include a tongue element 1017 that extends proximally from a proximal segment of the tube frame 1005. The tongue 1017 may be unitary with and be formed from the same material composition as the tube frame 1005. A distal end or region of the tongue 1103 may be positioned distally to the proximal opening of the tube frame 1005/lumen 1008, while a proximal end or region 1105 of the tongue element 1005 extends proximally past the proximal opening of the tube frame 1005. FIG. 10*b*. The tongue element 1017 can be recessed or offset longitudinally along the tube frame 1005 in relation to the proximal opening of the lumen 1008. The tongue element 1017 and/or the proximal segment 1010 of tube frame 1005 may include one or more cuts or spaces 1101 adjacent to the tongue element 1005 to allow the tongue element 1005 to pivot and/or cantilever to a degree with respect to the remainder of the tube frame 1005. FIGS. 10*a*-*b*. The cuts or spaces 1101 may connect to or otherwise include one or more keyholes 1102 to facilitate such cantilever movement and reduce the risk of material failure at the deflection point of the tongue. FIG. 10*b*. Such cantilever or pivot movement will thus be oriented about the recessed distal end of the tongue element 1017, which can be supported by other components described herein, and reduce the likelihood of material fatigue and/or cyclic loading failure of the tongue element 1017 during use of the guide catheter extension.

Figure 11A:
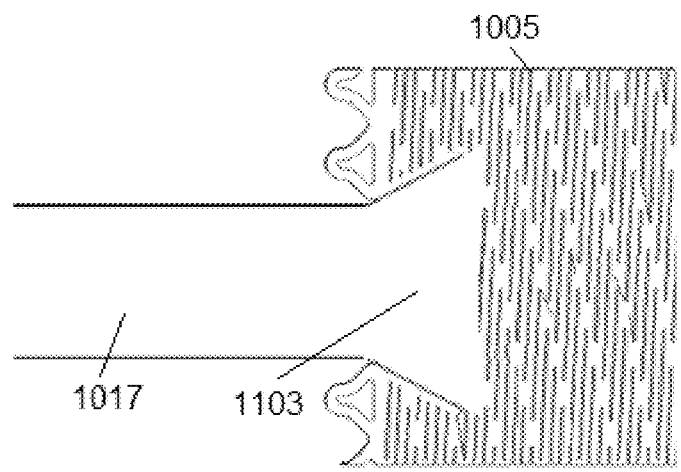
FIGS. 11a-11b illustrate alternative examples of tube frames of a catheter constructed in accordance with the principles of the present disclosure.
Figure 11B:
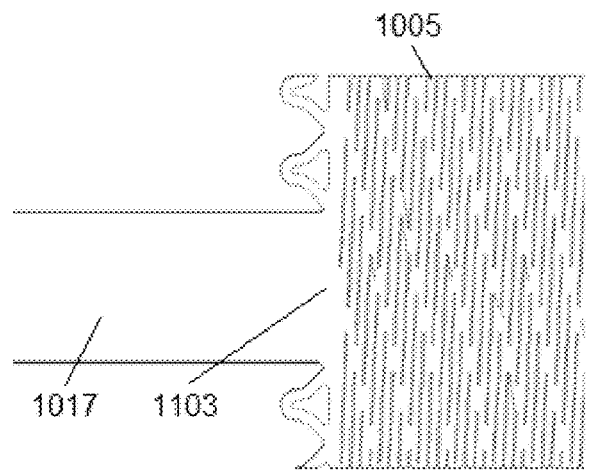

The distal region 1103 on the tongue element 1017 may assume a variety of different shapes. In one embodiment, the distal region 1103 assumes a generally trapezoidal shape. FIG. 11*a*. In this embodiment, the cuts or spaces 1101 are angularly offset with respect to the longitudinal axis LA 1009 of the tube frame 1005. The embodiment where the distal region 1003 is generally rectangular is shown in FIG. 10*b*. In this embodiment, the cuts 1101 are shown as generally parallel to longitudinal axis, LA 1009 of the tube frame 1005. In a third embodiment, the distal region 1103 of the tongue element 1017 is flush with the proximal end 1012 of the tube frame 1005. FIG. 11*b*.

Figure 12:
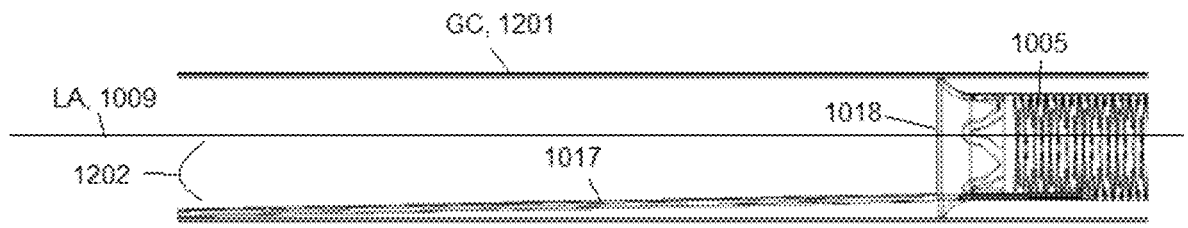
FIG. 12 is a side view of an example of a catheter constructed in accordance with the principles of the present disclosure.

The tongue element 1017 may be angled with respect to the longitudinal axis, LA 1009. FIG. 12. For example, as shown in FIG. 12, the tongue 14 extends towards an inner wall 103 of a surrounding guide catheter "GC" (1201), thereby decreasing any obstruction or cross-sectional obstacle that the tongue element 1017 may impose in more proximal regions of the tube frame 1017 where additional devices, instruments, or the like may be positioned. The angle of deflection θ 1202 of the tongue element 1017 may vary to accommodate particular applications and/or guide catheter dimensions. In one example, the angle between the tongue element 1017 and the longitudinal axis LA 1009 may be approximately 10 degrees. Other embodiments of the angle of deflection can range from approximately 5 degrees to 35 degrees.

Figure 13A:
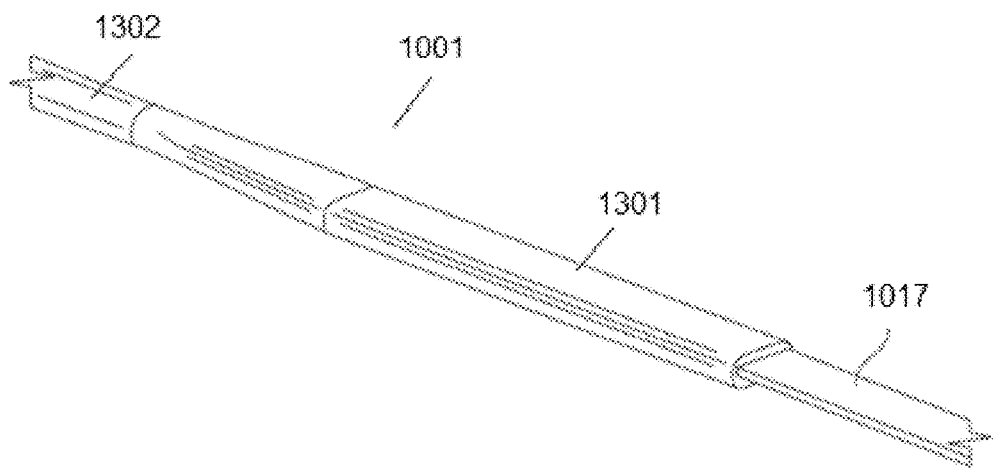
FIG. 13a-13b is a perspective view of an example of a push rod coupling constructed in accordance with the principles of the present disclosure.
Figure 13B:
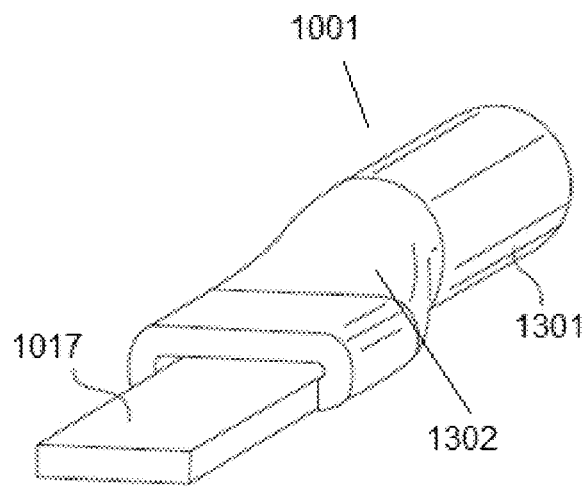

The tongue element 1017 may be sized and/or shaped to matably couple with a portion of the push member 1001. For example, as shown in FIGS. 13*a*-*b*, the tongue element 1017 may have a substantially rectangular cross section 1301 that is positioned within a correspondingly-shaped slot of the push member 1001. The slot of the push member 1001 may be formed, for example, by flattening a portion 1301 of the otherwise substantially rounded tube 1302 that constitutes a portion of the push member 1001. Other shapes and cross-sectional profiles may be implemented to couple the tube frame 1005 to the push member 1001, and the coupling may be achieved and/or secured by any bonding method, including, crimping, swaging, staking, adhesive bonding, welding, brazing and/or soldering.

Figure 14:
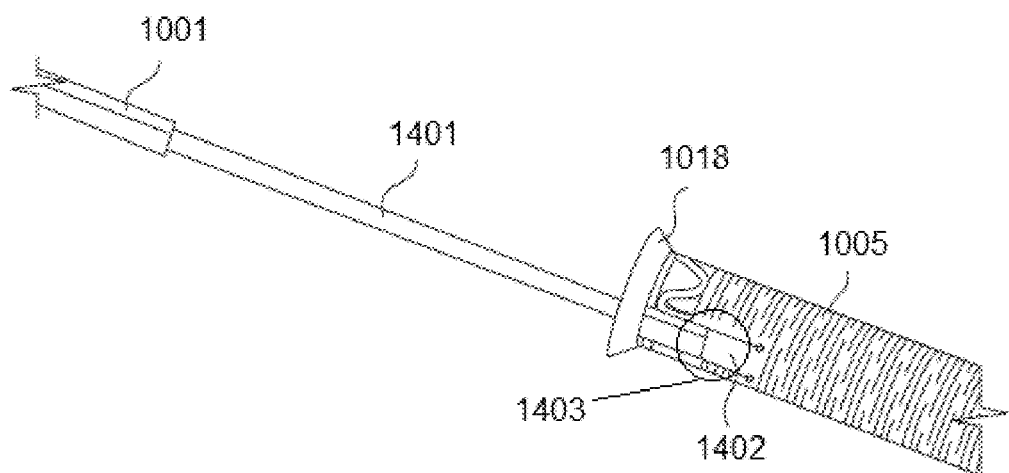
FIG. 14 is a perspective view of an alternative example of a push member coupling constructed in accordance with the principles of the present disclosure.

Now referring to FIG. 14, another example of an interconnection between the tube frame 1055 and push member

1001 is shown. In this example, an intermediate coupling member 1401, such as a wire, shim, rod, or the like, couples to the tongue element 1402 of the tube frame 1005 and extends proximally to couple to the push member 1001. In this example, the intermediate coupling member 1401 may slide over or otherwise attach to the tongue 1402 which may have a shorter length when compared to the examples of the tongue element 1017. The intermediate coupling member 1401 is matably connected 1403 to the push member 1001 at an opposite end.

Figure 15:
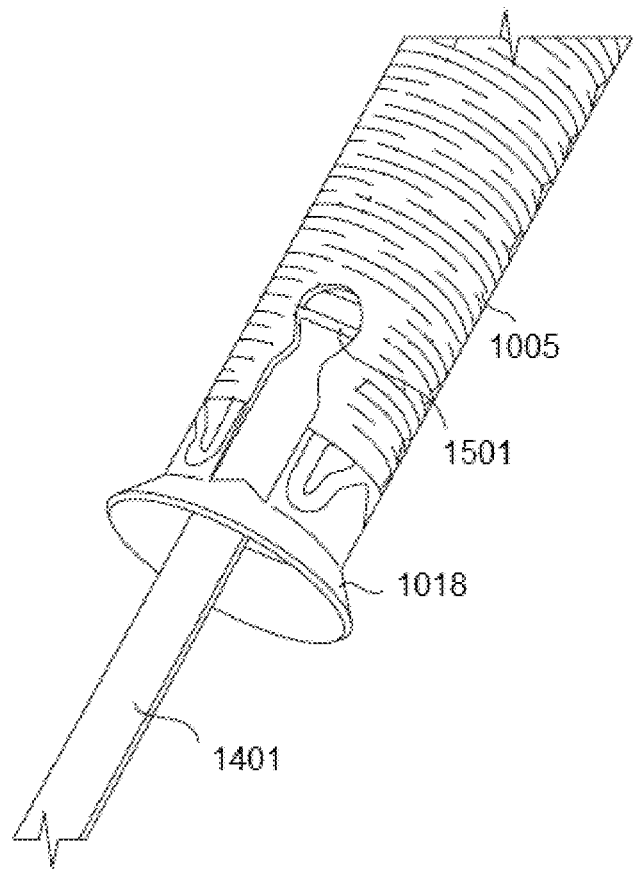
FIG. 15 is a perspective view of another alternative example of a push member coupling constructed in accordance with the principles of the present disclosure.
Figure 16:
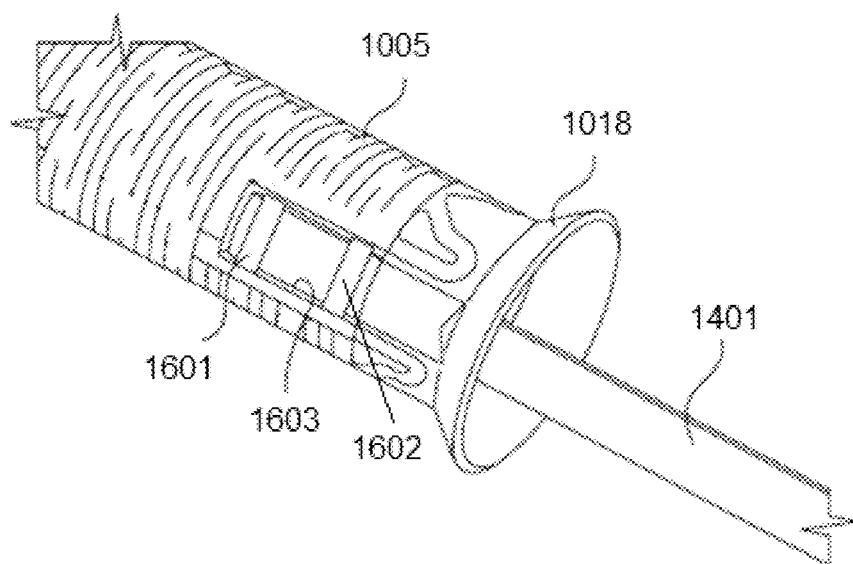
FIG. 16 is a perspective view of yet another alternative example of a push member coupling constructed in accordance with the principles of the present disclosure.

In another example, the intermediate coupling member 1401 may couple to or be positioned within an aperture or opening 1501 defined by the tube frame 1005. For example, as shown in FIG. 15, the tube frame 1005 defines a keyhole opening 1501 instead of a tongue element 1017, and the intermediate coupling member 1401 is positioned within the keyhole opening 1501. The keyhole opening 1501 in the tube frame 1005 may have varying shapes and sizes to accommodate the intermediate coupling member 1401 and facilitate coupling thereto. For example, FIG. 16 illustrates an example of a substantially rectangular opening 1603. The intermediate coupling member 1401 may be secured in-place with the application of an adhesive, weld, fuse, or other bonding modality, 1601, 1602. Now referring to FIG. 17, in addition and/or alternatively to such coupling, a cap 1702 may be positioned over a portion of the intermediate coupling member 1401 to enclose and secure the intermediate coupling member 1401 to the tube frame 1005, once again employing one or more applications of an adhesive, weld, fuse, or other bonding modality between the cap 1702, intermediate coupling member 1401, and the tube frame 1005.

Figure 17:
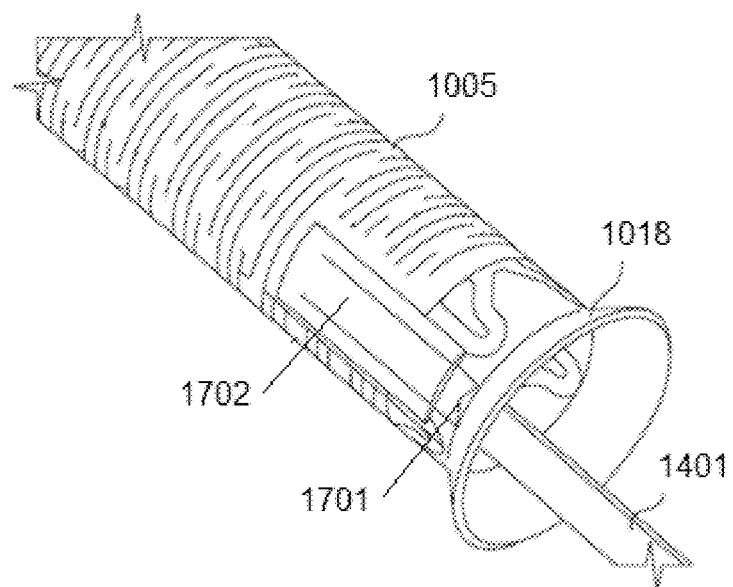
FIG. 17 is a perspective view of still another alternative example of a push member coupling constructed in accordance with the principles of the present disclosure.
Figure 18:
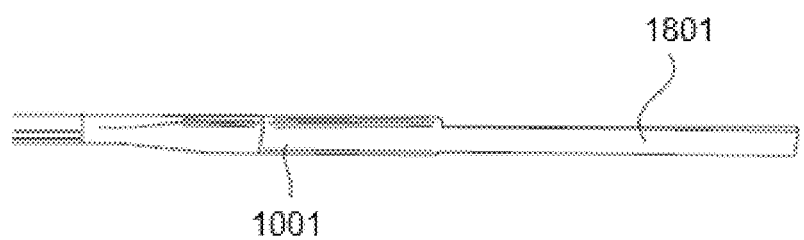
FIG. 18 is a perspective view of an example of a push member constructed in accordance with the principles of the present disclosure.

In another example, the push member 1001 may be directly coupled to an aperture or opening defined by the tube frame 5, such as those shown in FIGS. 16-17. In another embodiment, the push member 1001 may define an elongate portion or segment 1801 that couples directly to the aperture or opening defined by the tube frame 1005. The push member 1001 may then be secured directly to the tube frame 1005 by employing one or more applications of an adhesive, weld, fuse, or other bonding modality.

Figure 19A:
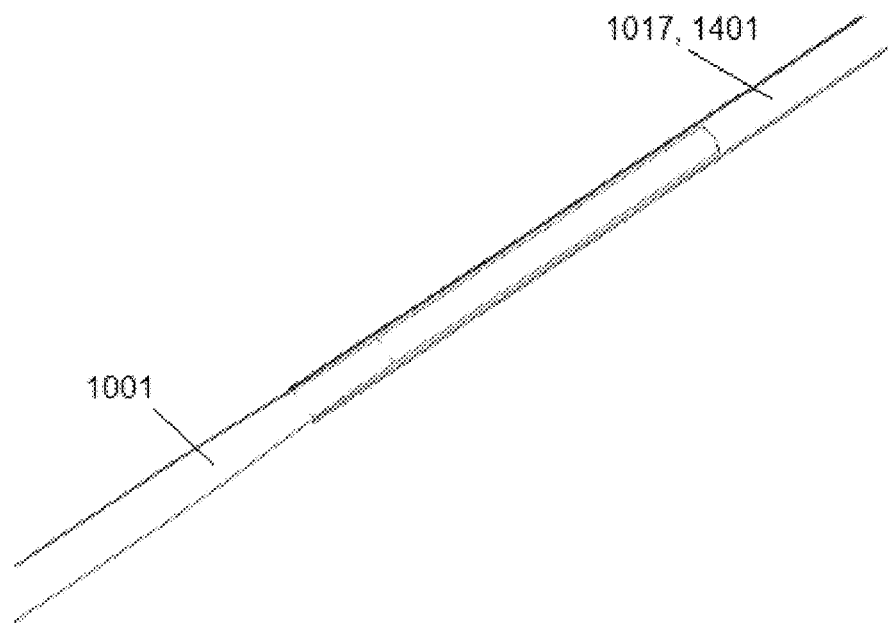
FIG. 19a is a top perspective view of another alternative example of a push member coupling constructed in accordance with the principles of the present disclosure.
Figure 19B:
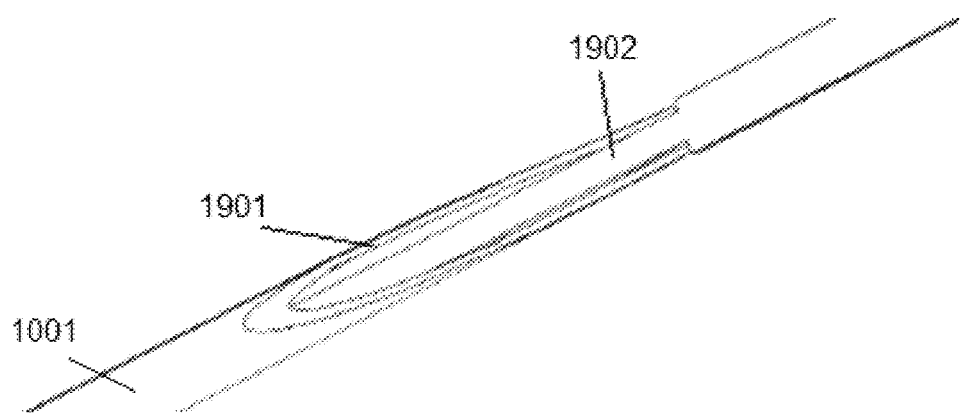
Figure 19C:
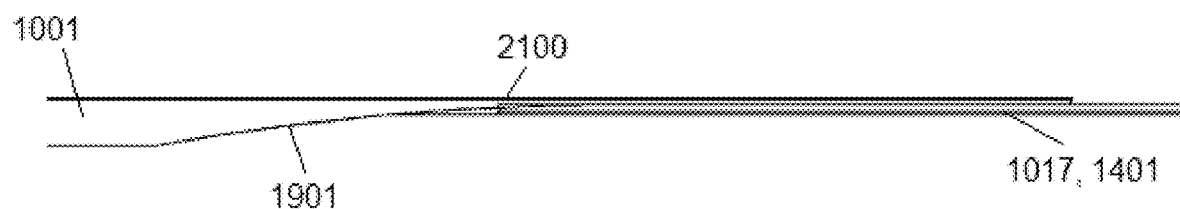
Figure 23A:
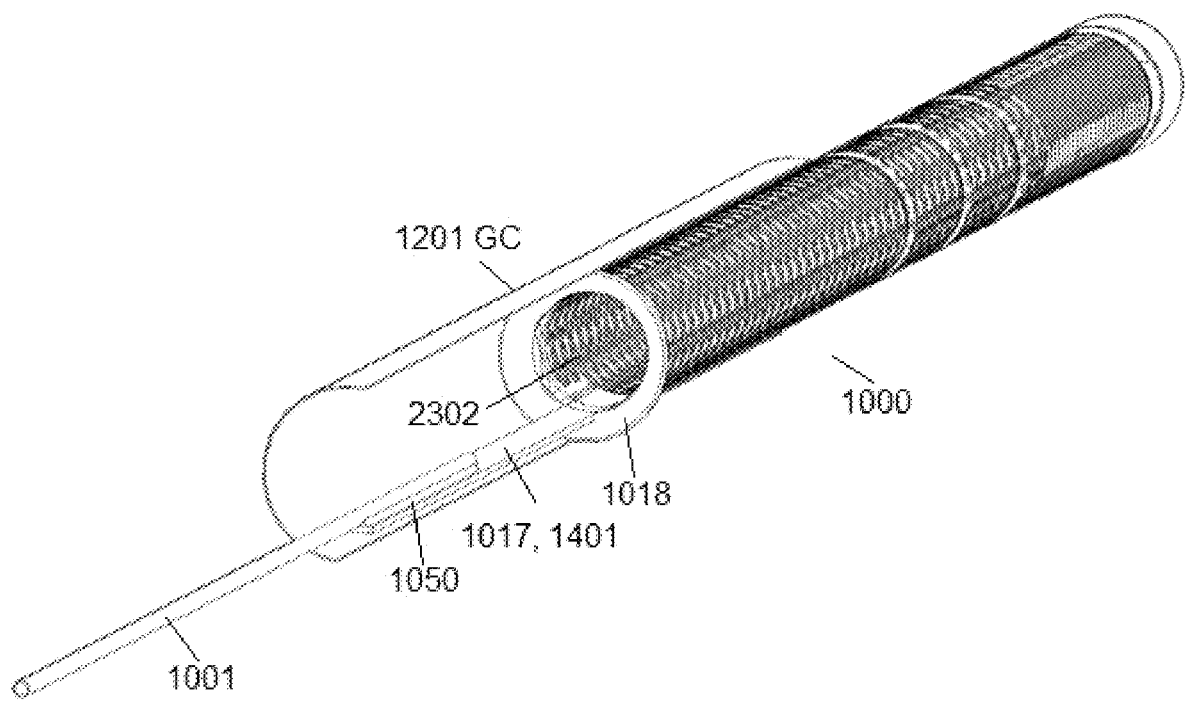
FIGS. 23a-23c depict examples of tube frame flares for a catheter constructed in accordance with the principles of the present disclosure.
Figure 23B:
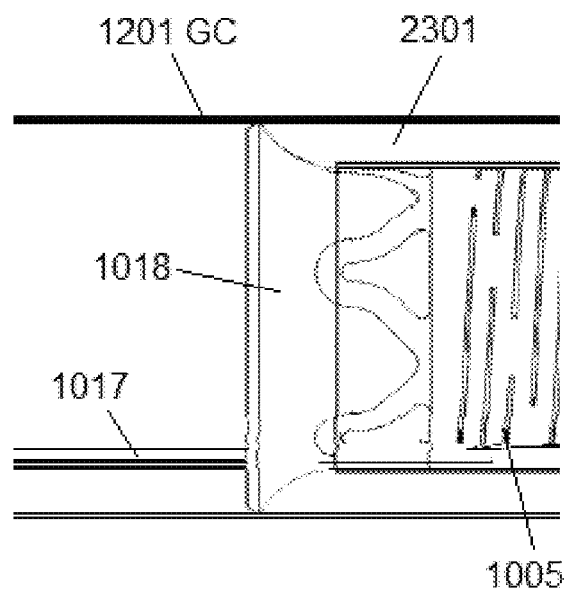
Figure 23C:
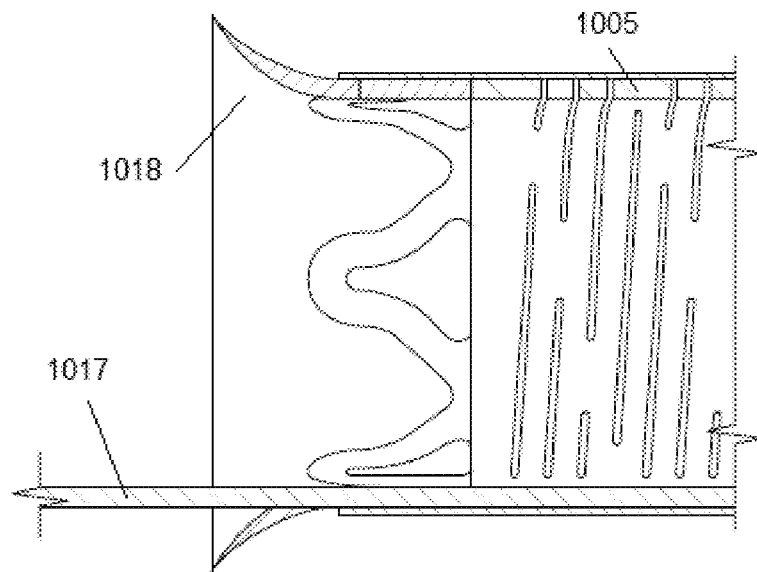

In another example, as shown in FIGS. 19a-b, a length of the push member 1001 may overlap with a length of the tongue element 1017 and/or the intermediate coupling member 1401 to increase the surface area between the two components for bonding or other attachment. The push member 1001 may further define or include a skive portion 1901 that receives a tapered or cut portion 1902 of the tongue element 1017 and/or the intermediate coupling member 1401. In an alternative example, as shown in FIGS. 1a and 23a, the push member 1001 overlaps the tongue element 1017 and is bonded through and adhesive or weld 1050 to secure the components together.

Figure 20A:
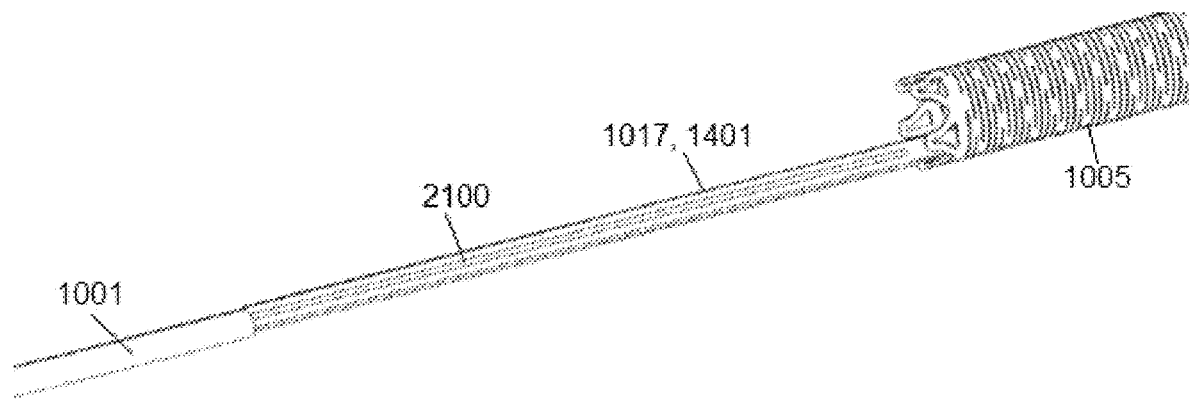
FIG. 20a is a top perspective view of another alternative example of a push member coupling constructed in accordance with the principles of the present disclosure.
Figure 20B:
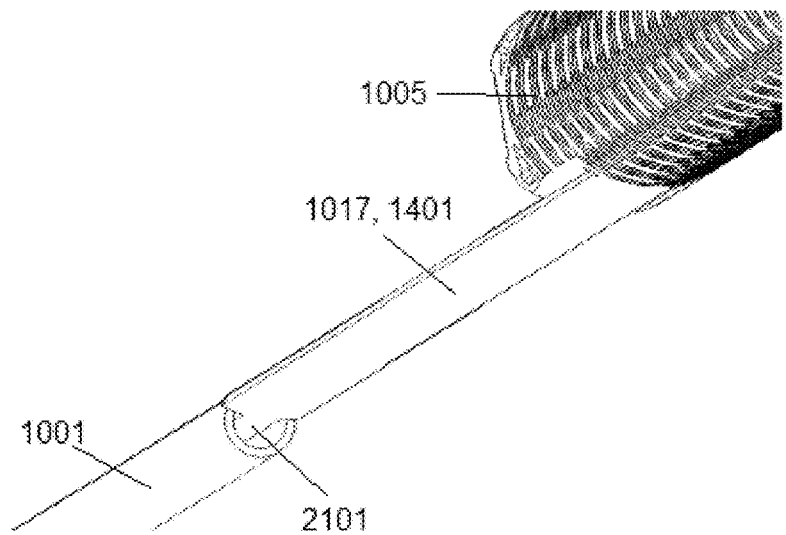

Now referring to FIGS. 20a-b, a wire 2100 may be coupled to and overlap each of the push member 1001 and the tongue element 1017 and/or the intermediate coupling member 1401 to increase the stability and strength of the attached assembly. The wire 2100 may be bonded or otherwise coupled to each of the push member 1001 and the tongue element 1017 and/or the intermediate coupling member 1401 by welding, adhesive, or other manufacturing process. The tongue element 1017 and/or the intermediate coupling member 1401 may also include a cutdown or tapered section 2101 that extends into an internal cavity or opening of the push member. FIG. 20c.

Another example of an interconnection between the tube frame 1005 and push member 1001 is illustrated in FIGS. 21a-d. In this example, the push member 1001 includes a keyhole 2102 sized and shaped to receive a corresponding, complementary keyhole cutdown region 2103 of the tongue element 1017 and/or the intermediate coupling member 1401, as well as overlapping a length of the push member 1001 with a length of the tongue element 1017 and/or the intermediate coupling member 1401 to increase the surface area between the components for bonding or other attachment.

Figure 21A:
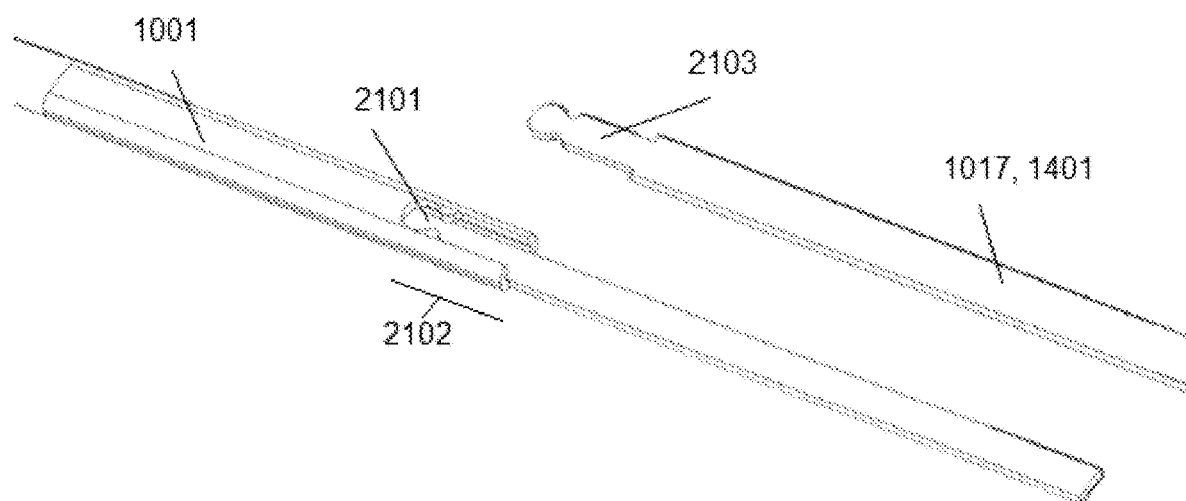
FIG. 21a is a top perspective assembly view of another alternative example of a push member coupling constructed in accordance with the principles of the present disclosure.
Figure 21B:
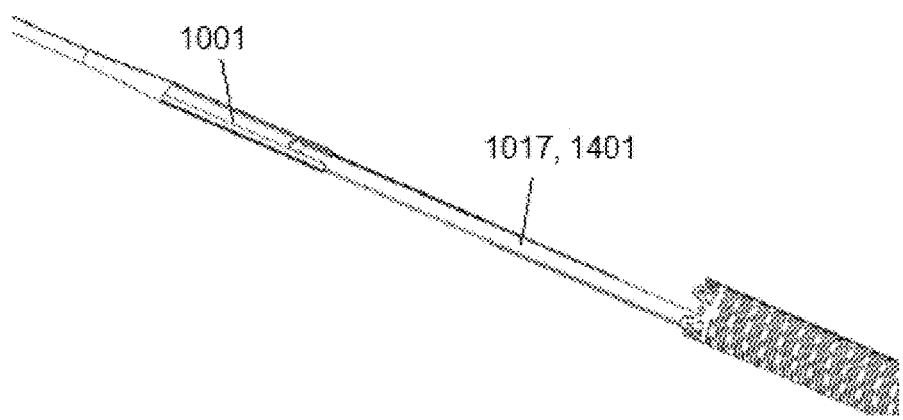
Figure 21C:
FIGS. 21c-21d are examples of flexibility patterns constructed in accordance with the principles of the present disclosure.
Figure 21D:
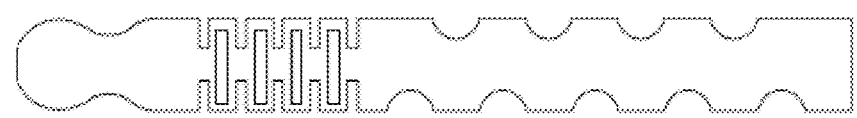

The tongue element 1017, the intermediate coupling member 1401, and/or the portion of the push member 1001 coupled to the tube frame 1005 may include one or more features, dimensions, geometries, and/or profiles to facilitate flexibility in one or more planes of motion, thereby improving and/or contributing to the overall flexibility of the guide extension catheter. Examples of such features are shown in FIGS. 21c-d, including one or more cutouts, slots, or curved portions to provide flexion or bending in side-to-side and/or up-and-down directions. Other implementations or combinations of such features may be employed to provide a desired degree or range of bending.

Figure 22A:
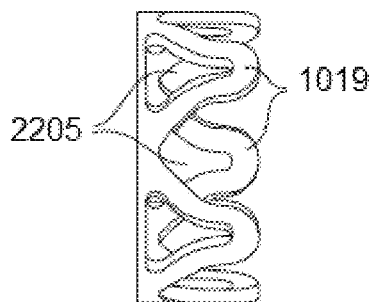
FIGS. 22a-22f depict examples of axial protrusion configurations constructed in accordance with the principles of the present disclosure.

The tube frame 1005 may include one or more axially-oriented protrusions 1019 extending from the distal 1013 and/or proximal 1012 ends of the tube frame 1005 that provide for or can facilitate attachment of one or more components or layered materials, as described further herein. FIGS. 22a-f. In certain embodiments, the protrusions 1019 may be generally parallel with the longitudinal axis LA 1009 of the tube frame 1005. Alternatively, the distal 1012 and/or proximal ends 1013 of the tube frame 1005 may be flush or flat, i.e., perpendicular with respect to the longitudinal axis 1009. FIG. 22a. For example, protrusions 1019 may be made from a plurality of closed, curvilinear elements which can be sinusoidal or generally wave-form (meandering) in shape. FIG. 22a.

Figure 22B:
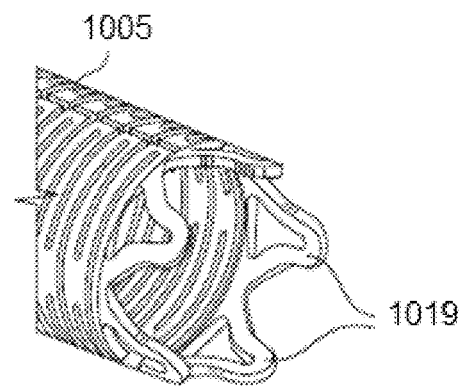

The protrusions 1019 may be laser cut or otherwise manufactured directly from the wall of the tube frame 1005, or otherwise assembled or coupled to the tube frame 1005 such that the protrusions 1019 share substantially the same inner 2201 and outer diameter 2202 dimensions with the tube frame 1005 (inner dimensions 2203 of the lumen 1008 and outer dimensions 2204 of the tube frame 1005). For example, as shown in FIGS. 22a-b, the protrusions 1019 may include a plurality of curvilinear projections in a crown-like configuration that substantially circumscribe an end or opening to the lumen of the tube frame 1005. The curvilinear protrusions each include an inner aperture or opening 2205 therein. FIGS. 22a-b.

Figure 22C:
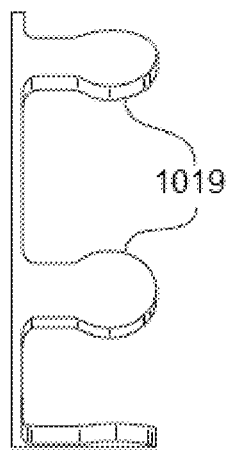
Figure 22D:
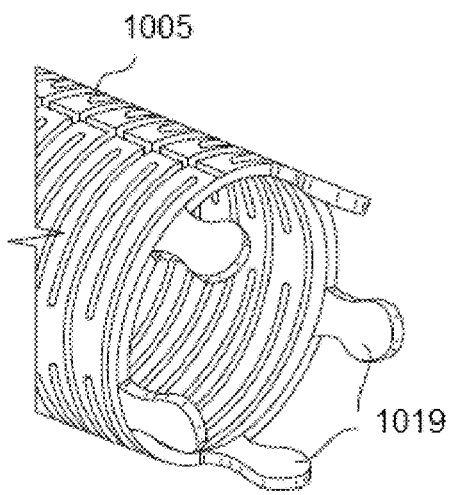
Figure 22E:
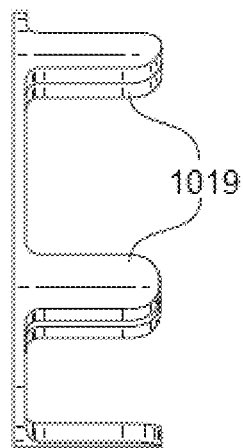
Figure 22F:
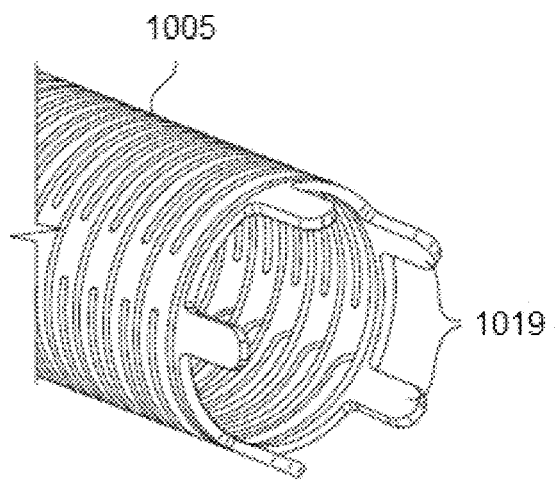

In another example, the protrusions 1019 may each include a substantially keyhole-like shape, as shown in FIGS. 22c-d. The keyhole protrusions 1019 may generally include a substantially rectangular portion coupled to a substantially circular or curvilinear portion at an end thereof, where the substantially circular or curvilinear portion has a diameter larger than a width of the substantially rectangular portion. In another example, the protrusions 1019 may each include a substantially rounded rectangular shape, as shown in FIGS. 22e-f. The protrusions 1019 may generally include a substantially rectangular portion coupled to a substantially semi-circular or curvilinear portion at an end thereof, where the substantially semi-circular or curvilinear portion has a diameter substantially the same as a width of the substantially rectangular portion.

The proximal end 1012 of the tube frame 1005 may include a flare or flange 1018 (FIG. 1b). The flare or flange 1019 can be used to close or reduce the gap between the tube frame 1005 of the guide catheter 1201. FIG. 23a. The guide catheter (GC) 1201 encloses the guide catheter extension, as well as provide a guiding, angled surface to direct wires, instruments, and/or other devices being inserted and routed through the guide catheter extension (such as a treatment catheter or stent delivery device) into the proximal opening 2302 and into the lumen 1008 of the tube frame 1005. The flare 1019 may thus be substantially coaxial with the longitudinal axis LA 1009 of the tube frame 1005 and the lumen 1008 therethrough and may extend proximally from a proximal end 1012 of the tube frame 1005 to the distal end 1013. In the embodiment shown, the flare or flange 1018 extends radially outwardly from the proximal opening 2302 and lumen 1008 of the tube frame 1005 and has a greater outer diameter than the outer diameter of the tube frame 1005. The flare or flange 1019 can substantially close or seal any gap 2301 formed between the guide catheter 1201 and the tube frame 1005. The cross-sectional area of the flare or flange 1018 can taper or be thinner at the point on the flare 2303 not attached to the axial protrusions 1021. Functionally, this section of the flare or flange 2305 can act as a "wiper blade" which can be in contact with the guide catheter 1201. This decrease in cross-sectional area across the flare or flange 1018 from the area in contact with the axial protrusions to the area not in contact will result in an increasing flexibility or ability to bend of the flare or flange 1018 at the area or section 2305 not in contact with the axial protrusions. This flexibility allows the flare or flange 1018 to accommodate catheters of different diameter while maintaining a seal between the guide catheter 1201 and the tube frame 1005. For example, this type of construction enables the guide catheter extension to be used to inject contrast media into a target site in the patient's vasculature without leakage from the distal end of the guide catheter extension, as well as facilitate efficient aspiration through the lumen 1008 of the tube frame 1005, rather than through interstitial spacing or gaps between the tube frame 1005 and the guide catheter 1201.

The flare or flange 1018 can be made from one or more elastic polymeric materials, preferably rubbery material with good lubricity, such as PEBA, PTFE, silicone or other fluoropolymers. The flare or flange 1018 may also be radiopaque, which may be achieved by utilizing a tungsten-filled or bismuth-filled polymer, such as PBAX®. The thickness of the flare or flange 1018 can be selected to ensure the flare or flange 1018 has sufficient pliability to allow the guide catheter extension to move axially within the guide catheter 1201 without significantly hampering its maneuverability. For example, the thickness of the flare 120 can be about 0.05 mm (0.0019 inches) to about 1 mm (0.039 inches), or about 0.2 mm (0.0078 inches) to about 0.5 mm (0.0196 inches).

The flare or flange 1018 can be made as a separate piece and adhered to a proximal end 1012 of the tube frame 1005, including adherence or coupling of the flare or flange 1018 to the protrusions 1019 (as shown in FIGS. 1*a-c*). In such examples, the flare or flange 1018 may be fused or melted onto the protrusions 1019, and the protrusions 1019 may resist axial separation of the flare or flange 1018 through the geometry and/or aperture/opening features of the protrusions 1019. In an alternative example, the flare or flange 1018 may be constructed or formed as an extension of an inner lining or outer jacket of the guide catheter 1201. The end of the flare or flange 1018 may be substantially perpendicular or perpendicular, i.e., not in a skived configuration, with respect to the longitudinal axis LA 1008 of the tube frame 1005. See, e.g., FIG. 1*b*.

The flare or flange 1018 can further provide structural support to the tongue element 1017 and/or the intermediary coupling member 1401 by being partially fused to and/or having a portion of the flare or flange positioned against an underside of the tongue element 1017 and/or intermediary coupling member 1401. The flare or flange 1018 can thus support against or restrain excessive deflection and/or material failure of the tongue element 1017 and/or intermediary coupling member 1401 when the guide catheter is in use.

Figure 24:
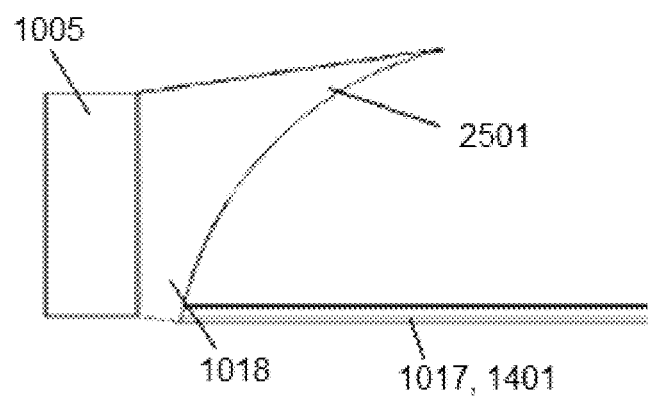
FIG. 24 depicts an example of a flare for a catheter constructed in accordance with the principles of the present disclosure.

The flare or flange 1018 may include a substantially uniform circumferential profile. Alternative shapes and profiles of the flare or flange 1018 may also be utilized to facilitate both sealing of the catheter to the inner wall of the external guide catheter, as well as aiding reception of the guidewire into the lumen of the distal tube. For example, as shown in FIG. 24, the flare or flange 1018 may have an asymmetrical protruding section 2501 extending further outward from a remainder of the flare or flange 1018. The protruding section may be positioned on the "top" of the device (e.g., substantially opposite the tongue element 1017 or intermediate coupling member 1401. FIG. 24. In FIGS. 25*a-c*, another example of the flare or flange 1018 is shown having two protruding sections 2601 positioned opposite each other. In FIGS. 26*a-b*, another example of the flare or flange 1018 is shown having four protruding sections 2701 positioned approximately equidistant form one another around the circumference of the flare. In FIGS. 27*a-c*, another example of the flare or flange 1018 is shown having a plurality of protruding sections 2801 positioned around the circumference of the flare or flange 1018.

Figure 28A:
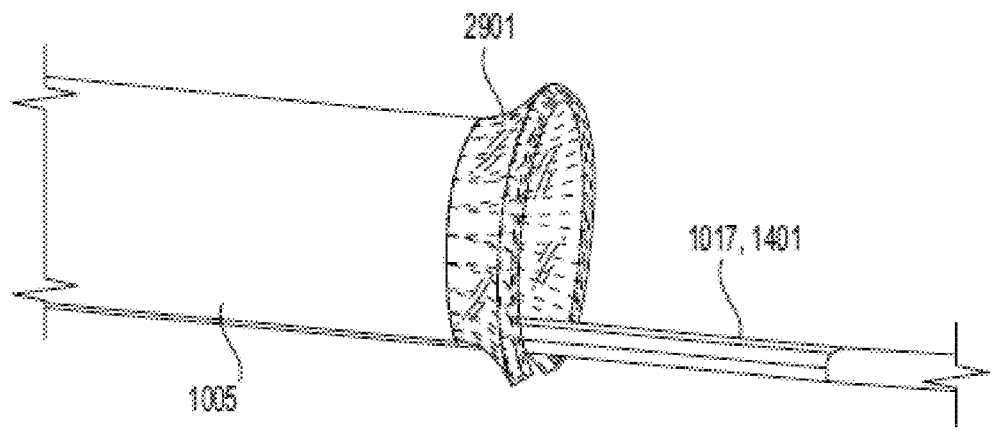
FIGS. 28a-28b depict yet another example of a flare for a catheter constructed in accordance with the principles of the present disclosure.
Figure 28B:
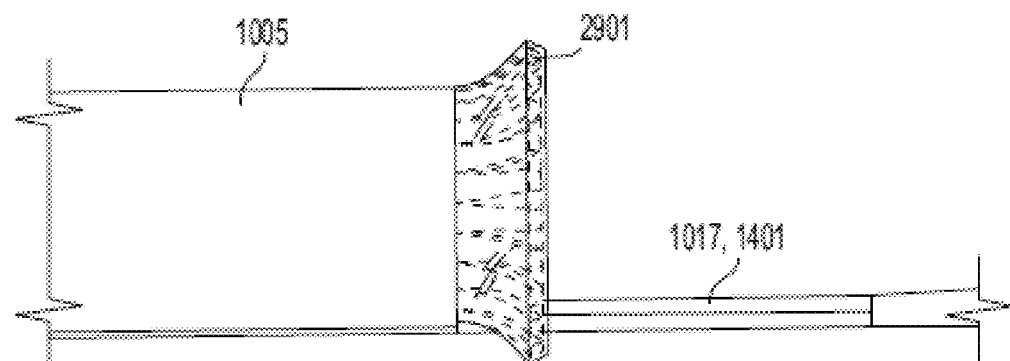

In one embodiment, these protruding sections 2801 are formed from same materials as the tube frame 1005 by cutting a plurality of protruding sections 2901. The flare or flange 1018 can then enclose the plurality of protruding sections 2901. FIGS. 28*a-b*.

Figure 29A:
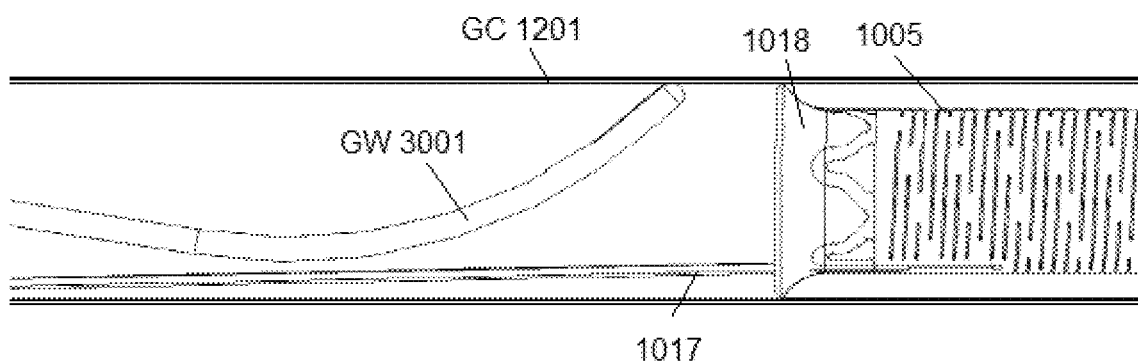
FIGS. 29a-29d depict a guidewire entering a distal assembly of a catheter constructed in accordance with the principles of the present disclosure.
Figure 29B:
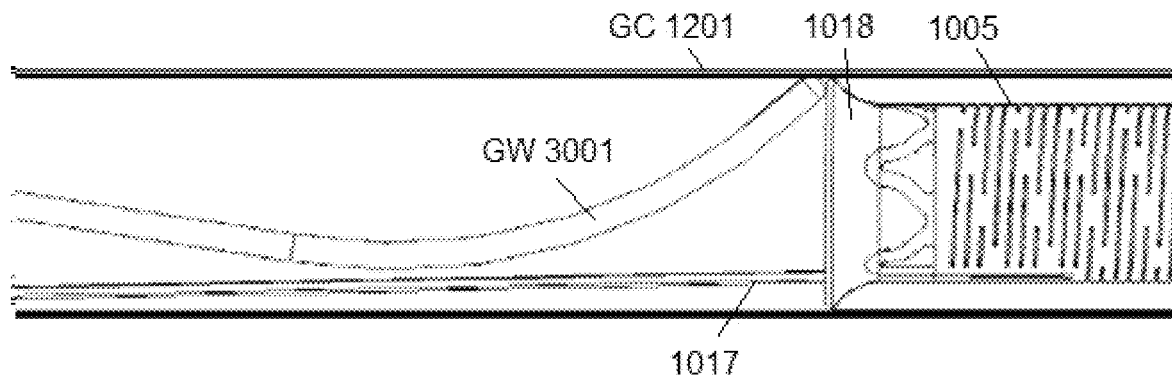
Figure 29C:
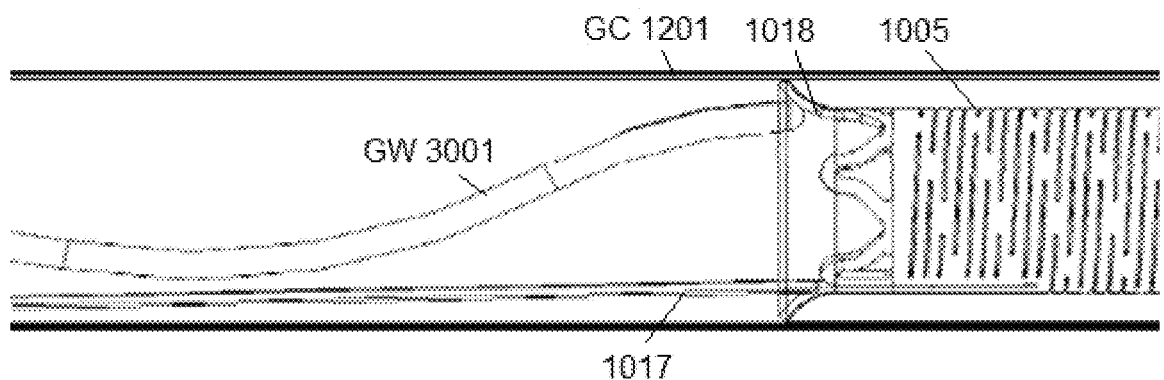
Figure 29D:
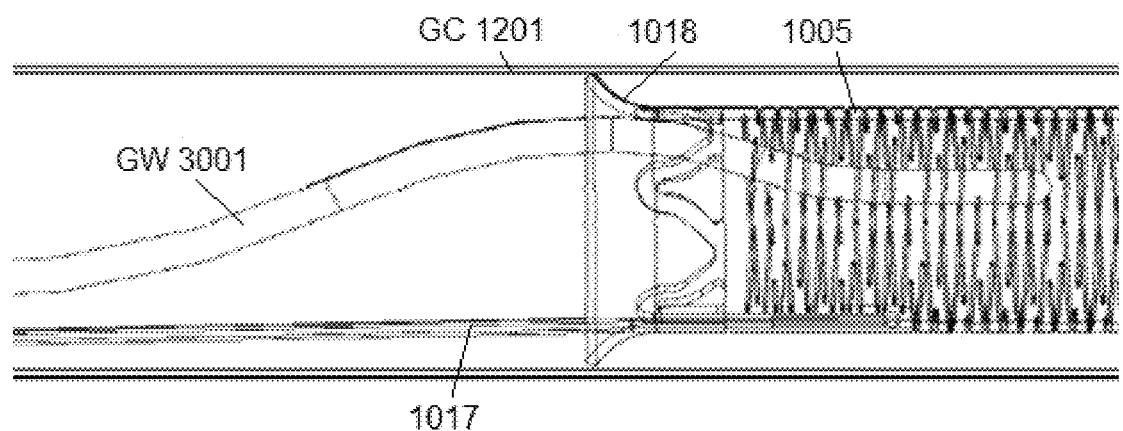

As stated above, the flare or flange 1018 aids in directing a guidewire 3001 and/or other instruments or devices passed through the external guiding catheter into the lumen 1008 of the tube frame 1005. For example, as shown in FIGS. 29*a-c*, a guidewire (GW) 3001 may be advanced through a proximal portion of the guide catheter (GC) 3001 towards the tube frame 1005 of the guide catheter extension. If the guidewire 122 is off-center or otherwise meandering through the lumen 1008 of the guide catheter (GC) 1201 when it comes into contact with the flare or flange 1018, the geometry and pliability of the flare or flange 1018 directs the guidewire (GW) 3001 into the lumen 1008 of the tube frame 1005 without damaging the guidewire 3001, as shown in FIGS. 29*a-d*. Once passed the threshold of the lumen 1008, the guidewire (GW) 3001 can be pushed through the remainder of the tube frame 1005 towards the distal end 1013 of the tube frame 1005 and out towards the anatomy to be traversed. FIGS. 29*a-d*.

Guidewires are typically comparatively thin, having a diameter in the order of about 0.254 mm to 0.457 mm. Guidewires (GW) are capable of transmitting rotation from the proximal end of the guidewire to the distal end of the guidewire. This transmission allows the physician to controllably steer the guidewire through the branches of the patient's arteries and manipulate the catheter to the intended target site in the coronary artery. Additionally, the distal end of the guidewire should be sufficiently flexible to allow the distal portion of the guidewire to pass through sharply curved, tortuous coronary anatomy.

Guidewires are well known in the art and the appropriate choice of a guidewire for use the catheter of the present disclosure can be made by a medical professional, such as an interventional cardiologist or interventional radiologist. Among the common guidewire (GW) configurations used in angioplasty is the type of guidewire illustrated in U.S. Pat. No. 4,545,390. Such a wire includes an elongate flexible shaft, typically formed from stainless steel, having a tapered distal portion and a helical coil mounted to and about the tapered distal portion. The generally tapering distal portion of the shaft acts as a core for the coil and results in a guidewire (GW) having a distal portion of increasing flexibility that is adapted to follow the contours of the vascular anatomy while still being capable of transmitting rotation from the proximal end of the guidewire to the distal end so that the physician can controllably steer the guidewire (GW) through the patient's blood vessels. The characteristics of the guidewire are affected significantly by the details of construction as the distal tip of the guidewire. For example, in one type of tip construction, the tapering core wire extends fully through the helical coil to the distal tip of the coil and can be attached directly to a smoothly rounded tip weld at the distal tip of the coil. Such a construction typically results in a relatively stiff tip suited particularly for use when attempting to push the guidewire through a tight area of stenosis. In addition to a high degree of column strength, such a tip also displays excellent torsional characteristics.

A liner 3101 may comprise one or more polymers arranged in layers to form a tube. For example, the liner 3101 may form a tube comprising two different materials, 3102, 3103, each with a different crystalline melt or melt temperature. The liner 3101 may be constructed from one or more polymers. Some examples of suitable polymers may include polytetrafluoroethylene (PTFE), ethylene tetrafluoroethylene (ETFE), fluorinated ethylene propylene (FEP), polyoxymethylene (POM, for example, DELRIN available from DuPont), polyether block ester, polyurethane (for example, Polyurethane 85A), polypropylene (PP), polyvinylchloride (PVC), polyether-ester (for example, ARNITEL available from DSM Engineering Plastics), ether or ester based copolymers (for example, butylene/poly(alkylene ether) phthalate and/or other polyester elastomers such as HYTREL available from DuPont), polyamide (for example, DURETHAN available from Bayer or CRISTAMID. available from Elf Atochem), elastomeric polyamides, block polyamide/ethers, polyether block amide (PEBA, for example available under the trade name PEBAX.), ethylene vinyl acetate copolymers (EVA), silicones, polyethylene (PE), Marlex high-density polyethylene, Marlex low-density polyethylene, linear low density polyethylene (for example REXELL), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR), polysulfone, nylon, nylon-12 (such as GRILAMID available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some examples, the liner 3101 can be blended with a liquid crystal polymer (LCP).

For example, as shown in FIG. 30, the liner 3101 may be disposed within the lumen 1008 of the tube frame 1005 and extend from the proximal end 1012 of the tube frame 1005, adjacent and/or coupled to the flare 1018 and/or axial protrusions 1019, down to and/or past the distal end 1013 of the tube frame 1005. The liner 3101 may have an overall length greater than the length of the tube frame 1005 such that a portion of the liner 3101 extends beyond and out of the distal end of the tube frame 5, as shown. The liner can form a tube 3103 within the tube frame 1005.

The liner 3101 contributes to (and/or not otherwise significantly impede) the operability of the tube frame 1005, and the guide catheter 1201 overall, to navigate tortuous anatomy having reduced radii of curvature, while also complimenting the pushability of the guide catheter extension both within and partially external to the guide catheter 1201. To achieve such performance, the liner 3101 may be constructed from the materials listed above and may include a wall thickness between approximately 0.00635 mm (0.00025 inches) and approximately 0.127 mm (0.005 inches). In a preferred example, the liner 3101 may be constructed from the materials listed above, and may include a wall thickness between approximately 0.00635 mm (0.00025 inches) and approximately 0.0127 mm (0.0005 inches).

The liner 3103 may be only partially and/or intermittently fused, bonded, or otherwise adhered to the tube frame 5 to further contribute to the overall flexibility and pushability of the guide catheter. The attachment of the liner 3103 to the inner wall of the tube may include, for example, heat fusing/melting, use of an adhesive, or other manufacturing processes. The bonding/attachment process may include one or more intermediary compounds or materials to facilitate or effect the attachment between the liner 3103 and the tube frame 1005. For example, in a device utilizing a liner constructed from PTFE, a PEBAX® powder coating may be applied between the PTFE liner and the distal tube. Heat may then be applied to the tube frame 1005 assembly at a temperature sufficient to melt the PEBAX®, but lower than a temperature required to melt the PTFE. The melted PEBAX® thus bonds the PTFE liner to the tube frame 1005 to secure it in place. The fused segment of PEBAX® can be attached as a ring or a point.

Figure 31:
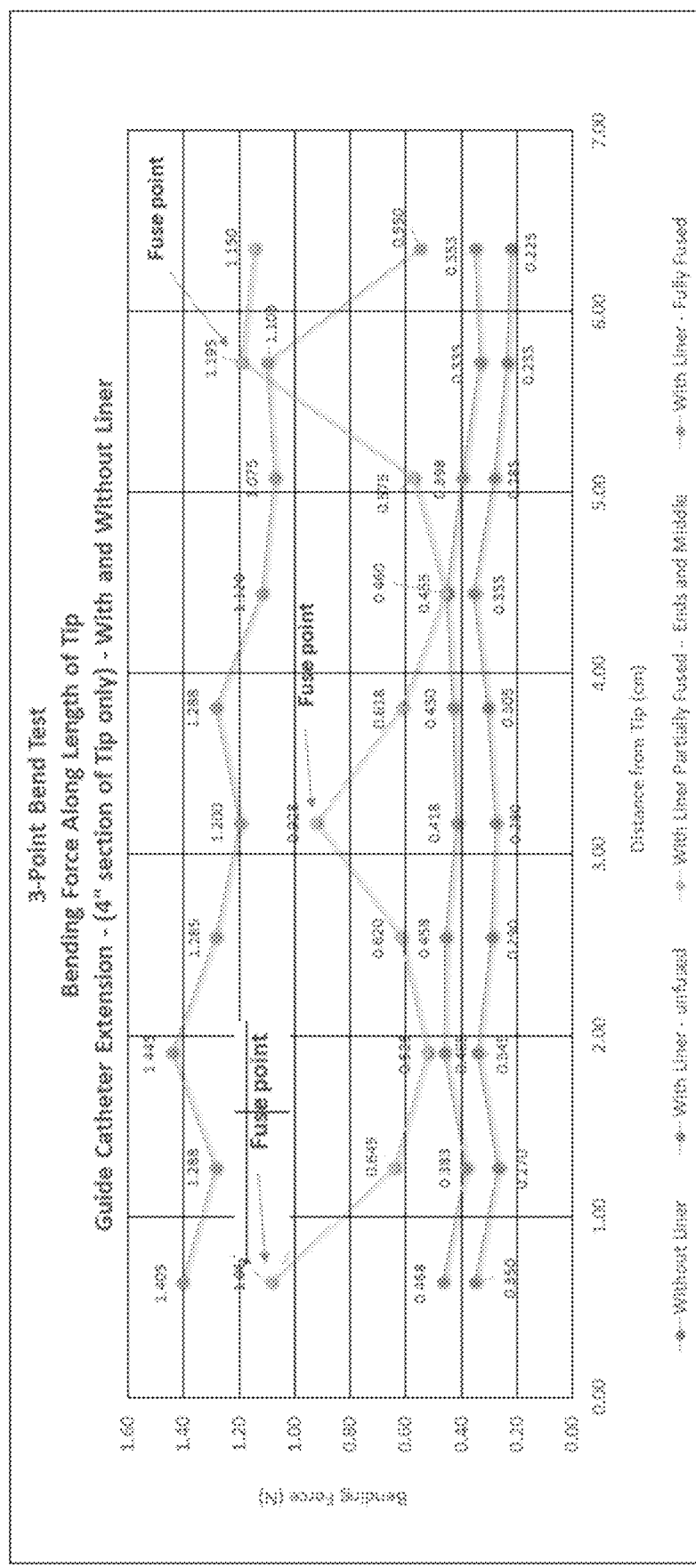
FIG. 31 is a chart illustrating flexibility testing of varying catheter components and assemblies.
Figure 32:
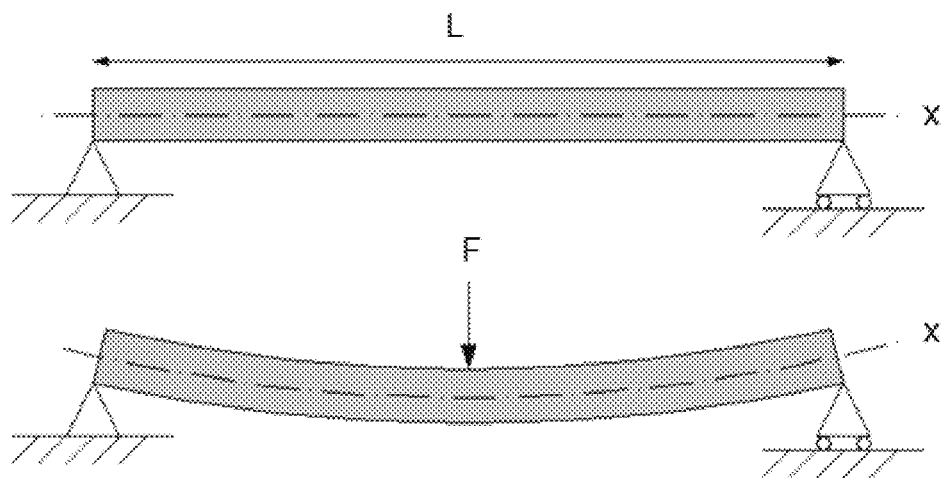
FIG. 32 is an illustration of a bend-test configuration for measuring flexibility.

When a polymeric liner is completely bonded to a tube frame 1005, the rigidity of the fused assembly greatly increases, and flexibility is decreased due to, at least in part, the change in hardness of the fused liner resulting from the bonding process. For example, FIG. 31 provides measurements from a series of bending tests applied to components and combinations of tube frame 5 and liner 3103 assemblies. The Y-axis of the graph shows the bending force required to bend the subject assembly or component, while the X-axis refers to the position along the length of the subject assembly or component where the force was applied and measured. When the liner is fully fused the tube frame 1005 is least flexible as measured by the 3-point Bend test. The bend tests were performed using a setup similar to that illustrated in FIG. 32, e.g., by supporting a length L of the tube frame 1005 at two points, then applying a force F to the midsection of that length, measuring the resulting deflection, and calculating and calculating a resulting stiffness value. The test fixture used to perform the measurements was a Chatillon® LTCM-6 digital motorized force tester.

As shown in the graph of FIG. 31, a tube frame 1005 without any liner disposed therein or thereon requires between approximately 0.22N-0.35N to bend. A tube frame 1005 with an unbonded, unfused liner disposed therein requires between approximately 0.335N-0.469N to bend. A tube frame 1005 with a partially bonded liner disposed therein requires between approximately 0.469N-1.088N to bend, depending on the proximity of the bending force to the location where the bonding/fusing is located (e.g., a higher bending force is required in close proximity to a fuse point, while significantly lower force is needed the further the distance from the fuse point). A tube frame 1005 with the liner fully fused to a tube frame requires between approximately 1.1N-1.405N to bend the assembly, which is close to 3× the bending force compared to the lower end of the bending force required for the partially fused assembly. As a result, a partially fused liner construct can provide flexibility and operable performance that is several times greater than traditional, fully-fused liner constructs.

For example, the liner 3203 may be intermittently or partially fused, bonded, and/or otherwise adhered to the tube frame 5 using different patterns, spacing, and/or shape(s) of the fuse points or segments that bond the liner 3203 to the tube frame 1005. Such patterns, spacing, dimensions, and/or shapes may be varied in conjunction with other variable features of the distal assembly (e.g., material selection, wall thickness, cut patterns, etc.) to provide the overall desired pushability and flexibility of the guide catheter extension.

Figure 33A:
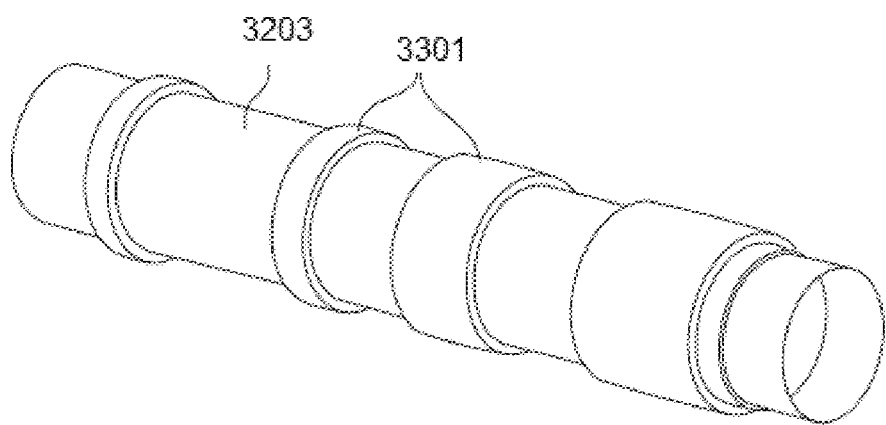
FIGS. 33a-33c depicts an example of a fuse pattern for an inner liner of a distal assembly constructed in accordance with the principles of the present disclosure.
Figure 33B:
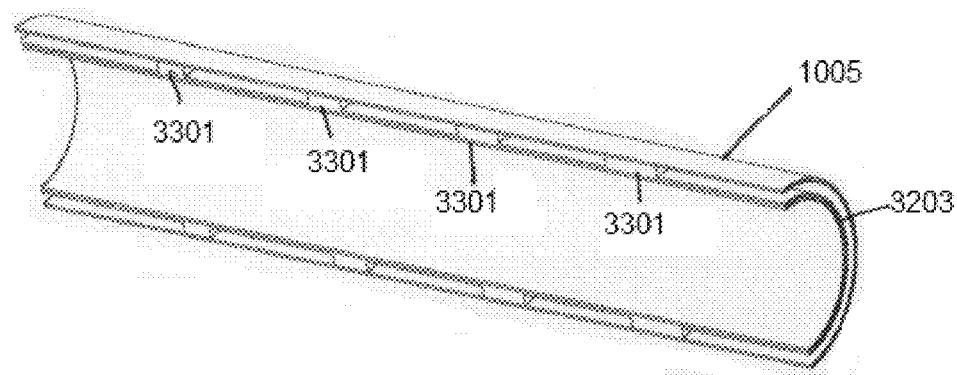
Figure 33C:
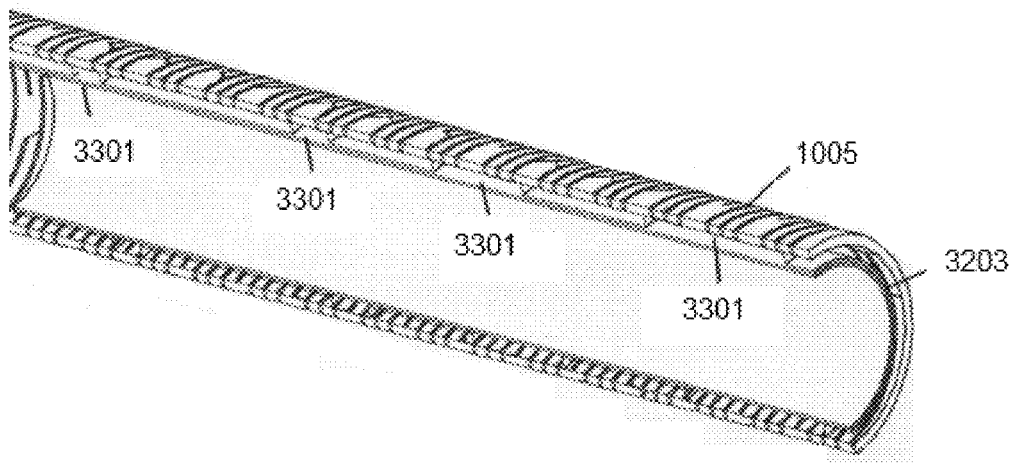

For example, coupling of the liner 3203 to the tube frame 1005, may include the creation or implementation of one or more fused segments 3301, each having a substantially ring-like or circumferential profile, as shown in FIG. 33a. Each substantially circumferential fused segment 3203 may have a width between approximately 1 mm (0.0393 inches) and approximately 2.54 cm (1 inch). A plurality of substantially circumferential fused segments may be employed along the length of the distal assembly, where sequential substantially circumferential fused segments are spaced apart by between approximately 1 mm (0.0393 inches) and approximately 2.54 cm (1 inch). FIGS. 33b-c. In another example, the liner 3203 may be coupled to the tube frame 5 at three locations—at or near the proximal 10 and distal ends 11 of the tube frame 5, and at or near the approximate midpoint of the tube frame 5.

In a preferred example, each fused segment 3301 may have a width between approximately 1 mm (0.0393 inches) and approximately 2 mm (0.0787 inches), and sequential fused segments may be spaced apart no less than approximately 12.7 mm (0.5 inches).

Figure 33D:
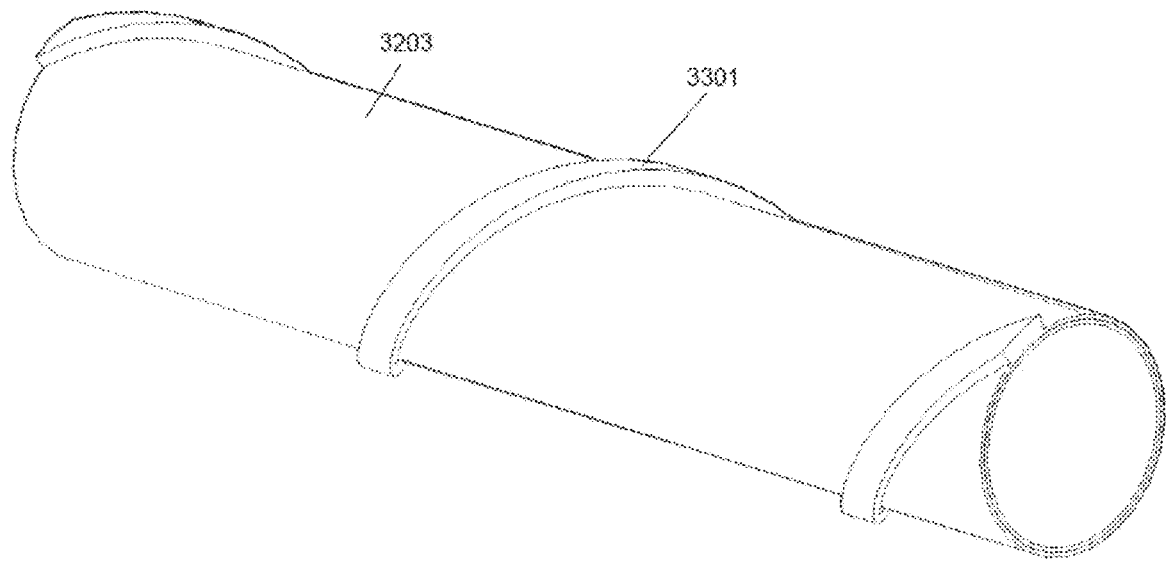
FIG. 33d depicts another example of a fuse pattern for an inner liner of a distal assembly constructed in accordance with the principles of the present disclosure.

In another example, a continuous, substantially continuous, and/or interrupted spiral pattern may be implemented for the fused segment(s) 3301. FIG. 33d. Such a fuse pattern could be achieved, for example, by rotating and pulling the tube frame 1005 across a heating point, thus providing the spiral pattern. The width, pitch, and/or spacing of the spiral pattern may be similar to the dimensions and examples provided above. A fusing pattern may be used such as a dashed line or interrupted spiral bonding points Alternatively, the liner 3203 may be fused to one or more segments proximal and/or distally to the rings, but otherwise 'float' unbound within the length of the lumen 1008 passing through the rings. The outer jacket 1020, discussed below, may similarly be fused to one or more segments proximal and/or distally to the rings, but otherwise 'float' unbound across the exterior of the length of the rings.

The length of the tube frame 1005 can vary. For example, the length of the tube frame can range from about 15 cm to about 35 cm, about 10 cm to about 25 cm, about 20 cm to about 45 cm, about 30 cm to about 50 cm, about 5 cm to about 15 cm or about 1-5 cm.

Depending on the material as well as the structural requirements in terms of flexibility, the wall thickness of the tube frame 5 at any point can vary, e.g., from about 0.05 mm to 2 mm, e.g., 0.05 mm to about 1 mm, about 0.1 mm, 0.2 mm, 0.3 mm, 0.4 mm, 0.5 mm, 0.6 mm, 0.7 mm, 0.8 mm, 0.9 mm, 1.0 mm, etc. The inner diameter of the tube can vary, e.g., from about 0.1 mm to about 2 mm, or from about 0.25 mm to about 1 mm, e.g., about 0.2 mm, about 0.3 mm, about 0.4 mm, about 0.5 mm, about 0.6 mm, about 0.7 mm, about 0.8 mm, about 0.9 mm, about 1 mm, about 2 mm, about 2.5 mm, about 3 mm thickness. The outer diameter of the tube frame 5 can also vary, e.g., from about 0.2 mm to about 3 mm, e.g., including about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.5 mm, about 3 mm thickness. The wall thickness of the tube frame 5 wall, the inner diameter and the outer diameter can each be constant throughout the length of the tube frame 5 or vary along the length of the tube frame 5.

In addition, the inner walls, i.e., lumen, of the tube can be coated with a liner 3201 that both protects the tube frame 1005 and facilitates transport of additional tools devices such as guidewires and balloons through the tubes of the catheter to distal locations. The liner 3201 can extend along a portion of the tube or can extend throughout the entire length of the tube. The liner 3201 can form a partial or complete tube.

Figure 34:
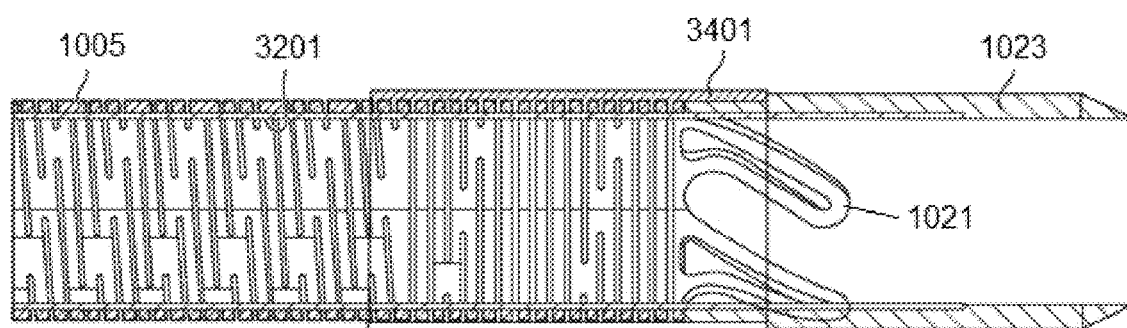
FIG. 34 is a lengthwise cross-sectional view of the distal region of a catheter constructed in accordance with the principles of the present disclosure.
Figure 35:
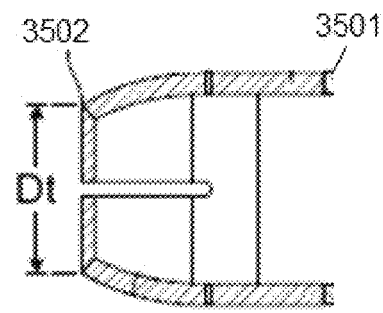
FIG. 35 is a lengthwise cross-sectional view of an example of a distal tip for a catheter constructed in accordance with the principles of the present disclosure.

The distal end 1013 of the tube frame 1005 may further include a catheter tip 1023 to aid in navigating both the inside of the external guide catheter as well as the anatomy to be accessed by the guide catheter extension. The catheter tip 1023 may have a rounded and/or tapered atraumatic profile and be coupled to the distal end of the tube frame 5 such that the catheter tip 1023 is substantially coaxially with the longitudinal axis LA of the tube frame 1005 and the lumen 1008 therethrough. The catheter tip 1023 may be secured to tube frame 1005 by fusing the catheter tip 1023 with the inner wall 1006, the outer jacket 3401, the liner 3201, and/or the axial protrusions 1021 extending from the distal end 1013 of the tube frame 1005. FIG. 34. In the example shown in FIG. 34, the catheter tip 1023 is 'sandwiched' between portions of the liner 3201 and the outer jacket 3401, and is further fused to portions of the axial protrusions 1021.

The catheter tip 1023 may be constructed from a relatively soft or pliable material, such as PEBAX®. The tip may be radiopaque, which may be achieved through the inclusion or infusion of tungsten, bismuth, and/or barium sulphate into the tip material, or as otherwise set forth herein.

Alternatively, at least two radiopaque markers, such as bands which practically or completely enclose the tube frame 1005 can be positioned along the tube frame 1005 for aiding radiographic visualization. The markers can include a radiopaque material, such as metallic platinum, platinum-iridium, Ta, gold, etc., in the form of wire coil or band, vapor deposition deposits, as well as radiopaque powders or fillers, e.g., barium sulfate, bismuth trioxide, bismuth sub carbonate, etc., embedded or encapsulated in a polymer matrix. Alternatively, the markers can be made from radiopaque polymers, such as radiopaque polyurethane.

In another embodiment, the catheter tip has a proximal end 3501 and a distal end 3502, where the distal end 3502 forms an inwardly bending curve forming an opening that has a diameter Dt smaller than that of the lumen 1008 of the tube frame 1005. The catheter tip 3501 near the distal end 3502 can include a number of cuts to make the distal tip more bendable, i.e., smaller "nose cone" like end in order to minimize trauma of the blood vessel wall when the distal tip is being advanced into a patient's vasculature.

In another type of catheter tip construction, the tapered core wire terminates short of the tip weld. It is common in such a construction to attach a very thin metallic ribbon at one (proximal) end to the core wire and at its other (distal) end to the tip weld. The ribbon serves as a safety element to maintain the connection between the core wire and the distal tip weld in the event of coil breakage. It also serves to retain a bend formed in the ribbon to maintain the tip in a bent configuration as is desirable when manipulating and steering the guidewire. Additionally, by terminating the core wire short of the tip weld, the segment of the helical coil between the distal end of the core wire and the tip weld is very flexible and floppy. The floppy tip is desirable in situations where the vasculature is highly tortuous and in which the guidewire must be capable of conforming to and following the tortuous anatomy with minimal trauma to the blood vessel. In another type of tip construction, the distal-most segment of the core wire is hammered flat (flat-dropped) so as to serve the same function as the shaping ribbon but as an integral unitary piece with the core wire. The tip of the flat dropped segment is attached to the tip weld.

The outer jacket 1020 may be constructed from nylon, polyether block amide, PTFE, FEP, PFA, PET, PEEK, etc., and/or combinations or composites thereof. The outer jacket 125 may have a wall thickness between approximately 0.00508 mm (0.00020 inches) and approximately 0.127 mm (0.0050 inches) to minimize any increased outer diameter of the guide catheter 102 as compared to the tube frame 1005 outer diameter. In a preferred example, the outer jacket 1020 may have a wall thickness between approximately 5 microns (0.00020 inches) and approximately 10 microns (0.00040 inches). The outer jacket 1020 may span a length 1014 of the tube frame 1005. The outer jacket 1020 provides an atraumatic, protective covering over the rings to eliminate or significantly reduce any trauma or pinching of surrounding tissue when the rings bend to contour and travel through curvilinear anatomy.

Figure 36A:
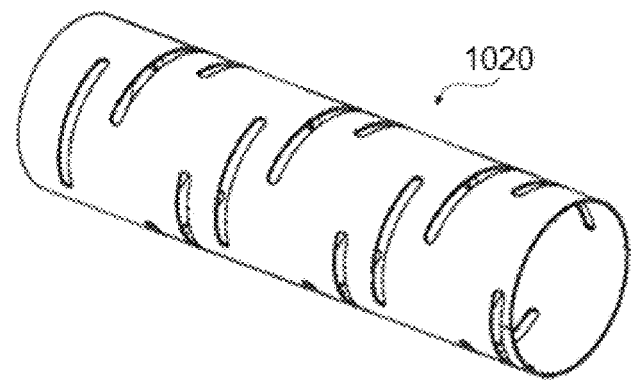
FIG. 36a-36d depict examples of outer jackets constructed in accordance with the principles of the present disclosure.
Figure 36B:
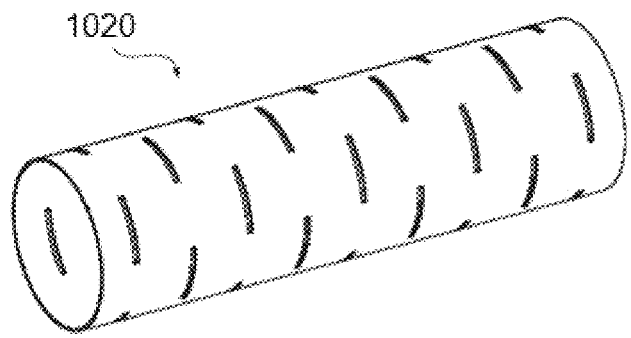
Figure 36C:
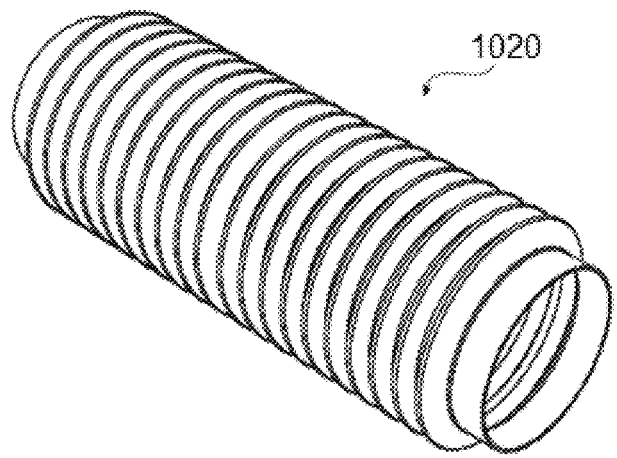
Figure 36D:
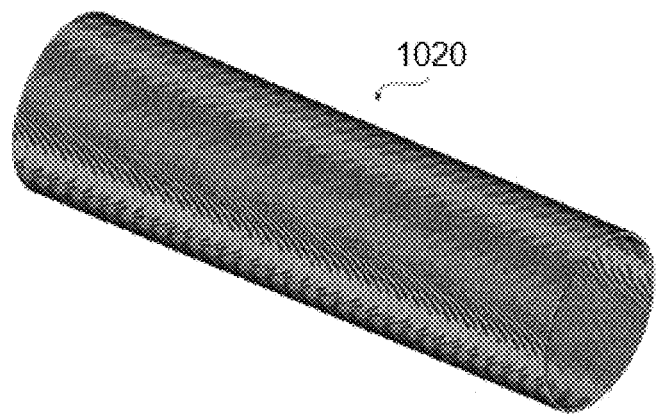

While the outer jacket 1020 illustrated in FIGS. 30, 34 has a substantially smooth, cylindrical configuration, the outer jacket 1020 may include one or more cut patterns or other geometric features to facilitate, complement, and/or contribute to the overall flexibility of the distal assembly. For example, the outer jacket 1020 may include an interrupted spiral cut pattern therein, as shown in FIG. 36*a*. Alternatively, the outer jacket 1020 may include a series of spaced, substantially linear cuts or holes therein, as shown in FIG. 36*b*. In another example, the outer jacket 1020 may have a substantially bellows-like configuration, as shown in FIG. 36*c*. FIG. 36*d* illustrates another example, where the outer jacket 1020 may include a wound spiral configuration.

The outer jacket 1020 can be made from a polymer, e.g., by enclosing the tube wall with a co-extruded polymeric tubular structure of single of multiple layers and heat shrinking the tubular structure or coating the tube frame 1005 via a dip coating process. The polymer jacket material can be nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone). Further, a portion of the tube frame 5 (or the entire length of guide catheter extension, including the guide catheter) may be coated with a hydrophilic polymer coating to enhance lubricity and trackability. Hydrophilic polymer coatings can include, but are not limited to, polyelectrolyte and/or a non-ionic hydrophilic polymer, where the polyelectrolyte polymer can include poly(acrylamide-co-acrylic acid) salts, a poly(methacrylamide-co-acrylic acid) salts, a poly(acrylamide-co-methacrylic acid) salts, etc., and the non-ionic hydrophilic polymer may be poly(lactams), for example polyvinylpyrollidone (PVP), polyurethanes, homo- and copolymers of acrylic and methacrylic acid, polyvinyl alcohol, polyvinylethers, snapic anhydride based copolymers, polyesters, hydroxypropylcellulose, heparin, dextran, polypeptides, etc. See e.g., U.S. Pat. Nos. 6,458,867 and 8,871,869. The coating can be applied by a dip coating process or by spraying the coating onto the tube outer and inner surfaces.

A lubricious coating or film may be added over the outer jacket to facilitate movement of the catheter through blood vessels. The lubricious coating can be composed of, for example, silicone or hydrogel polymers or the like, such as polymer networks of a vinyl polymer, polyalkylene glycols, alkoxypolyethylene glycols or an uncrosslinked hydrogel, e.g., Polyethylene oxide (PEO).

One or more surfaces of the guide catheter extension may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, other compounds disclosed herein, and the like, and mixtures and combinations thereof. Hydrophilic polymers may be blended among themselves or with formulated amounts of water insoluble compounds (including some polymers) to yield coatings with suitable lubricity, bonding, and solubility.

The tube frame 1005 (or a portion thereof) may be substantially uniform in diameter across its entire length. Alternatively, the tube frame 1005 can have a varying diameter across its length, e.g., a tapered configuration.

The tube frame 1005 can have variable flexibility, kinkability, torque to failure, torqueability, trackability, pushability, crossability, and rotational response. A variety of different tests are available for testing flexibility, kinkability, torque to failure, torqueability, trackability, pushability, crossability, and rotational response. Various standard tests for these properties known in the art are disclosed in, for example, http://www.protomedlabs.com/medical-device-testing/catheter-testing-functional-performance (retrieved Oct. 8, 2018).

Flexibility is the quality of bending without breaking. The flexibility of the tube is dependent on the material used, the interrupted spiral pattern, the wall thickness, the inner diameter and the outer diameter, and other variables. Flexibility can be determined by one of the following testing methods. One method of testing flexibility uses a proximal load cell to measure the ability of the device to advance and withdraw, with no loss of function or damage to the tortuous anatomy, over a specific bend angle. Alternatively, a roller system can be used to determine the smallest radius of curvature that the device can withstand without kinking. Additionally, tests can be performed by a cantilever beam to measure force and bending angle by calculating $F=[M\times(\% SR)]/(S\times100)$ with angularity at $50°$ where F=flexibility, M=total bending moment, % SR=scale reading average, and S=span length. Another method of testing flexibility is to use one- and four-point bending tests to evaluate flexibility under displacement control using a ZWICK 005 testing machine which detects the force F and the bending deflection f (https://www.zwick.com/en/universal-testing-machines/zwickiline, retrieved Oct. 29, 2018). The highest measured data describes the flexibility as determined by the equation $E \times I = (F \times L^3)/(3 \times f)$ (Nmm$^2$) where I=moment of inertia, E=Young modulus, L=bending length, f=bending deflection, and F=point force and E×I=flexibility.

Torque to failure or brake is the amount of twisting or rotational force the tubular member can withstand before a plastic deformation of the catheter components, a fracture or break occurs. One method for testing torque to failure is through the use of proximal and distal torque sensors which measure the amount of torque and the number of revolutions until device failure by rotating the device at a more proximal location and fixing the distal end while the device is routed through tortuous anatomy. Another testing method for calculating torque to failure is by testing torque strength immediately following submersion in 37±2° C. water for a set period of time. With a guidewire in place, the device can be inserted into a compatible guiding catheter which is constrained in a two-dimensional shape to replicate access into the coronary anatomy until the distal most 10 cm of the catheter is exposed beyond the guiding tip and is attached to a torque gauge to prevent rotation. The remainder of the catheter body is rotated in 360° increments until distortion, failure, breaks, fractures, kinks, or other damage occurs along the catheter or at the catheter tip, or for a set number of rotations.

Torqueability is the amount of torque, or rotation, lost from one end of the tube to the other end of the tube when a rotational force is exerted on one end. One method for testing torqueability is by using a proximal and distal torque sensor to measure the amount of torque transmitted through the device by rotating the device at a more proximal location and fixing the distal end while the device is routed through tortuous anatomy. Another method for testing torqueability is by using an artery simulating device for PTCA training, such as the PTCA trainer, T/N: T001821-2, designed by Shinsuke Nanto, M.D., which simulates a clinical tortuous path. An indicator attached to the catheter tip and inserted through the hole of a dial. The catheter body is connected to a rotator, for example T/N: T001923, and rotated clockwise in 90° increments to about 1080°. The angle measured by dial attached to the indicator on the catheter tip is used to calculate the ratio of the angle of rotation of the body to the angle of rotation of the tip, which corresponds with the amount of torque lost during rotation.

A method for testing trackability is to use a proximal load cell to measure the force to advance the device through a tortuous anatomy with or without the aid of a guiding accessory.

One method for testing pushability is to use a proximal and distal load cell to measure the amount of force the distal tip of the device sees when a known force is being applied to on the proximal end.

A method for testing crossability is to use a proximal load cell to measure the ability of the catheter device to advance and withdraw over a specific lesion site without loss of function or damage to the tortuous anatomy. Additionally, a roller system can determine the worst lesion that the device can withstand without damage.

One method for testing rotational response is by using proximal and distal rotation encoders to measure the amount of rotation transmitted through the device by rotating the device at a more proximal location and keeping the distal end free while the device is routed through tortuous anatomy.

The features of the guide catheter extension as disclosed and described herein provide significantly improved performance compared to existing catheters. The distal assembly, incorporating the features set forth herein, can provide an average stiffness between approximately 0.03 N/mm and approximately 0.10 N/mm along a substantial length thereof, which provides improved capabilities compared to existing prior art devices. The unexpected and improved capabilities of the guide catheter extension overall, resulting from the combination of the various specifications set forth herein (e.g., intermittent liner bonding, tube frame 1005 cut patterns, wall thickness, and other features) are demonstrated by the ability of the extension catheter 1000 to traverse narrow curvature that cannot be traversed by other devices. Moreover, the cut patterns in the tube frame provide improved flexibility while also providing improved lumen integrity (e.g., the ability to maintain the lumen diameter during significant bending and navigation of tortuous anatomy) compared to traditional braided or coil-reinforced catheters of the prior art.

Figure 37:
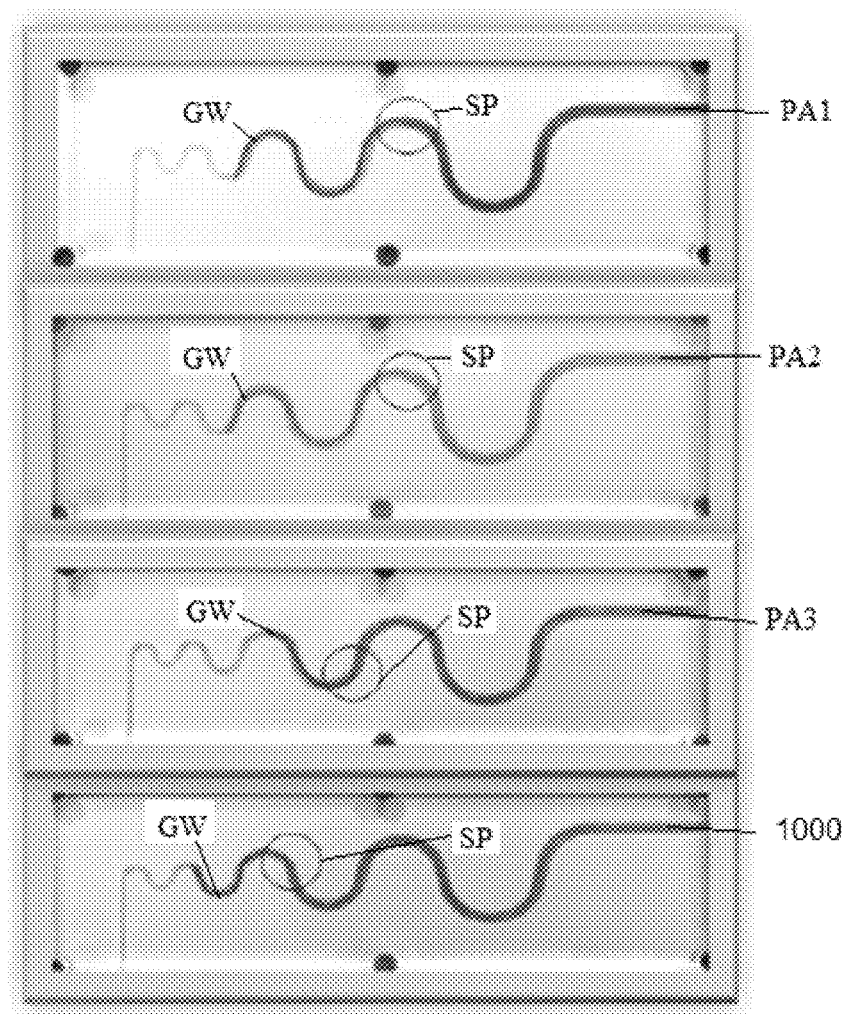
FIG. 37 is a photograph of various catheters navigating curves of decreasing radii.

For example, FIG. 37 is a photograph of 3 different prior art devices ("PA1", "PA2", "PA3") being pushed over a guidewire GW through an identical curvilinear path having decreasing radii from left-to-right. The stop point SP where each of the prior art devices stops and does not proceed through the path any further under an axial load (i.e., due to kinking, deformation, or otherwise) is circled. In comparison, an example of the guide catheter extension was pushed over a guidewire through the same curvilinear path to successfully reach a stop point SP at a much smaller radii than the prior art devices—radii as small as approximately 2.54 mm—without kinking or material deformation. This demonstrates the ability of guide catheter extension to traverse smaller, more tortuous anatomy and vasculature than existing devices, thereby allowing for wider application of treatment options and locations.

The variable flexibility of the sections of the tube frame also facilitates surgical procedures in which side-branch access is required or where tortuous vasculature is encountered such as in the central nervous system. Given the ability to use a wide variety of combinations from the base tube's material mechanical properties, the tubing dimensions (OD/ID), wall thickness, cut tubing's mechanical properties resulting from the cut pattern along the tube's (material composition, UTS, % Elongation modulus of Elasticity, and other combinations of material and mechanical properties (UTS, formulas defining cut pitch angle, cut width, helical cut arc length and uncut helical space between next helical arc cut), all enable the designer to tailor a variety of mechanical properties defined throughout the running length of the cut tube. Such resulting properties such as stiffness, flexibility and using the shape memory properties define a preset curvilinear shape are programmable and changeable.

Additionally, such an induced shape memory form would require a greater force to straighten or diminish and maintain via a resistive load force along the cut and shape treated portion of the distal tubular segment, to orient the shape set portion of the tube to revert back into a straight linear concentric coaxial configuration, which would enable the catheter to be advanced to the vascular target.

Such variables assembled together, to create a wide variety of structural shape combinations of tubes. These structural shapes can easily be temporarily diminished inline by advancing the tubes over a wire track, e.g., a guidewire, which exhibits mechanical properties of deformation that exceed the curvilinear shape's spring constant. This temporary deformation enables advancement of the catheter, the tubes, over the guidewire through the vascular anatomy. Simply put, the spring constant of the shaped curve portion is less than that of the wire segment it is tracking over. Once the retaining guidewire segment's spring constant is less than that of the set curvilinear shape, the cut shaped tube segment will revert back to its preset shape, unless acted upon by an additional other external forces or vascular confinement.

Such methods may be implemented to access and treat a myriad of varying conditions and/or diseases in anatomical regions, including, peripheral, cardiovascular, and neurological (e.g., central nervous system) having minimal or difficult access. For example, complex anatomic variation of blood vessels is common in the aortic arch, the hepatic arterial configuration, gastric arteries, celiac trunk, superior mesenteric, renal arteries, femoral arteries as well as axillary arteries. Kahn et al. *Complex arterial patterning in an anatomical donor. Translational Research in Anatomy.* 12: 11-19 (2018). The anatomic structure of a particular vasculature has direct clinical relevance, particularly during invasive diagnostic and surgical procedures. Not only can the anatomy of a vascular site vary significantly, but also, the procedure may require the use of multiple devices, e.g., wires, balloons and guide catheters. Guide catheter extension devices, such as the devices disclosed herein, can provide improved delivery of multiple interventional devices into such anatomy.

Figure 38C:
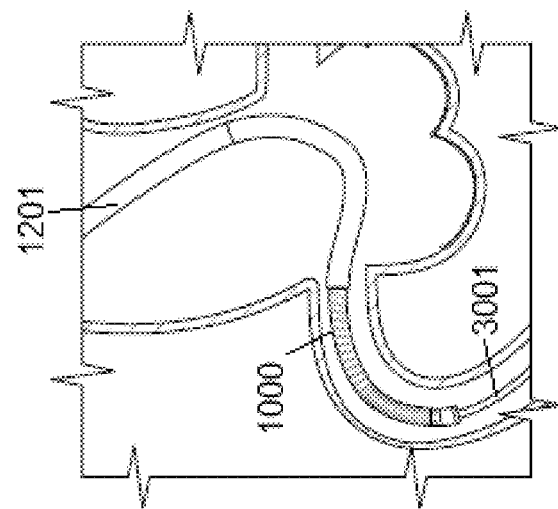
FIGS. 38a-38c illustrate an example of use of a catheter constructed in accordance with the principles of the present disclosure.
Figure 38B:
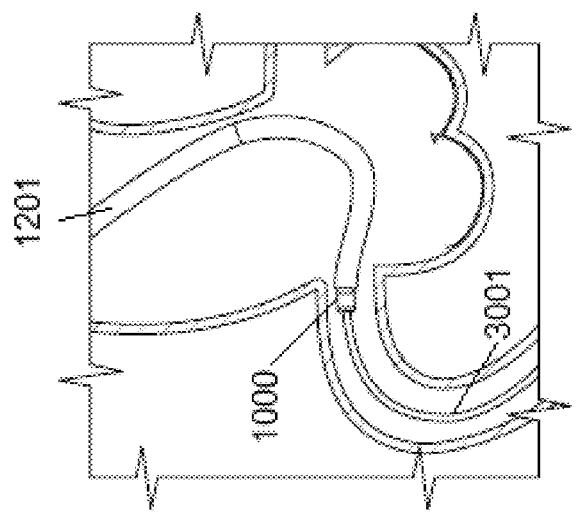
Figure 38A:
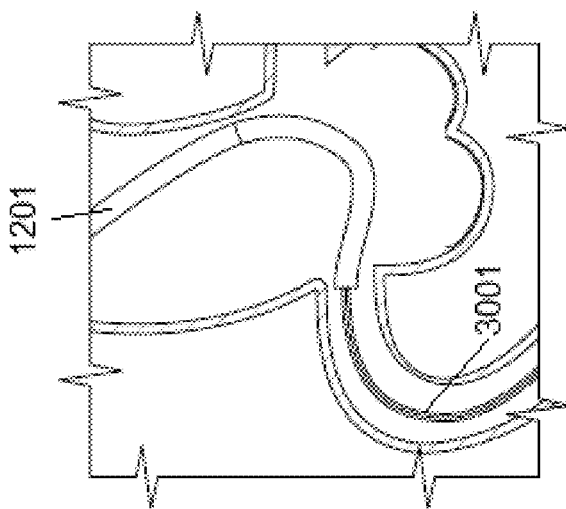

In one example of use, the guide catheter extension 1000 may be used to supplement and extend the reach of a typical guide catheter to ultimately reach and/or treat an anatomical location. For example, as shown in FIG. 38-*c*, a typical guide catheter GC 1201 may be passed over a guidewire GW 3001, through the aortic arch into an ostium of a coronary artery, which may have a stenotic lesion for treatment. Once the distal end of the guide catheter GC 1201 is seated in the ostium of the coronary artery, the guide catheter extension 1000 is passed through the interior of the guide catheter GC 1201 and extended distally of the distal end of the guide catheter GC 1201, deeper into the coronary artery.

The guidewire GW 3001 may then be pushed past the stenotic lesion or other occlusion. In some instances, the application of force to the guidewire GW 3001 could cause the guide catheter GC 1201 to dislodge from the ostium of the coronary artery in cases of a tough stenotic or occlusive lesion. However, the combination of guide catheter GC 1201 with the extending guide catheter extension 1000 inserted into the ostium provides improved distal anchoring of the devices and also provides stiffer back up support than the external guide catheter GC 1201 alone, thereby resisting dislodgement when the guidewire GW 3001 is passed through the lesion, and further provides improved back up support to assist in the positioning of a subsequent treating catheter that may include a stent or balloon.

Once the guidewire GW 3001 is pushed past the stenotic or occlusive lesion, a treating catheter (not shown) including a stent, balloon, and/or other treatment or diagnostic components can be passed along the guidewire to treat the lesion.

Such methods may be implemented to access and treat a myriad of varying conditions and/or diseases in anatomical regions having minimal or difficult access. For example, complex anatomic variation of blood vessels is common in the aortic arch, the hepatic arterial configuration, gastric arteries, celiac trunk, superior mesenteric, renal arteries, femoral arteries as well as axillary arteries. Kahn et al. Complex arterial patterning in an anatomical donor. Translational Research in Anatomy. 12: 11-19 (2018). The anatomic structure of a particular vasculature has direct clinical relevance, particularly during invasive diagnostic and surgical procedures. Not only can the anatomy of a vascular site vary significantly, but also, the procedure may require the use of multiple devices, e.g., wires, balloons and guide catheters. Guide catheter extension devices, such as the devices disclosed herein, can provide improved delivery of multiple interventional devices into such anatomy.

The scope of the present disclosure is not limited by what has been specifically shown and described hereinabove. Those skilled in the art will recognize that there are suitable alternatives to the depicted examples of configurations, constructions, and dimensions, and materials. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. The citation and discussion of any references in the application is provided merely to clarify the description of the present disclosure and is not an admission that any reference is prior art to the disclosure described herein. All references cited and discussed in this specification are incorporated herein by reference in their entirety. While certain embodiments of the present disclosure have been shown and described, it will be obvious to those skilled in the art that changes and modifications may be made without departing from the spirit and scope of the disclosure. The matter set forth in the foregoing description and accompanying drawings is offered by way of illustration only and not as a limitation.

What is claimed is:

1. A guide catheter extension, comprising:
   a push member having a proximal region and a distal region; and
   a tube frame defining:
      a longitudinal axis;
      a lumen therethrough having a diameter sufficient to receive an interventional cardiology device therethrough;
      a proximal opening of the lumen that is substantially perpendicular to the longitudinal axis; and
      a tongue element extending from a proximal segment of the tube frame, wherein the tongue element is directly coupled to the distal region of the push member,
   wherein the tongue element extends distal to the proximal opening of the lumen, wherein the tube frame includes cuts adjacent to a distal region of the tongue element, wherein the cuts create spaces between sides of the tongue element and the tube frame;
   and wherein the tube frame comprises a plurality of cut patterns therein.

2. The guide catheter extension of claim 1, wherein the tube frame has an average stiffness between approximately 0.03 N/mm and approximately 0.10 N/mm along a substantial length thereof.

3. The guide catheter extension of claim 2, wherein the tube frame is pushable through a curve having a radius of approximately 2.5 mm without kinking.

4. The guide catheter extension of claim 3, wherein the tube frame has a wall thickness between approximately 0.0254 mm and approximately 0.254 mm.

5. The guide catheter extension of claim 1, wherein the plurality of cut patterns comprises a plurality of interrupted spiral-cut patterns.

6. The guide catheter extension of claim 5, wherein the plurality of interrupted spiral-cut patterns extends along a length of the tube frame having an average stiffness between 0.002-0.004 N/mm.

7. The guide catheter extension of claim 1, wherein the push member comprises a lumen.

8. The guide catheter extension of claim 1, wherein the plurality of cut patterns comprises a continuous spiral-cut pattern.

9. The guide catheter extension of claim 8, wherein the continuous spiral-cut pattern extends along a length of the tube frame having an average stiffness between 0.001-0.003 N/mm.

10. The guide catheter extension of claim 1, wherein the plurality of cut patterns comprises a plurality of rings coupled together by a plurality of struts.

11. The guide catheter extension of claim 10, wherein the plurality of struts are axially aligned.

12. The guide catheter extension of claim 10, wherein the plurality of struts are angularly offset from one another at an angle ranging from about 5 degrees and to about 180 degrees.

13. The guide catheter extension of claim 12, wherein the struts form a helical pattern.

14. The guide catheter extension of claim 10, wherein the plurality of rings extends along a length of the tube frame having an average stiffness between 0.005-0.016 N/mm.

15. The guide catheter extension of claim 10, further comprising an outer polymer jacket covering at least a portion of the plurality of rings, wherein the outer polymer jacket is not fused to any portion of the plurality of rings.

16. The guide catheter of claim 1, wherein the plurality of cut patterns comprises at least two cut patterns selected from the group consisting of continuous spirals, interrupted spirals, interconnected rings and zones or combinations thereof.

17. The guide catheter extension of claim 1, further comprising a polymer liner disposed within the lumen.

18. The guide catheter extension of claim 17, wherein the polymer liner comprises at least two polymer layers, wherein each polymer layer has a different glass transition temperature and wherein the polymer layer adjacent to the inner wall of the tube frame has a lower glass transition temperature (melt temperature) than the polymer layer adjacent to the lumen.

19. The guide catheter extension of claim 1, wherein the cuts are substantially parallel to the distal region of the tongue element, and wherein the cuts are substantially parallel to the longitudinal axis of the tube frame.

20. The guide catheter extension of claim 1, further comprising a polymer flare circumscribing the proximal opening of the lumen, and wherein the flare has a greater diameter than an outer diameter of the tube frame.

21. The guide catheter extension of claim 1, wherein a longitudinal axis of a distal segment of the tongue element is not parallel to the longitudinal axis of the tube frame.

22. The guide catheter extension of claim 21, wherein the tongue element extends through an opening defined by the flare.

23. A guide catheter extension, comprising:
a push member having a proximal end and a distal end;
a tube frame directly coupled by a tongue element to the distal end of the push member, the tube frame defining;
a longitudinal axis;
a lumen having a diameter sufficient to receive an interventional vascular device therethrough; and
a proximal opening of the lumen that is substantially perpendicular to the longitudinal axis; and
wherein the tongue element extends from a proximal segment of the tube frame and is coupled to the push member, wherein the tongue element extends distal to the proximal opening of the lumen, wherein the tube frame includes cuts adjacent to a distal region of the tongue element, and wherein the cuts create spaces between sides of the tongue element and the tube frame.

24. The guide catheter extension of claim 23, wherein the tongue element is a unitary component of the tube frame.

25. The guide catheter extension of claim 23, wherein the cuts are substantially parallel to the distal region of the tongue element, and wherein the cuts are substantially parallel to the longitudinal axis of the tube frame.

26. The guide catheter extension of claim 25, further comprising a keyhole in the tube frame adjacent to each of the cuts.

27. The guide catheter extension of claim 23, wherein the push member further comprises a lumen.

28. The guide catheter extension of claim 23, wherein a longitudinal axis of a distal segment of the tongue element is not parallel to the longitudinal axis of the tube frame.

29. The guide catheter extension of claim 23, further comprising a polymer liner disposed within the lumen of the tube frame.

30. The guide catheter extension of claim 23, further comprising a polymer flare circumscribing the proximal opening of the lumen, and wherein the flare has a greater diameter than an outer diameter of the tube frame.

31. The guide catheter extension of claim 30, wherein the tongue element extends through an opening defined by the flare.

32. The guide catheter extension of claim 23, wherein the tube frame has an average stiffness between approximately 0.03 N/mm and approximately 0.10 N/mm along a substantial length thereof, and wherein the tube frame has a wall thickness between approximately 0.0254 mm and approximately 0.254 mm.

33. The guide catheter extension of claim 23, wherein the tube frame is pushable through a curve having a radius of approximately 2.5 mm without kinking.

34. The guide catheter extension of claim 23, wherein the push member comprises a lumen.

35. The guide catheter extension of claim 23, further comprising a polymer liner disposed within the lumen.

36. A guide catheter extension, comprising:
a push member having a lumen, a proximal end and a distal end;
a nitinol tube frame coupled to the distal end of the push member, the tube frame defining a longitudinal axis, a lumen having a diameter sufficient to receive an interventional vascular device therethrough, and a proximal opening of the lumen that is substantially perpendicular to the longitudinal axis, wherein the tube frame comprises a plurality of cut patterns therein;
a polymer liner disposed within the lumen of the tube frame;
a plurality of protrusions extending from a proximal region of the tube frame;
a polymer flare coupled about the plurality of protrusions and circumscribing a proximal opening of the lumen, wherein the flare has a greater diameter than an outer diameter of the tube frame;
a tongue element unitary with and extending from a proximal segment of the tube frame, wherein the tongue element is coupled to the push member, and wherein the tongue element extends distal to the proximal opening of the lumen, wherein the tube frame includes cuts adjacent to a distal region of the tongue element, and wherein the cuts create spaces between sides of the tongue element and the tube frame;
an outer polymer jacket covering a least a portion of the tube frame; and
a polymer tip coupled to a distal region of the tube frame.

* * * * *